(12) United States Patent
Chen et al.

(10) Patent No.: US 6,794,501 B2
(45) Date of Patent: Sep. 21, 2004

(54) COLON CANCER ANTIGEN PANEL

(75) Inventors: Yao-Tseng Chen, New York, NY (US); Lloyd J. Old, New York, NY (US); Matthew J. Scanlan, New York, NY (US); Elisabeth Stockert, New York, NY (US)

(73) Assignees: Ludwig Institute for Cancer Research, New York, NY (US); Cornell Research Foundation, Inc., Ithaca, NY (US)

( * ) Notice: Subject to any disclaimer, the term of this patent is extended or adjusted under 35 U.S.C. 154(b) by 88 days.

(21) Appl. No.: 09/849,602

(22) Filed: May 4, 2001

(65) Prior Publication Data
US 2003/0165834 A1 Sep. 4, 2003

(51) Int. Cl.[7] .................. C07H 21/04; C07K 14/00; G01N 33/53; A01N 37/18
(52) U.S. Cl. ............. 536/23.1; 530/350; 435/7.1; 514/2
(58) Field of Search .................. 536/23.1; 530/350; 435/7.1; 514/2; 436/64

(56) References Cited

U.S. PATENT DOCUMENTS

| | | |
|---|---|---|
| 4,816,567 A | 3/1989 | Cabilly et al. |
| 5,225,539 A | 7/1993 | Winter |
| 5,585,089 A | 12/1996 | Queen et al. |
| 5,693,762 A | 12/1997 | Queen et al. |
| 5,804,381 A | 9/1998 | Chen et al. |
| 5,859,205 A | 1/1999 | Adair et al. |
| 5,962,256 A | 10/1999 | Moore et al. |

FOREIGN PATENT DOCUMENTS

| | | |
|---|---|---|
| WO | WO 99/04265 A2 | 1/1999 |
| WO | WO 99/14326 A1 | 3/1999 |
| WO | WO 99/60986 A2 | 12/1999 |

OTHER PUBLICATIONS

Attwood, Science; 290:471–473, 2000.*
Gerhold et al. BioEssays, 18(12):973–981, 1996.*
Lopez et al. Molecular Biology, 32:881–891, 1999.*
Russell et al. Journal of Molecular Biology, 244:332–350, 1994.*
Wells et al. Journal of Leukocyte Biology, 61(5):545–550, 1997.*
Chen, et al. (1997) Proc Natl Acad Sci USA 94:1914–1918.
Clark, et al. (1994) Nature Genetics 7(4):502–508.
Crew, et al. (1995) EMBO J. 14(10):2333–2340.
Ding, et al. (1994) Biochem Biophys Res Commun. 202(1):549–555.
Fukunaga, et al. (1997) EMBO J. 16(8):1921–1933.
Griggs et al., (2001) *Lancet Oncol.* 2:82, 1–6.
Grozinger, et al. (1999) Proc. Natl. Acad Sci USA 96:4868–4873.
Harlow, et al. (1985) Molecular & Cell Biol. 5(7):1601–1610.
Hendrich, et al. (1998) Molecular & Cell Biol. 18(11):6538–6547.
Kim, et al. (1999) Molecular & Cell Biol. 19(9):6323–6332.
Kim, et al. (1997) Biochim Biophys Acta Dec 12;1359(3):181–6.
Kunkel, (1985) *Proc. Nat. Acad. Sci. U.S.A.* 82: 488–492.
Macbeath et al., (2000) "Printing Proteins as Microarrays for High–Throughput Function Determination," *Science* 289(5485):1760–1763.
Rosen, *Oncologist* 5:20, 2000, 1–8.
Sahin et al. *Proc. Natl. Acad. Sci. USA* 92:11810–11813, 1995.
Scanlan, et al., *Int. J. Cancer* 76:652–658 (1998).
Scanlan, et al., *Int. J. Cancer* 83:456–64, (1999).
The Chipping Forecast, *Nature Genetics*, vol. 21, Jan. 1999, 1–60.

* cited by examiner

*Primary Examiner*—Ardin H. Marschel
*Assistant Examiner*—Cheyne D Ly
(74) *Attorney, Agent, or Firm*—Wolf, Greenfield & Sacks, P.C.

(57) ABSTRACT

The invention provides methods for diagnosing cancer including colon cancer, based on the identification of certain colon cancer-associated polypeptides as antigens that elicit immune responses in colon cancer. The identified antigens can be utilized as markers for diagnosing colon cancer, and for following the course of treatment of colon cancer.

14 Claims, No Drawings

SEQUENCE LISTING

<160> NUMBER OF SEQ ID NOS: 30

<210> SEQ ID NO 1
<211> LENGTH: 5901
<212> TYPE: DNA
<213> ORGANISM: Homo sapiens

<400> SEQUENCE: 1

```
ctggagttca agatttctga tgaggaggca gatgatgcag atgctgctgg gagggattcc      60
ccctccaaca cctcccagtc agaacagcag gaatctgttg atgcagaagg cccagtggta     120
gaaaaaatta tgagcagtcg ttcagtaaaa aagcagaagg aatctggaga ggaggtagaa     180
attgaggaat tctatgtgaa atacaaaaac ttctcttatc ttcattgtca gtgggcatct     240
atagaagatc tggaaaaaga taagagaatt cagcaaaaaa ttaaacgatt taaggcaaag     300
cagggccaga acaagttcct ttcagagatt gaggatgagc ttttttaatcc agattatgtg     360 gaggttgacc ggataatgga ctttgcacgt agcacagatg accggggaga gcctgtgact     420
cactatctgt tgaagtggtg ttcacttcct tatgaagaca gcacgtggga gcggaggcag     480
gacatagatc aagcaaagat cgaggagttt gagaaactaa tgtccaggga gccggaaaca     540
gagcgtgtgg agcgacctcc tgctgatgat tggaagaaat cggagagttc cagggagtat     600
aaaaacaata acaaactcag ggaataccag ttggagggag taaactggct acttttcaat     660
tggtacaaca tgcgaaactg cattttagca gatgaaatgg gtttgggaaa aactatccag     720
tccattacat ttctctatga gatatatttg aaaggaatcc atggcccttt tttagtaatt     780
gccccattgt ccacaatccc caactgggaa agggaattcc gaacctggac agagttgaac     840
gtggttgtgt atcatgggag tcaagctagt cgtcggacca ttcagttgta tgaaatgtac     900
ttcaaagatc cccagggtcg agtgataaag gggtcctata agtttcatgc catcatcact     960
acatttgaga tgattttgac tgattgtcct gagctgcgga atattccatg gcgctgtgta    1020
gtcattgatg aagcccacag gctgaagaac aggaactgca agctgttgga gggactcaag    1080
```

-continued

```
atgatggact tggaacacaa agtgctgctg acgggaaccc cactccagaa cactgtggaa      1140
gaactcttca gcttgcttca tttcttggaa ccaagtcgct tcccttcaga aaccacattt      1200
atgcaagaat ttggtgatct aaaaacagaa gagcaggtgc aaaaacttca agctattcta      1260
aagccaatga tgttgagacg tctcaaagag gatgtagaaa agaacttggc ccccaaagaa      1320
gaaactatta ttgaagttga gctaacaaac attcagaaga aatattaccg agccatcctt      1380
gagaagaatt tcacatttct ttccaaggc ggtggtcaag ctaacgtacc taacctatta       1440
aacactatga tggaattgcg gaagtgctgc aatcatccgt accttatcaa tggtgctgaa      1500
gagaaaattt tggaagagtt taaagaaaca cacaatgcag agtctccaga ttttcagctc      1560
caggcaatga tccaggctgc tggcaagcta gtgctgattg acaagctgct gccaaaactg      1620
aaggctggtg ccacagggt gcttatcttt tcccagatgg tgcgctgctt ggacatactg       1680
gaagactacc tcattcaaag acggtaccca tatgaaagga tcgacggccg agtaagaggc      1740
aacctccgcc aggcagctat cgacagattc tccaaacctg attctgatag gtttgttttc      1800
ctcctgtgta caagggcagg aggtttaggc attaacctca ctgctgctga tacctgcatc      1860
atctttgatt cagactggaa tccccaaaat gacctccagg ctcaggctag atgtcataga      1920
ataggacaga gcaaatctgt gaaaatctac aggctgatta caagaaattc ctatgaaagg      1980
gaaatgttcg acaaggctag tttgaaactg ggcctggata agctgtgct acagtctatg       2040 agtggaagag aaaatgctac caatggggta caacagcttt ccaagaaaga aatagaggat      2100
cttctacgaa aaggggccta tggtgcactc atggatgagg aggatgaagg gtctaaattc      2160
tgtgaagaag atattgatca gatcctccta cgtcgaaccc acaccattac cattgagtca      2220
gaagggaaag gttccacatt tgctaaggcc agttttgttg catctggaaa taggacagat      2280
atttccttgg atgatccaaa tttctggcaa aagtgggcta agaaggctga attggatatt      2340
gatgccttaa atgggaggaa caacctggtt attgatactc caagagtgag aaagcagacc      2400
aggctctaca gtgcagtgaa ggaagatgag ctgatggagt tctcagactt ggaaagtgat      2460
tctgaagaaa agccctgtgc aaagccacgg cgtccccagg ataagtcaca gggctatgca      2520
aggagtgaat gtttcagggt ggagaagaat ctgcttgtct atggttgggg acggtggaca      2580
gacattcttt cccacggacg ctataaacgc caactcactg agcaagatgt agaaaccatc      2640
tgcagaacca tcctggtgta ctgtcttaat cattacaaag gggatgagaa tatcaaaagc      2700
ttcatctggg atctgatcac acccacagcg gatggccaga ctcgagcctt ggtcaaccat      2760
tccggtttgt cagctcctgt gccaagggga aggaagggaa agaaggtgaa agcccagagc      2820
acacagccgg tggtgcagga tgccgactgg ctggccagct gcaacccaga tgccctgttc      2880
caggaggaca gctacaagaa acacctgaag catcactgta caaggtcct gctgcgtgtc        2940 cgcatgctgt actacctaag acaagaagtg ataggagacc aggcggataa gatcttagag      3000
ggtgctgact caagtgaagc cgatgtgtgg atccctgaac ctttccatgc tgaagttcct      3060
gcagattggt gggataagga agcagacaaa tccctcttaa ttggagtgtt caaacatggc      3120
tatgagaagt acaactccat gcgagctgac cccgcgctgt gctttctgga acgagtcggt      3180
atgcctgatg ccaaggccat agctgccgag caaagaggaa cagacatgct agcagatggt      3240
ggtgacgggg gagaatttga tagagaagat gaagacccag aatataaacc aaccagaaca      3300
ccgttcaaag atgaaataga tgaatttgca aattctcctt cagaggataa ggaagaatcc      3360
atggaaatac atgccacagg caagcacagt gagagtaatg ctgagttagg ccaactttac      3420
```

```
tggcctaaca cttcaaccct gactacacgt ctgcgccggc tcattactgc ctatcagcgc    3480
agctataaaa ggcaacagat gaggcaagag gccctaatga agactgaccg gcgcagacgg    3540
cggcctcgag aggaagtgag agctctggaa gcggaaaggg aagctattat atctgagaag    3600
cggcaaaagt ggacaagaag agaagaggct gattttacc gtgtggtatc cacctttggg    3660 gttattttg accctgtgaa acagcaattt gactggaacc aatttagagc ctttgccagg    3720
cttgacaaaa aatctgatga gagtttggag aaatacttca gttgttttgt ggccatgtgt    3780
aggcgagtat gtcgaatgcc cgtcaagcca gatgatgaac cgcccgacct ctcctccata    3840
attgagccga tcacagagga gcgagcctct cgaactctgt accgcattga gctgctacgg    3900
aagatccgcg agcaggttct ccatcacccc cagctgggag agaggcttaa gctctgccag    3960
ccaagcttgg atctgccaga gtggtgggag tgtggacggc atgaccgaga cttgctggtt    4020
ggtgctgcta acacggggt cagtcggacg gattatcaca tcctcaatga ccctgagtta    4080
tccttcttgg atgcacataa aactttgct caaaacagag gggcaggtaa tacatcttcc    4140

ttgaacccac tggcagttgg atttgtccag actcctccag tcatctcatc tgctcatatt    4200
caagatgaga gggtactgga acaagccgaa ggcaaagtgg aggagcctga aacccagct    4260 gccaaggaga aatgtgaggg caaagaagag gaagaagaaa ccgatggcag cgggaaggag    4320
agcaagcagg aatgtgaggc agaggccagc tctgtgaaaa atgaactgaa aggtgttgag    4380
gtcggcgcag acactgggtc caaatctatt tcagagaaag gttccgaaga ggatgaagag    4440
gaaaagctgg aggatgacga taagtcggaa gagtcttccc agcccgaagc aggagctgtc    4500
tctagaggga agaattttga tgaagaaagc aatgcttcca tgagcactgc tagagatgaa    4560
acccgagatg gattctacat ggaggacgga gatccttcag tagctcagct ccttcatgaa    4620
agaacatttg ccttctcgtt ttggcctaag gatagagtaa tgataaaccg cttagacaac    4680
atctgtgaag cagtgttgaa aggcaaatgg ccagtaaata ggcgccagat gттттgaттtc    4740 caaggcctca tcccaggtta cacacccacc acagtggaca gccctttgca gaagaggagc    4800

tttgctgagc tctccatggt cggccaagcc agcattagtg ggagtgagga catcactacg    4860

tctcctcagt tgtcaaagga agatgccctc aacctctctg tccctcgcca gcggaggagg    4920
aggaggagaa aaatcgaaat tgaggccgaa agagctgcca agaggcgaaa tctcatggag    4980

atggttgccc agcttcgaga gtctcaggtg gtctcagaaa atggacaaga aaaagttgta    5040
gatttatcaa aggcctcaag agaggcaaca agctctacct caaatttttc atctctttct    5100

tcaaagttta tcttgcctaa tgtctcaaca ccagtgtctg atgcctttaa gactcaaatg    5160
gaactgctcc aagcaggcct ttcgcgcaca cccacaaggc atctccttaa tggctcccta    5220
gtggatggag agcctcccat gaagaggagg cggggaagga ggaaaaatgt ggagggactt    5280
gatctgcttt tcatgagcca caaacggacg tcattgagtg cagaggatgc tgaggtgacc    5340
aaagcttttg aagaagatat agagacccca ccaacaagaa acattccttc tcccggacag    5400
ctggacccag acacacggat ccctgttatc aatcttgaag atgggactag gctggtgggg    5460
gaagatgctc taaaaataa ggatttagtt gaatggctga agctgcaccc tacttacact    5520
gttgatatgc caagttatgt accaaagaat gcagatgtgc tgttttcctc attcagaaa    5580 ccgaaacaga aacgacatag atgtcgaaac cctaataaat tggataaaa cactttgaca    5640 ggagaagaaa gggtgcctgt tgtcaataaa cgaaatggga agaagatggg tggagctatg    5700
gcgcctccaa tgaaggatct аccсcaggтgg ctggaagaaa atcctgaatt tgcagttgct    5760
ccagactgga ctgatатaгт taagcagtct ggttttgttc ctgagtcgat gtttgaccgc    5820
```

-continued cttctcactg ggcctgtagt gcggggagag ggagcgagca gaagaggaag aaggcccaaa    5880
agtgagatcg ccagagcagc c    5901

<210> SEQ ID NO 2
<211> LENGTH: 485
<212> TYPE: DNA
<213> ORGANISM: Homo sapien
<220> FEATURE:
<221> NAME/KEY: Unsure
<222> LOCATION: (252)..(252)
<223> OTHER INFORMATION: n = a, g, c, or t/u
<220> FEATURE:
<221> NAME/KEY: Unsure
<222> LOCATION: (301)..(301)
<223> OTHER INFORMATION: n = a, g, c, or t/u
<220> FEATURE:
<221> NAME/KEY: Unsure
<222> LOCATION: (371)..(371)
<223> OTHER INFORMATION: n = a, g, c, or t/u
<220> FEATURE:
<221> NAME/KEY: Unsure
<222> LOCATION: (390)..(390)
<223> OTHER INFORMATION: n = a, g, c, or t/u
<220> FEATURE:
<221> NAME/KEY: Unsure
<222> LOCATION: (417)..(417)
<223> OTHER INFORMATION: n = a, g, c, or t/u
<220> FEATURE:
<221> NAME/KEY: Unsure
<222> LOCATION: (434)..(434)
<223> OTHER INFORMATION: n = a, g, c, or t/u
<220> FEATURE:
<221> NAME/KEY: Unsure
<222> LOCATION: (437)..(437)
<223> OTHER INFORMATION: n = a, g, c, or t/u
<220> FEATURE:
<221> NAME/KEY: Unsure
<222> LOCATION: (442)..(442)
<223> OTHER INFORMATION: n = a, g, c, or t/u
<220> FEATURE:
<221> NAME/KEY: Unsure
<222> LOCATION: (449)..(449)
<223> OTHER INFORMATION: n = a, g, c, or t/u
<220> FEATURE:
<221> NAME/KEY: Unsure
<222> LOCATION: (452)..(452)
<223> OTHER INFORMATION: n = a, g, c, or t/u
<220> FEATURE:
<221> NAME/KEY: Unsure
<222> LOCATION: (460)..(460)
<223> OTHER INFORMATION: n = a, g, c, or t/u
<220> FEATURE:
<221> NAME/KEY: Unsure
<222> LOCATION: (461)..(461)
<223> OTHER INFORMATION: n = a, g, c, or t/u
<220> FEATURE:
<221> NAME/KEY: Unsure
<222> LOCATION: (476)..(476)
<223> OTHER INFORMATION: n = a, g, c, or t/u

<400> SEQUENCE: 2
ggcgcccctc gctgccccgc gcgctcccg ccgcccccca tgagcgcagc cccgcgcggc      60
ccgggtccgt aggcggcggg gcgcccccca tgctgctgca gcccgcgccg tgcgccccga    120
gcgcgggctt cccgcggccc ctggccgccc ccggcgccat gcacttgttc gcagaaggac    180
accacgttca ccaagatctt cgtgggcggc ctgccgtacc acactaccga cgcctcgctc    240
aggaagtact tngagggctt cggcgacatc tgaggaggcc gtggtcatca ccgaccgcca    300
nacgggcaag tccgcggct acggcttcgt gaccatggcc gaccgggcgg cagctgagag    360
ggcttgcaaa nacccgaacc ccatcatcgn cggccgccag gccaacgtga acctggnata    420

```
tttgggcgcc aagntcncgg anccttcana cnggctttgn nattggggtg caacanctgc    480
accccc                                                              485

<210> SEQ ID NO 3
<211> LENGTH: 2885
<212> TYPE: DNA
<213> ORGANISM: Homo sapien

<400> SEQUENCE: 3
ggaattcctc ttgtcgaagt caaaggagcc cacaccaggc ggcctcaacc attccctccc     60
acagcacccc aaatgctggg gagcccacca tgcttctttg gaccagagtt ccctcccca    120 gagcggcccc cctgggacgc ctccctccta caaactgcct ttgcctgggc cctacgacag    180
tcgagacgac ttccccctcc gcaaaacagc tctgaaccc aacttgaaag tgcgttcaag     240
gctaaaacag aaggtggctg agcggagaag cagtcccctc ctgcgtcgca aggatgggac    300
tgttattagc acctttaaga agagagctgt tgagatcaca ggtgccgggc ctgggcgtc     360 gtccgtgtgt aacagcgcac ccggctccgg ccccagctct cccaacagct cccacagcac    420
catcgctgag aatggcttta ctggctcagt ccccaacatc cccactgaga tgctccctca    480
gcaccgagcc ctccctctgg acagctcccc aaccagttc agcctctaca cgtctccttc     540
tctgcccaac atctccctag ggctgcaggc cacggtcact gtcaccaact cacacctcac    600
tgcctccccg aagctgtcga cacagcagga ggccgagagg caggccctcc agtccctgcg    660
gcagggtggc acgctgaccg gcaagttcat gagcacatcc tctattcctg gctgcctgct    720
gggcgtggca ctggagggcg acgggagccc ccacgggcat gcctccctgc tgcagcatgt    780
gctgttgctg gagcaggccc ggcagcagag caccctcatt gctgtgccac tccacgggca    840
gtccccacta gtgacgggtg aacgtgtggc caccagcatg cggacggtag gcaagctccc    900
gcggcatcgg cccctgagcc gcactcagtc ctcaccgctg ccgcagagtc cccaggccct    960
gcagcagctg gtcatgcaac aacagcacca gcagttcctg gagaagcaga agcagcagca   1020
gctacagctg ggcaagatcc tcaccaagac aggggagctg cccaggcagc ccaccaccca   1080
ccctgaggag acagaggagg agctgacgga gcagcaggag gtcttgctgg gggagggagc   1140
cctgaccatg ccccgggagg gctccacaga gagtgagagc acacaggaag acctggagga   1200
ggaggacgag gaagaggatg gggaggagga ggaggattgc atccaggtta aggacgagga   1260
gggcgagagt ggtgctgagg aggggcccga cttggaggag cctggtgctg gatacaaaaa   1320
actgttctca gatgcccaac cgctgcaacc tttgcaggtg taccaagcgc ccctcagcct   1380
ggccactgtg ccccaccaag ccctgggccg tacccaatcc tcccctgctg cccctggggg   1440
catgaagaac cccccagacc aacccgtcaa gcacctcttc accacaagtg tggtctacga   1500
cacgttcatg ctaaagcacc agtgcatgtg cgggaacaca cacgtgcacc ctgagcatgc   1560
tggccggatc cagagcatct ggtcccggct gcaggagaca ggcctgctta gcaagtgcga   1620
gcggatccga ggtcgcaaag ccacgctaga tgagatccag acagtgcact ctgaatacca   1680
caccctgctc tatgggacca gtcccctcaa ccggcagaag ctagacagca agaagttgct   1740
cggtcccatc agccagaaga tgtatgctgt gctgccttgt gggggcatcg ggtggacag    1800 tgacaccgtg tggaatgaga tgcactcctc cagtgctgtg cgcatggcag tgggctgcct   1860
gctggagctg gccttcaagg tggctgcagg agagctcaag aatggatttg ccatcatccg   1920 gccccagga caccacgccg aggaatccac agccatggga ttctgcttct tcaactctgt   1980
agccatcacc gcaaaactcc tacagcagaa gttgaacgtg ggcaaggtcc tcatcgtgga   2040
```

-continued

```
ctgggacatt caccatggca atggcaccca gcaggcgttc tacaatgacc cctctgtgct    2100
ctacatctct ctgcatcgct atgacaacgg gaacttcttt ccaggctctg ggctcctga     2160 agaggttggt ggaggaccag gcgtggggta caatgtgaac gtggcatgga caggaggtgt    2220
ggaccccccc attggagacg tggagtacct tacagccttc aggacagtgg tgatgcccat    2280
tgcccacgag ttctcacctg atgtggtcct agtctccgcc gggtttgatg ctgttgaagg    2340
acatctgtct cctctggggtg ctactctgt caccgccaga tgttttggcc acttgaccag    2400
gcagctgatg accctggcag ggggccgggt ggtgctggcc ctggagggag gccatgactt    2460
gaccgccatc tgtgatgcct ctgaagcttg tgtctcggct ctgctcagtg taaagctgca    2520
gcccttggat gaggcagtct tgcagcaaaa gcccaacatc aacgcagtgg ccacgctaga    2580
gaaagtcatc gagatccaga gcaaacactg gagctgtgtg cagaagttcg ccgctggtct    2640
gggccggtcc ctgcgagggg cccaagcagg tgagaccgaa gaagccgaaa tgtgaacgcc    2700
atggccttgc tgttggtggg ggccgaacag gcccaagctg cggcagcccg ggaacacagc    2760
cccaggccgg cagaggagcc catggagcag gagcctgccc tgtgacgccc cggcccccat    2820
cccctttggg ttcaccattg tgattttgtt tattttttct attaaaaaca aaagttaaa     2880 aattt                                                                2885
```

<210> SEQ ID NO 4
<211> LENGTH: 3876
<212> TYPE: DNA
<213> ORGANISM: Homo sapien

<400> SEQUENCE: 4

```
atgtttgatt acatggattg tgagctgaag ctttctgaat cagttttccg acagctcaac      60
acggccatcg ccgtatccca gatgtcctca ggccagtgcc gcctggcccc cctcatccag     120
gtcatccagg actgcagcca cctctaccac tacacggtca agctcctgtt caagctacac     180
tcttgtctcc ctgcggacac cctgcaaggc cacaggacc ggttccacga gcagtttcac     240
agcctcagga acttcttccg cagagcctcc gacatgctgt acttcaagcg gctcatccag     300 atccccggc tgcccgaggg accccctaac ttcctgcggg cctcagccct ggctgagcac     360
atcaagccgg tggtggtgat ccccgaggag gccccggaag atgaggagcc ggagaatctc     420
attgagatca gcacagggcc ccccgcgggg gagccagtgg tggtggctga cctcttcgat     480
cagacgtttg gacccccaa tgggtctgtg aaggacgaca gggacctcca gattgagagc     540
ttgaagagag aggtggaaat gctccgctct gaactggaga agatcaagct ggaggcccag     600
cggtacatcg cgcagctgaa gagccaggtg aatgcactgg agggtgagct ggaggagcag     660
cggaagcaga agcagaaggc cctggtggat aatgagcagc tccgccacga gctggcccag     720
ctgagggctg cccagctgga gggcgagcgg agccagggcc tgcgtgagga ggctgagagg     780
aaggccagtg ccacggaggc gcgctacaac aagctgaagg aaaagcacag tgagctcgtc     840
catgtgcacg cggagctgct cagaaagaac gcggacacag ccaagcagct gacggtgacg     900
cagcaaagcc aggaggaggt ggcgcgggtg aaggagcagc tggccttcca ggtggagcag     960
gtgaagcggg agtcggagtt gaagctagag gagaagagcg accagctgga aagctcaag    1020 agggagctgg aggccaaggc cggagagctg gcccgcgcgc aggaggccct gagccacaca    1080
gagcagagca gtcggagct gagctcacgg ctggacacgc tgagtgcgga gaaggatgct    1140
ctgagtggag ctgtgcggca gcgggaggca gacctgctgg cggcgcagag cctggtgcgc    1200
```

-continued

```
gagacagagg cggcgctgag ccgggagcag cagcgcagct cccaggagca gggcgagttg    1260
cagggccggc tggcagagag ggagtctcag gagcaggggc tgcggcagag gctgctggac    1320
gagcagttcg cagtgttgcg gggcgctgct gccgaggccg cggcatcct gcaggatgcc     1380 gtgagcaagc tggacgaccc cctgcacctg cgctgtacca gctccccaga ctacctggtg    1440
agcagggccc aggaggcctt ggatgccgtg agcaccctgg aggagggcca cgcccagtac    1500
ctgacctcct tggcagacgc ctccgccctg gtggcagctc tgacccgctt ctcccacctg    1560
gctgcggata ccatcatcaa tggcggtgcc acctcgcacc tggctcccac cgaccctgcc    1620
gaccgcctca tagacacctg cagggagtgc ggggcccggg ctctggagct catggggcag    1680
ctgcaggacc agcaggctct gcggcacatg caggccagcc tggtgcggac acccctgcag    1740
ggcatccttc agctgggcca ggaactgaaa cccaagagcc tagatgtgcg gcaggaggag    1800
ctgggggccg tggtcgacaa ggagatggcg gccacatccg cagccattga agatgctgtg    1860
cggaggattg aggacatgat gaaccaggca cgccacgcca gctcggggt gaagctggag     1920 gtgaacgaga ggatcctcaa ctcctgcaca gacctgatga aggctatccg gctcctggtg    1980
acgacatcca ctagcctgca gaaggagatc gtggagagcg gcaggggggc agccacgcag    2040
caggaatttt acgccaagaa ctcgcgctgg accgaaggcc tcatctcggc ctccaaggct    2100
gtgggctggg gagccacaca gctggtggag gcagctgaca aggtggtgct tcacacgggc    2160
aagtatgagg agctcatcgt ctgctcccac gagatcgcag ccagcacggc ccagctggtg    2220
gcggcctcca aggtgaaggc caacaagcac agccccccacc tgagccgcct gcaggaatgt    2280
tctcgcacag tcaatgagag ggctgccaat gtggtggcct ccaccaagtc aggccaggag    2340
cagattgagg acagagacac catggatttc tccggcctgt ccctcatcaa gctgaagaag    2400
caggagatgg agacgcaggt gcgtgtcctg gagctggaga gacgctggga ggctgaacgc    2460
atgcggctgg gggagttgcg gaagcaacac tacgtgctgg ctggggcatc aggcagccct    2520
ggagaggagg tggccatccg gcccagcact gcccccgaa gtgtaaccac caagaaacca     2580
cccctggccc agaagcccag cgtggccccc agacaggacc accagcttga caaaaaggat    2640
ggcatctacc cagctcaact cgtgaactac taggcccccc aggggtccag cagggtggct    2700
ggtgacaggc ctgggcctct gcaactgccc tgacaggacc gagaggcctt gcccctccac    2760
ctggtgccca agcctcccgc cccaccgtct ggatcaatgt cctcaaggcc cctggcccctt    2820 actgagcctg cagggtcctg ggccatgtgg gtggtgcttc tggatgtgag tctcttattt    2880
atctgcagaa ggaactttgg ggtgcagcca ggacccggta ggcctgagcc tcaactcttc    2940
agaaaatagt gttttttaata ttcctcttca gaaaatagtg ttttttaatat tccgagctag    3000 agctcttctt cctacgtttg tagtcagcac actgggaaac cggccagcg tggggctccc     3060 tgccttctgg actcctgaag gtcgtggatg gatggaaggc acacagcccg tgccggctga    3120
tgggacgagg gtcaggcatc ctgtctgtgg ccttctgggg caccgattct accaggccct    3180
ccagctgcgt ggtctccgca gaccaggctc tgtgtgggct agaggaatgt cgcccattac    3240
tcctcaggcc tggccctcgg gcctccgtga tgggagcccc caggaggggg tcagatgctg    3300 gaagggccg ctttctgggg agtgaggtga gacatagcgg cccaggcgct gccttcactc     3360
ctggagtttc catttccagc tggaatctgc agccaccccc atttcctgtt ttccattccc    3420
ccgttctggc cgcgccccac tgcccacctg aagggtggt ttccagcct ccggagagtg      3480 ggcttggccc taggccctcc agctcagcca gaaaagccc agaaacccag gtgctggacc     3540
agggccctca gggaggggac cctgcggcta gagtgggcta ggccctggct ttgcccgtca    3600
```

-continued

```
gatttgaacg aatgtgtgtc ccttgagccc aaggagagcg gcaggagggg tgggaccagg    3660
ctgggaggac agagccagca gctgccatgc cctcctgctc cccccacccc agccctagcc    3720
cttagccttt tcaccctgtg ctctggaaag gctaccaaat actggccaag gtcaggagga    3780
gcaaaaatga gccagcacca gcgccttggc tttgtgttag catttcctcc tgaagtgttc    3840
tgttggcaat aaaatgcact ttgactgttt gttgtc                              3876
```

<210> SEQ ID NO 5
<211> LENGTH: 2740
<212> TYPE: DNA
<213> ORGANISM: Homo sapien

<400> SEQUENCE: 5

```
gcgaaattga ggtttcttgg tattgcgcgt ttctcttcct tgctgactct ccgaatggcc      60
atggactcgt cgcttcaggc ccgcctgttt cccggtctcg ctatcaagat ccaacgcagt     120
aatggtttaa ttcacagtgc caatgtaagg actgtgaact tggagaaatc ctgtgtttca     180
gtggaatggg cagaaggagg tgccacaaag ggcaaagaga ttgattttga tgatgtggct     240
gcaataaacc cagaactctt acagcttctt cccttacatc cgaaggacaa tctgcccttg     300
caggaaaatg taacaatcca gaaacaaaaa cggagatccg tcaactccaa aattcctgct     360
ccaaaagaaa gtcttcgaag ccgctccact cgcatgtcca ctgtctcaga gcttcgcatc     420
acggctcagg agaatgacat ggaggtggac ctgcctgcag ctgcaaactc ccgcaagcag     480
ttttcagttc ctcctgcccc cactaggcct tcctgccctg cagtggctga ataccattg     540 aggatggtca gcgaggagat ggaagagcaa gtccattcca tccgtggcag ctcttctgca     600
aaccctgtga actcagttcg gaggaaatca tgtcttgtga aggaagtgga aaaaatgaag     660
aacaagcgag aagagaagaa ggcccagaac tctgaaatga aatgaagag agctcaggag     720 tatgacagta gttttccaaa ctgggaattt gcccgaatga ttaaagaatt cgggctact     780 ttggaatgtc atccacttac tatgactgat cctatcgaag agcacagaat atgtgtctgt     840
gttaggaaac gcccactgaa taagcaagaa ttggccaaga agaaaattga tgtgatttcc     900
attcctagca agtgtctcct cttggtacat gaacccaagt tgaaagtgga cttaacaaag     960
tatctggaga accaagcatt ctgctttgac tttgcatttg atgaaacagc ttcgaatgaa    1020
gttgtctaca ggttcacagc aaggccactg gtacagacaa tctttgaagg tggaaaagca    1080 actttgttg catatggcca gacaggaagt ggcaagacac atactatggg cggagacctc    1140
tctgggaaag cccagaatgc atccaagggg atctatgcca tggcctcccg ggacgtcttc    1200
ctcctgaaga tcaaccctg ctaccggaag ttgggcctgg aagtctatgt gacattcttc    1260
gagatctaca atgggaagct gtttgacctg ctcaacaaga aggccaagct gcgcgtgctg    1320
gaggacggca gcaacaggt gcaagtggtg gggctgcagg agcatctggt taactctgct    1380
gatgatgtca tcaagatgct cgacatgggc agcgcctgca gaacctctgg gcagacattt    1440
gccaactcca attcctcccg ctcccacgcg tgcttccaaa ttattcttcg agctaaaggg    1500
agaatgcatg gcaagttctc tttggtagat ctggcaggga atgagcgagg cgcagacact    1560
tccagtgctg accggcagac ccgcatggag ggcgcagaaa tcaacaagag tctcttagcc    1620
ctgaaggagt gcatcagggc cctggacag aacaaggctc acacccgtt ccgtgagagc    1680 aagctgacac aggtgctgag ggactccttc attggggaga actctaggac ttgcatgatt    1740
gccacgatct caccaggcat aagctcctgt gaatatactt taaacaccct gagatatgca    1800
```

```
gacagggtca aggagctgag cccccacagt gggcccagtg gagagcagtt gattcaaatg    1860
gaaacagaag agatggaagc ctgctctaac ggggcgctga ttccaggcaa tttatccaag    1920
gaagaggagg aactgtcttc ccagatgtcc agctttaacg aagccatgac tcagatcagg    1980
gagctggagg agaaggctat ggaagagctc aaggagatca tacagcaagg accagactgg    2040
cttgagctct ctgagatgac cgagcagcca gactatgacc tggagacctt tgtgaacaaa    2100
gcggaatctg ctctggccca gcaagccaag catttctcag ccctgcgaga tgtcatcaag    2160
gccttacgcc tggccatgca gctggaagag caggctagca gacaaataag cagcaagaaa    2220
cggccccagt gacgactgca aataaaaatc tgtttggttt gacacccagc ctcttccctg    2280
gccctcccca gagaactttg ggtacctggt gggtctaggc agggtctgag ctgggacagg    2340
ttctggtaaa tgccaagtat gggggcatct gggcccaggg cagctgggga gggggtcaga    2400
gtgacatggg acactccttt tctgttcctc agttgtcgcc ctcacgagag gaaggagctc    2460
ttagttaccc ttttgtgttg cccttctttc catcaagggg aatgttctca gcatagagct    2520
ttctccgcag catcctgcct gcgtggactg gctgctaatg gagagctccc tggggttgtc    2580
ctggctctgg ggagagagac ggagcccttta gtacagctat ctgctggctc taaaccttct    2640
acgcctttgg gccgagcact gaatgtcttg tactttaaaa aaatgtttct gagacctctt    2700
tctactttac tgtctcccta gagtcctaga ggatccctac                         2740

<210> SEQ ID NO 6
<211> LENGTH: 2569
<212> TYPE: DNA
<213> ORGANISM: Homo sapien
<220> FEATURE:
<221> NAME/KEY: Unsure
<222> LOCATION: (2237)..(2237)
<223> OTHER INFORMATION: n = a, c, g,  or t/u
<220> FEATURE:
<221> NAME/KEY: Unsure
<222> LOCATION: (2260)..(2260)
<223> OTHER INFORMATION: n = a, c, g,  or t/u
<220> FEATURE:
<221> NAME/KEY: Unsure
<222> LOCATION: (2305)..(2305)
<223> OTHER INFORMATION: n = a, c, g,  or t/u
<220> FEATURE:
<221> NAME/KEY: Unsure
<222> LOCATION: (2315)..(2315)
<223> OTHER INFORMATION: n = a, c, g,  or t/u
<220> FEATURE:
<221> NAME/KEY: Unsure
<222> LOCATION: (2355)..(2355)
<223> OTHER INFORMATION: n = a, c, g,  or t/u
<220> FEATURE:
<221> NAME/KEY: Unsure
<222> LOCATION: (2420)..(2420)
<223> OTHER INFORMATION: n = a, c, g,  or t/u
<220> FEATURE:
<221> NAME/KEY: Unsure
<222> LOCATION: (2421)..(2421)
<223> OTHER INFORMATION: n = a, c, g,  or t/u
<220> FEATURE:
<221> NAME/KEY: Unsure
<222> LOCATION: (2423)..(2423)
<223> OTHER INFORMATION: n = a, c, g,  or t/u
<220> FEATURE:
<221> NAME/KEY: Unsure
<222> LOCATION: (2490)..(2490)
<223> OTHER INFORMATION: n = a, c, g,  or t/u
<220> FEATURE:
<221> NAME/KEY: Unsure
<222> LOCATION: (2523)..(2523)
<223> OTHER INFORMATION: n = a, c, g,  or t/u

<400> SEQUENCE: 6
```

```
aagagtaaaa gctactcttt cagagagaaa aataggagat tcatgtgaca aagatttgcc      60
tctgaaattt tgtgagttcc cacagaagac tataatgcct ggatttaaaa caactgtata     120
tgtttctcat ataaatgacc tttcagactt ttatgttcaa ctaatagaag atgaagctga     180
aattagtcat ctttcagaga gattaaacag tgttaaaaca aggcccgaat attatgtagg     240
tccacctttg caaagaggag atatgatatg tgctgttttc ccagaagata atttatggta     300
tcgtgctgtg atcaaggagc aacaacccaa tgaccttctc tctgtgcagt ttatagatta     360
tggcaatgtt tctgtggttc atactaacaa aataggtagg cttgacctttg ttaatgcaat     420
attgccgggg ttgtgcattc attgctcctt gcagggattt gaggttcctg acaataaaaa     480
ttctaagaaa atgatgcatt actttttccca acggaccagc gaggctgcaa taagatgtga     540
atttgttaaa tttcaagaca gatgggaagt tattcttgct gatgaacatg ggatcatagc     600
agatgatatg attagcaggt atgctctcag tgaaaaatct caagtagaac tttctaccca     660
agtaattaaa agtgccagtt caaagtctgt taacaaatca gacattgaca cttcagtatt     720
tcttaactgg tataatccag aaaaaaaaat gataagagct tatgccactg tgatagatgg     780
acctgagtac ttttggtgtc agtttgctga tacggagaaa cttcagtgtt tagaagtaga     840
agtacagact gctggagaac aggtagcaga caggagaaat tgtatcccat gtccttatat     900
tggagatcct tgtatagtaa gatacagaga agatggacat tattataggg cacttatcac     960
taatatttgt gaagattatc ttgtatctgt caggcttgtg gactttggaa acattgaaga    1020
ctgtgtggac ccaaaagcac tctgggccat tccttctgaa cttctgtcgg ttcccatgca    1080
agcctttcca tgttgcctct cagggtttaa catttcagaa ggattatgtt ctcaagaggg    1140
aaatgactat ttctatgaaa taataacaga agatgtgttg gaataacaa tactagaaat     1200
cagaagggat gtttgtgata tccctttagc aattgttgac ttgaaaagca aggtaaaag    1260
tattaatgag aaaatggaga atattctaa gactggtatt aaaagtgctc ttccctatga     1320
aaatattgac tcagagataa agcagactct tgggtcctac aatcttgatg taggacttaa    1380
gaaattaagt aataaagctg tacaaaataa aatatatatg gaacaacaga cagatgagct    1440
tgctgaaata actgaaaaag atgtaaacat tattggaacc aaaccaagta acttccgtga    1500
ccctaaaaact gataacattt gtgaagggtt tgaaaccccc tgcaaagata aaattgatac    1560
tgaggaactg gaaggtgaat tagagtgcca tctggttgac aaagcagagt ttgatgataa    1620
ataccctgatt acaggattta acacattact accacatgct aatgaaacaa aggagatact    1680
agaactgaat tcacttgagg tgccgctttc tcctgatgat gaatcaaaag aattcttaga    1740
actgaatct attgagttac agaattctct ggtggtggat gaagaaaaag gggagctaag    1800
cccggtgcca ccgaatgtgc cactctccca agagtgtgtc acaaaaggcg ccatggagct    1860
atttacactg cagcttcctc tcagctgtga agctgagaaa cagccagaac tagaactacc    1920
tacagcccag ctgcctttag atgacaagat ggatcctttg tctttaggag ttagtcagaa    1980
agcacaggaa tccatgtgta ctgaggacat gagaaagtca agttgtgtag aatcttttga    2040
tgaccagcgc aggatgtcat tgcatctaca tggagcagat tgtgatccta aaacacagaa    2100
tgaaatgaat atatgtgaag aagaatttgt agagtataaa aacagggatg ccatttcggc    2160
attgatgcct ttttctctga ggaagaaagc agtgatggaa gcaagcacaa taatggttta    2220
ccagatcata tttcagntca attacagaac acctacactn tgaaagcctt tactgttgga    2280
tctaaatgtg ttgtgtggtc aagtntaaga aacanatggt ctaaatgtga gattttagaa    2340
```

-continued

```
acagctgaag aaggnacaag ggttttgaac ctttcaaatg gtatggagga gatagtgaac    2400
cctgagaatg tctggaatgn nanacccaaa ttggataaga gtccacctga gaaaaggggt    2460
ttggaggtga tggagattta accgtggatn tatagctgtg gccaatcagt cagaagctgc    2520
ccntgaacaa gtggcatctt acgcagacca acagagtatt tgagaaaat              2569
```

<210> SEQ ID NO 7
<211> LENGTH: 1997
<212> TYPE: DNA
<213> ORGANISM: Homo sapien
<220> FEATURE:
<221> NAME/KEY: Unsure
<222> LOCATION: (105)..(105)
<223> OTHER INFORMATION: n = a, g, c, or t/u
<220> FEATURE:
<221> NAME/KEY: Unsure
<222> LOCATION: (132)..(132)
<223> OTHER INFORMATION: n = a, g, c, or t/u
<220> FEATURE:
<221> NAME/KEY: Unsure
<222> LOCATION: (151)..(151)
<223> OTHER INFORMATION: n = a, g, c, or t/u
<220> FEATURE:
<221> NAME/KEY: Unsure
<222> LOCATION: (209)..(209)
<223> OTHER INFORMATION: n = a, g, c, or t/u
<220> FEATURE:
<221> NAME/KEY: Unsure
<222> LOCATION: (221)..(221)
<223> OTHER INFORMATION: n = a, g, c, or t/u
<220> FEATURE:
<221> NAME/KEY: Unsure
<222> LOCATION: (462)..(462)
<223> OTHER INFORMATION: n = a, g, c, or t/u
<220> FEATURE:
<221> NAME/KEY: Unsure
<222> LOCATION: (542)..(542)
<223> OTHER INFORMATION: n = a, g, c, or t/u
<220> FEATURE:
<221> NAME/KEY: Unsure
<222> LOCATION: (625)..(625)
<223> OTHER INFORMATION: n = a, g, c, or t/u
<220> FEATURE:
<221> NAME/KEY: Unsure
<222> LOCATION: (642)..(642)
<223> OTHER INFORMATION: n = a, g, c, or t/u
<220> FEATURE:
<221> NAME/KEY: Unsure
<222> LOCATION: (659)..(659)
<223> OTHER INFORMATION: n = a, g, c, or t/u
<220> FEATURE:
<221> NAME/KEY: Unsure
<222> LOCATION: (663)..(663)
<223> OTHER INFORMATION: n = a, g, c, or t/u
<220> FEATURE:
<221> NAME/KEY: Unsure
<222> LOCATION: (666)..(666)
<223> OTHER INFORMATION: n = a, g, c, or t/u
<220> FEATURE:
<221> NAME/KEY: Unsure
<222> LOCATION: (672)..(672)
<223> OTHER INFORMATION: n = a, g, c, or t/u
<220> FEATURE:
<221> NAME/KEY: Unsure
<222> LOCATION: (675)..(675)
<223> OTHER INFORMATION: n = a, g, c, or t/u
<220> FEATURE:
<221> NAME/KEY: Unsure
<222> LOCATION: (686)..(686)
<223> OTHER INFORMATION: n = a, g, c, or t/u
<220> FEATURE:
<221> NAME/KEY: Unsure
<222> LOCATION: (693)..(693)
<223> OTHER INFORMATION: n = a, g, c, or t/u
<220> FEATURE:
<221> NAME/KEY: Unsure

```
<222> LOCATION: (695)..(695)
<223> OTHER INFORMATION: n = a, g, c, or t/u
<220> FEATURE:
<221> NAME/KEY: Unsure
<222> LOCATION: (724)..(724)
<223> OTHER INFORMATION: n = a, g, c, or t/u
<220> FEATURE:
<221> NAME/KEY: Unsure
<222> LOCATION: (778)..(778)
<223> OTHER INFORMATION: n = a, g, c, or t/u
<220> FEATURE:
<221> NAME/KEY: Unsure
<222> LOCATION: (872)..(872)
<223> OTHER INFORMATION: n = a, g, c, or t/u
<220> FEATURE:
<221> NAME/KEY: Unsure
<222> LOCATION: (979)..(979)
<223> OTHER INFORMATION: n = a, g, c, or t/u
<220> FEATURE:
<221> NAME/KEY: Unsure
<222> LOCATION: (1146)..(1146)
<223> OTHER INFORMATION: n = a, g, c, or t/u
<220> FEATURE:
<221> NAME/KEY: Unsure
<222> LOCATION: (1609)..(1609)
<223> OTHER INFORMATION: n = a, g, c, or t/u
<220> FEATURE:
<221> NAME/KEY: Unsure
<222> LOCATION: (1875)..(1875)
<223> OTHER INFORMATION: n = a, g, c, or t/u

<400> SEQUENCE: 7
gggctgggga agatggcggt ggctggggcg gtgtccgggg agccgctggt gcactggtgc      60
acccagcagt tgcggaagac tttcggcctg gatgtcagcg agganatcat tcagtacgtt     120
ttgtcaattg anagtgctga agagatacga naatatgtta ctgatctcct ccaggggaaa     180
tgaaggcaaa aaaggtcaat tcatacaana acttataacc naatggcaaa agaatgatca     240
ggagttgatt tcggatcctt tgcagcagtg cttcaaaaaa gatgaaattt tagatgggca     300
gaaatcaggc gaccatctaa agcggggtat gaagaaaggg agaaacagac aggaagttcc     360
tgcatttact gaacctgaca cgactgcaga ggttaaaaca cttttgattg ccaaggcac      420 aagagaacag caactccgta aagaagaaga caaagtttgt cnatttatac acaagagagg     480
gacaggacag gcttgcagtc ctgctccctg gtcgtcaccc ttgtgattgc ctgggccaga     540
ancacaagct catcaataac tgtctgatct gtgggcgcat tgtctgtgaa caagaaggct     600
caggcccttg cttattctgt ggcantctgg tgtgtactct tnaggaacaa gatattttnc     660
agngtnactc anacnaaagc cagaanctgc tananaaact catgtcagga gtggacaatt     720
ctgnaaatgt ggacatctct accaaggacc ttcttcctca tcaagaattg cgaattangt     780
ctggtctgga gaaggctatc aagcataaag acaaactgtt agagtttgac agaactagta     840
ttcgaaggac ccaagtcatt gatgatgagt cngattactt tgccagtgat tctaaccaat     900
ggttgtccaa acttgagcgg gaaaccttgc agaagcgaga ggaggagctg agagaacttc     960
gacacgcctc tcgactttnt aagaagttca ccattgactt tgcaggaagg aagatcctgg    1020
aagaagaaaa ttcactagca gagtatcata gcagactaga tgagcaata caggccattg    1080 ccaatggaac cttgaaccag ccactgacca aattggatag atcttctgaa gagcctttgg    1140
gagttntggt aaatcccaac atgtaccagt cccctcccca gtgggttgac cacacaggtg    1200
cagcctcaca gaagaaggct ttccgttctt caggatttgg actagagttc aactcatttc    1260
agcaccagct gcgaatccag gatcaagaat tcaggaagg cttttgatggt ggctggtgcc    1320 tctctgtaca tcagccctgg gcttctctgc ttgtcagagg gattaaaagg gtggagggca    1380
```

-continued

```
gatcctggta cacccccac agaggacgac tttggatagc agccacagct aaaaaacccct      1440 cccctcaaga agtctcagaa ctccaggcta catatcgtct tcttcgtggg aaagatgtgg      1500
aatttcctaa tgactatccg tcaggttgtc ttctgggctg tgtggaccta attgactgct      1560
tgtcccagaa gcaatttaag gagcagtttc cagacatcag tcaagaatnt gattctccat      1620
ttgttttcat ctgcaaaaat cctcaggaaa tggttgtgaa gtttcctatt aaggaaatc       1680 caaaatctg gaaattggat ccaagatcc atcaaggagc aaagaagggg ttaatgaagc         1740
agaataaagc tgtctgaccc aggagaaaag gaactataca gcatagtgga gttttgtgta      1800
ctaaaattgc tatctactgg tcctttggaa ttgaagtagt agaaacctaa aggcttggcg      1860
tcaggcttga atatntcaga acttaaactc ttaccaaaat ctgtatattt ttcttaagga      1920
gtgggattcc tactttatgt aatggggtcg aaatctttga acacattatt tataaaaacc      1980
tgtttaaaaa ttctaaa                                                    1997

<210> SEQ ID NO 8
<211> LENGTH: 1087
<212> TYPE: DNA
<213> ORGANISM: Homo sapien

<400> SEQUENCE: 8
aagatgatgc ctagtaaatt acagaagaac aaacagagac tgcgaaacga tcctctcaat       60
caaaataagg gtaaaccaga cttgaataca acattgccaa ttagacaaac agcatcaatt      120
ttcaaacaac cggtaaccaa agtcacaaat catcctagta ataaagtgaa atcagaccca      180
caacgaatga atgaacagcc acgtcagctt ttctgggaga agaggctaca aggacttagt      240
gcatcagatg taacagaaca aattataaaa accatggaac tacccaaagg tcttcaagga      300
gttggtccag gtagcaatga tgagacccct ttatctgctg ttgccagtgc tttgcacaca      360
agctctgcgc caatcacagg gcaagtctcc gctgctgtgg aaaagaaccc tgctgttggg      420
cttaacacat ctcaaccct ctgcaaagct tttattgtca cagatgaaga catcaggaaa       480
caggaagagc gagtacagca agtacgcaag aaattggaag aagcactgat ggcagacatc      540
ttgtcgcgag ctgctgatac agaagagatg gatattgaaa tggacagtgg agatgaagcc      600
taagaatatg atcaggtaac tttcgaccga cttccccaa gagaaaattc ctagaaattg        660
aacaaaaatg tttccactgg cttttgcctg taagaaaaaa aatgtacccg agcacataga      720
gctttttaat agcactaacc aatgccttt tagatgtatt tttgatgtat atatctatta       780
ttcaaaaaat catgtttatt ttgagtccta ggacttaaaa ttagtctttt gtaatatcaa      840
gcaggaccct aagatgaagc tgagcttttg atgccaggtg caatttactg gaaatgtagc      900
acttacgtaa acatttgtt tcccccacag ttttaataag aacagatcag gaattctaaa       960
taaatttccc agttaaagat tattgtgact tcactgtata taaacatatt tttatacttt     1020
attgaaaggg gacacctgta cattcttcca tcgtcactgt aaagacaaat aaatgattat     1080
attcaca                                                               1087

<210> SEQ ID NO 9
<211> LENGTH: 1760
<212> TYPE: DNA
<213> ORGANISM: Homo sapien

<400> SEQUENCE: 9 gtcgacccctt tccacccctg gaagatggaa ataaacctgc gtgtgggtgg agtgttagga      60
caaaaaaaaa aaaaaaaaag tctagagcca ccgtccaggg agcaggtagc tgctgggctc     120
```

-continued

```
cggggacact tgcgttcgg gctgggagcg tgctttccac gacggtgaca cgcttccctg        180
gattggcagc cagactgcct tccgggtcac tgccatggag gagccgcagt cagatcctag        240
cgtcgagccc cctctgagtc aggaaacatt ttcagaccta tggaaactac ttcctgaaaa        300
caacgttctg tcccccttgc cgtcccaagc aatggatgat ttgatgctgt ccccggacga        360
tattgaacaa tggttcactg aagacccagg tccagatgaa gctcccagaa tgccagaggc        420
tgctcccccc gtggcccctg caccagcagc tcctacaccg gcggccctg caccagcccc         480 ctcctggccc ctgtcatctt ctgtcccttc cagaaaacc taccagggca gctacggttt         540
ccgtctgggc ttcttgcatt ctgggacagc caagtctgtg acttgcacgt actcccctgc        600
cctcaacaag atgttttgcc aactggccaa gacctgccct gtgcagctgt gggttgattc        660 cacaccccg cccggcaccc cgtccgcgc catggccatc tacaagcagt cacagcacat         720
gacggaggtt gtgaggcgct gccccccacca tgagcgctgc tcagatagcg atggtctggc       780
ccctcctcag catcttatcc gagtggaagg aaatttgcgt gtggagtatt tggatgacag        840
aaacactttt cgacatagtg tggtggtgcc ctgtgagccg cctgaggttg gctctgactg        900
taccaccatc cactacaact acatgtgtaa cagttcctgc atgggcggca tgaaccggag        960
gcccatcctc accatcatca cactggaaga ctccagtggt aatctactgg gacgaaacag       1020
ctttgaggtg catgtttgtg cctgtcctgg gagagaccgg cgcacagagg aagagaatct       1080
ccgcaagaaa ggggagcctc accacgagct gccccccaggg agcactaagc gagcactgcc       1140
caacaacacc agctcctctc cccagccaaa gaagaaacca ctggatggag aatatttcac       1200
ccttcagatc cgtgggcgtg agcgcttcga gatgttccga gagctgaatg aggccttgga       1260
actcaaggat gcccaggctg ggaaggagcc agggggggagc agggctcact ccagccacct       1320
gaagtccaaa aagggtcagt ctacctcccg ccataaaaaa ctcatgttca agacagaagg       1380
gcctgactca gactgacatt ctccacttct tgttccccac tgacagcctc ccaccccat        1440 ctctccctcc cctgccattt tgggttttgg gtctttgaac ccttgcttgc aataggtgtg       1500
cgtcagaagc acccaggact tccatttgct ttgtcccggg gctccactga caagttggc        1560 ctgcactggt gttttgttgt ggggaggagg atggggagta ggacatacca gcttagattt       1620
taaggttttt actgtgaggg atgtttggga gatgtaagaa atgttcttgc agttaagggt       1680
tagtttacaa tcagccacat tctaggtagg gacccacttc accgtactaa ccagggaagc       1740
tgtccctcac tgttgaattc                                                    1760
```

<210> SEQ ID NO 10
<211> LENGTH: 1953
<212> TYPE: DNA
<213> ORGANISM: Homo sapien

<400> SEQUENCE: 10

```
acgcctgcca ggagcaagcc gaagagccag ccggccggcg cactccgact ccgagcagtc         60
tctgtccttc gacccgagcc ccgcgcccctt tccgggaccc ctgccccgcg ggcagcgctg        120
ccaacctgcc ggccatggag acccccgtccc agcggcgcgc caccccgcagc ggggcgcagg      180 ccagctccac tccgctgtcg cccacccgca tcacccggct gcaggagaag gaggacctgc        240
aggagctcaa tgatcgcttg gcggtctaca tcgaccgtgt gcgctcgctg gaaacggaga        300
acgcagggct gcgccttcgc atcaccgagt ctgaagaggt ggtcagccgc gaggtgtccg        360
gcatcaaggc cgcctacgag gccgagctcg gggatgcccg caagacccctt gactcagtag      420
```

-continued

```
ccaaggagcg cgcccgcctg cagctggagc tgagcaaagt gcgtgaggag tttaaggagc    480
tgaaagcgcg caataccaag aaggagggtg acctgatagc tgctcaggct cggctgaagg    540
acctggaggc tctgctgaac tccaaggagg ccgcactgag cactgctctc agtgagaagc    600
gcacgctgga gggcgagctg catgatctgc ggggccaggt ggccaagctt gaggcagccc    660
taggtgaggc caagaagcaa cttcaggatg agatgctgcg gcgggtggat gctgagaaca    720
ggctgcagac catgaaggag gaactggact tccagaagaa catctacagt gaggagctgc    780
gtgagaccaa gcgccgtcat gagacccgac tggtggagat tgacaatggg aagcagcgtg    840
agtttgagag ccggctggcg gatgcgctgc aggaactgcg ggcccagcat gaggaccagg    900
tggagcagta taagaaggag ctggagaaga cttattctgc caagctggac aatgccaggc    960
agtctgctga ggaacagcag aacctggtgg gggctgccca cgaggagctg cagcagtcgc   1020
gcatccgcat cgacagcctc tctgcccagc tcagccagct ccagaagcag ctggcagcca   1080
aggaggcgaa gcttcgagac ctggaggact cactggcccg tgagcgggac accagccggc   1140
ggctgctggc ggaaaaggag cgggagatgg ccgagatgcg ggcaaggatg cagcagcagc   1200
tggacgagta ccaggagctt ctggacatca agctggccct ggacatggag atccacgcct   1260
accgcaagct cttggagggc gaggaggaga ggctacgcct gtcccccagc cctacctcgc   1320
agcgcagccg tggccgtgct tcctctcact catcccagac acaggtgggg ggcagcgtca   1380
ccaaaaagcg caaactggag tccactgaga gccgcagcag cttctcacag cacgcacgca   1440
ctagcgggcg cgtggccgtg gaggaggtgg atgaggaggg caagtttgtc cggctgcgca   1500
acaagtccaa tgaggaccag tccatgggca attggcagat caagcgccag aatggagatg   1560
atcccttgct gacttaccgg ttcccaccaa agttcaccct gaaggctggg caggtggtga   1620
cgatctgggc tgcaggagct ggggccaccc acagccccc taccgacctg gtgtggaagg   1680
cacagaacac ctggggctgc gggaacagcc tgcgtacggc tctcatcaac tccactgggg   1740
aagaagtggc catgcgcaag ctggtgcgct cagtgactgt ggttgaggac gacgaggatg   1800
aggatggaga tgacctgctc catcaccacc acgtgagtgg tagccgccgc tgaggccgag   1860
cctgcactgg ggccaccagc caggcctggg ggcagcctct ccccagcctc cccgtgccaa   1920
aaatcttttc attaaagaat gttttggaac ttt                                1953
```

<210> SEQ ID NO 11
<211> LENGTH: 6018
<212> TYPE: DNA
<213> ORGANISM: Homo sapien

<400> SEQUENCE: 11

```
gctgcctccg ccgccgcggg gcagccgggg ggcagggagc ccagcgaggg gcgcgcgtgg     60
gcgcggccat gggactgcgc cggatccggt gacagcaggg agccaagcgg cccgggccct    120
gagcgcgtct tctccggggg gcctcgccct cctgctcgcg gggccgggc tcctgctccg    180
gttgctggcg ctgttgctgg ctgtggcggc ggccaggatc atgtcgggtc gccgctgcgc    240
cggcggggga gcggcctgcg cgagcgccgc ggccgaggcc gtggagccgg ccgcccgaga    300
gctgttcgag gcgtgccgca acggggacgt ggaacgagtc aagaggctgg tgacgcctga    360
gaaggtgaac agccgcgaca cggcgggcag gaaatccacc ccgctgcact cgccgcaggg    420
ttttgggcgg aaagacgtag ttgaatattt gcttcagaat ggtgcaaatg tccaagcacg    480
tgatgatggg ggccttattc ctcttcataa tgcatgctct tttggtcatg ctgaagtagt    540
caatctcctt ttgcgacatg gtgcagaccc caatgctcga gataattgga attatactcc    600
```

-continued

```
tctccatgaa gctgcaatta aaggaaagat tgatgtttgc attgtgctgt tacagcatgg      660
agctgagcca accatccgaa atacagatgg aaggacagca ttggatttag cagatccatc      720
tgccaaagca gtgcttactg gtgaatataa gaaagatgaa ctcttagaaa gtgccaggag      780
tggcaatgaa gaaaaaatga tggctctact cacaccatta aatgtcaact gccacgcaag      840
tgatggcaga aagtcaactc cattacattt ggcagcagga tataacagag taaagattgt      900
acagctgtta ctgcaacatg gagctgatgt ccatgctaaa gataaaggtg atctggtacc      960
attacacaat gcctgttctt atggtcatta tgaagtaact gaacttttgg tcaagcatgg     1020
tgcctgtgta aatgcaatgg acttgtggca attcactcct cttcatgagg cagcttctaa     1080
gaacagggtt gaagtatgtt ctcttctctt aagttatggt gcagacccaa cactgctcaa     1140
ttgtcacaat aaaagtgcta tagacttggc tcccacacca cagttaaaag aaagattagc     1200
atatgaattt aaaggccact cgttgctgca agctgcacga gaagctgatg ttactcgaat     1260
caaaaaacat ctctctctgg aaatggtgaa tttcaagcat cctcaaacac atgaaacagc     1320
attgcattgt gctgctgcat ctccatatcc caaagaaag caaatatgtg aactgttgct      1380
aagaaaagga gcaaacatca atgaaaagac taaagaattc ttgactcctc tgcacgtggc     1440
atctgagaaa gctcataatg atgttgttga agtagtggtg aaacatgaag caaaggttaa     1500
tgctctggat aatcttggtc agacttctct acacagagct gcatattgtg gtcatctaca     1560
aacctgccgc ctactcctga gctatgggtg tgatcctaac attatatccc ttcagggctt     1620
tactgcttta cagatgggaa atgaaaatgt acagcaactc ctccaagagg gtatctcatt     1680
aggtaattca gaggcagaca gacaattgct ggaagctgca aaggctggag atgtcgaaac     1740
tgtaaaaaaa ctgtgtactg ttcagagtgt caactgcaga gacattgaag ggcgtcagtc     1800
tacaccactt cattttgcag ctgggtataa cagagtgtcc gtggtggaat atctgctaca     1860
gcatggagct gatgtgcatg ctaaagataa aggaggcctt gtacctttgc acaatgcatg     1920
ttcttatgga cattatgaag ttgcagaact tcttgttaaa catggagcag tagttaatgt     1980
agctgattta tggaaattta ccctttaca tgaagcagca gcaaaaggaa aatatgaaat      2040
ttgcaaactt ctgctccagc atggtgcaga ccctacaaaa aaaacagggg atggaaatac     2100 tccttttggat cttgttaaag atggagatac agatattcaa gatctgctta ggggagatgc     2160
agctttgcta gatgctgcca agaagggttg tttagccaga gtgaagaagt tgtcttctcc     2220
tgataatgta aattgccgcg atacccaagg cagacattca acacctttac atttagcagc     2280
tggttataat aatttagaag ttgcagagta tttgttacaa cacggagctg atgtgaatgc     2340
ccaagacaaa ggaggactta ttcctttaca taatgcagca tcttacgggc atgtagatgt     2400
agcagctcta ctaataaagt ataatgcatg tgtcaatgcc acggacaaat gggctttcac     2460 accttttgcac gaagcagccc aaaagggacg aacacagctt tgtgctttgt tgctagccca     2520
tggagctgac ccgactctta aaaatcagga aggacaaaca cctttagatt tagttttcagc    2580 agatgatgtc agcgctcttc tgacagcagc catgccccca tctgctctgc cctcttgtta     2640
caagcctcaa gtgctcaatg gtgtgagaag cccaggagcc actgcagatg ctctctcttc     2700
aggtccatct agcccatcaa gcctttctgc agccagcagt cttgacaact tatctgggag     2760 ttttttcagaa ctgtcttcag tagttagttc aagtggaaca gagggtgctt ccagtttgga    2820
gaaaaaggag gttccaggag tagattttag cataactcaa ttcgtaagga atcttggact     2880
tgagcaccta atggatatat ttgagagaga acagatcact ttggatgtat tagttgagat     2940
```

```
ggggcacaag gagctgaagg agattggaat caatgcttat ggacataggc acaaactaat    3000
taaaggagtc gagagactta tctccggaca acaaggtctt aacccatatt aactttgaa    3060 cacctctggt agtggaacaa ttcttataga tctgtctcct gatgataaag agtttcagtc    3120
tgtggaggaa gagatgcaaa gtacagttcg agagcacaga gatggaggtc atgcaggtgg    3180
aatcttcaac agatacaata ttctcaagat tcagaaggtt tgtaacaaga aactatggga    3240
aagatacact caccggagaa aagaagtttc tgaagaaaac cacaaccatg ccaatgaacg    3300
aatgctattt catgggtctc cttttgtgaa tgcaattatc cacaaaggct ttgatgaaag    3360
gcatgcgtac ataggtggta tgtttggagc tggcatttat tttgctgaaa actcttccaa    3420
aagcaatcaa tatgtatatg gaattggagg aggtactggg tgtccagttc acaaagacag    3480
atcttgttac atttgccaca ggcagctgct cttttgccgg gtaaccttgg gaaagtcttt    3540
cctgcagttc agtgcaatga aaatggcaca ttctcctcca ggtcatcact cagtcactgg    3600
taggcccagt gtaaatggcc tagcattagc tgaatatgtt atttacagag gagaacaggc    3660
ttatcctgag tatttaatta cttaccagat tatgaggcct gaaggtatgg tcgatggata    3720
aatagttatt ttaagaaact aattccactg aacctaaaat catcaaagca gcagtggcct    3780
ctacgtttta ctcctttgct gaaaaaaaat catcttgccc acaggcctgt ggcaaaagga    3840
taaaaatgtg aacgaagttt aacattctga cttgataaag cttaataat gtacagtgtt    3900 ttctaaatat ttcctgtttt ttcagcactt taacagatgc cattccaggt taaactgggt    3960
tgtctgtact aaattataaa cagagttaac ttgaaccttt tatatgttat gcattgattc    4020
taacaaactg taatgccctc aacagaacta attttactaa tacaatactg tgttctttaa    4080
aacacagcat ttcactgaa tacaatttca tttgtaaaac tgtaaataag agcttttgta    4140
ctagcccagt atttatttac attgctttgt aatataaatc tgttttagaa ctgcagcggt    4200
ttacaaaatt ttttcatatg tattgttcat ctatacttca tcttcatcg tcatgattga    4260 gtgatctta catttgattc cagaggctat gttcagttgt tagttgggaa agattgagtt    4320
atcagattta atttgccgat gggagccttt atctgtcatt agaaatcttt ctcatttaag    4380
aacttatgaa tatgctgaag atttaatttg tgataccttt gtatgtatga gacacattcc    4440
aaagagctct aactatgata ggtcctgatt actaaagaag cttctttact ggcctcaatt    4500
tctagctttc atgttggaaa attttctgca gtccttctgt gaaaattaga gcaaagtgct    4560
cctgtttttt agagaaacta atcttgctg ttgaacaatt attgtgttct tttcatggaa    4620
cataagtagg atgttaacat ttccagggtg ggaagggtaa tcctaaatca tttcccaatc    4680
tattctaatt accttaaatc taaagggaa aaaaaaatc acaaacagga ctgggtagtt    4740
ttttatccta agtatatttt ttcctgttct ttttacttgg ttttattgct gtatttatag    4800
ccaatctata catcatgggt aaacttaacc cagaactata aaatgtagtt gtttcagtcc    4860
ccttcaggcc tcctgaatgg gcaagtgcag tgaaacaggt gcttcctgct cctgggtttt    4920
ctctccatga tgttatgccc aattggaaat atgctgtcag tttgtgcacc atatggtgac    4980
cacgcctgtg ctcagtttgg cagctataga aggaaatgct gtcccataaa atgccatccc    5040
tatttctaat ataacactct tttccaggaa gcatgcttaa gcatcttgtt acagagacat    5100
acatccatta tggcttggca atctctttta tttgttgact ctagctccct tcaaagtcga    5160
ggaaagatct ttactcactt aatgaggaca ttccccatca ctgtctgtac cagttcacct    5220
ttattttacg ttttattcag tctgtaaatt aactggccct ttgcagtaac ttgtacataa    5280
agtgctagaa aatcatgttc cttgtcctga gtaagagtta atcagagtaa gtgcatttct    5340
```

```
ggagttgttt ctgtgatgta aattatgatc attatttaag aagtcaaatc ctgatcttga    5400
agtgcttttt atacagctct ctaataatta caaatatccg aaagtcattt cttggaacac    5460
aagtggagta tgccaaattt tatatgaatt tttcagatta tctaagcttc caggttttat    5520
aattagaaga taatgagaga attaatgggg tttatattta cattatctct caactatgta    5580
gcccatatta ctcaccctat gagtgaatct ggaattgctt ttcatgtgaa atcattgtgg    5640
tctatgagtt tacaatactg caaactgtgt tattttatct aaaccattgc ttaatgagtg    5700
tgttttccca tgaatgaata taccgtggtt catatgttag catggcagca ttttcagata    5760 gcttttgtt tgttgggaag ttggggtttt ggggggaggg ggagtattag tacgttgcat     5820
ggaatagcct actttataat gatgggaatg cttttctttt tgttttggga ttttttttt     5880 tgaagtgaaa tttaactttt tgtgccagta gtactattat acccatcttc agtgtcttac    5940
ttgtactgta tcaaattcca taccctcatt taattcttaa taaaactgtt cacttgtaaa    6000
aaaaaaaaaa aaaaaaaa                                                  6018

<210> SEQ ID NO 12
<211> LENGTH: 2039
<212> TYPE: DNA
<213> ORGANISM: Homo sapien

<400> SEQUENCE: 12
ccacatccag aagcaaaagc acttcaatga gcgagaagcc agccgagtgg tgcgggacgt      60
tgctgctgcc cttgacttcc tgcataccaa aggcattgct catcgtgatc tgaaaccaga    120
aaatatattg tgtgaatctc cagaaaaggt gtctccagtg aaaatctgtg actttgactt    180
gggcagtggg atgaaactga caactcctg taccccata accacaccag agctgaccac      240
cccatgtggc tctgcagaat acatggcccc tgaggtagtg gaggtcttca cggaccaggc    300
cacattctac gacaagcgct gtgacctgtg agcctgggc gtggtcctct acatcatgct     360
gagtggctac ccacccttcg tgggtcactg cggggccgac tgtggctggg accggggcga    420
ggtctgcagg gtgtgccaga acaagctgtt tgaaagcatc caggaaggca gtatgagtt     480 tcctgacaag gactgggcac acatctccag tgaagccaaa gacctcatct ccaagctcct    540
ggtgcgagat gcaaagcaga aacttagcgc cgcccaagtt ctgcagcacc catgggtgca    600
ggggcaagct ccagaaaagg gactccccac gccgcaagtc ctccagagga acagcagcac    660
aatggacctg acgctcttcg cagctgaggc catcgccctt aaccgccagc tatctcagca    720
cgaagagaac gaactagcag aggagccaga ggcactagct gatggcctct gctccatgaa    780
gctttcccct ccctgcaagt cacgcctggc ccggagacgg gccctggccc aggcaggccg    840
tggtgaaaac aggagcccgc ccacagcact ctgaaatgct ccagtcacac cttataggcc    900
ctaggcctgg ccaggcattg tcccctggaa acctgtgtgg ctaaagtctg ctgagcaggc    960
agcagcctct gctctgtggc tccattcagg cttttctcatc tacgaaggcc ctgaggttcc   1020
catcaacccc catttcccta gggtcctgga ggaaaaagct tttccaaag gggttgtctt    1080 tgaaaaggaa agcaatcact tctcactttg cataattgcc tgcagcagga acatctcttc    1140
actgggctcc acctgctcac ccgcctgcag atctgggatc cagcctgctc tcaccgctgt    1200
agctgtggcg gctggggctg cagcctgcag ggagaagcaa gaagcatcag ttgacagagg    1260
ctgccgacac gtgcctcttc cctctcttct ctgtcaccct cctctggcgg tccttccacc    1320
ttcctctgtc ctccggatgt cctctttgcc cgtcttctcc cttggctgag caaagccatc    1380
```

```
ccctcaattc agggaagggc aaggagcctt cctcattcag gaaatcaaat cagtcttccg      1440
gtctgcagca cggaaaagca cataatcttt ctttgctgtg actgaaatgt atccctcgtt      1500
tatcatcccc tttgtttgtg attgctgcta aagtcagtag tatcgttttt ttaaaaaaaa      1560
agtttggtgt ttttaaccat gctgttccat caaagatgat accttaaact cccactgcaa      1620
gcccatgaat ttcccagaga gtggaacggc ttgctcttct ttctagaatg tccatgcact      1680
tgggttttaa tcagcagttc cctattattc tgattttaag ctgttcctgt gatgaactta      1740
gagacagcat cggtgtctgc tgctgtgtcc ccaggtcttg tgtgggtggc acagatctgg      1800
gcagttagat agtgctctgt gcctaaggtg aagccacact agggtgaagc ctcacttccc      1860
tgtttgagca atgcagtgcc tgctgcccgt gtgcatgaag gtacagccat tcagataagt      1920
ggaactattg agttacataa agaaaataga tttgcatttg tcaggcagac gtttatacaa      1980
caccacggtg cttttataca ttgtgcttat tttaataaaa ctgaaattct aaaaaaaaa      2039

<210> SEQ ID NO 13
<211> LENGTH: 766
<212> TYPE: DNA
<213> ORGANISM: Homo sapien

<400> SEQUENCE: 13
ctctctttcg attcttccat actcagagta cgcacggtct gattttctct ttggattctt       60
ccaaaatcag agtcagactg ctcccggtgc catgaacgga gacgacgcct tgcaaggag      120 acccacggtt ggtgctcaaa taccagagaa gatccaaaag gccttcgatg atattgccaa      180
atacttctct aaggaagagt gggaaaagat gaaagcctcg gagaaaatct tctatgtgta      240
tatgaagaga aagtatgagg ctatgactaa actaggtttc aaggccaccc tcccacccttt     300 catgtgtaat aaacgggccg aagacttcca ggggaatgat ttggataatg accctaaccg      360
tgggaatcag gttgaacgtc ctcagatgac tttcggcagg ctccagggaa tctccccgaa      420
gatcatgccc aagaagccag cagaggaagg aaatgattcg gaggaagtgc agaagcatc      480 tggcccacaa aatgatggga agagctgtg ccccccggga aaaccaacta cctctgagaa      540
gattcacgag agatctggac ccaaaagggg ggaacatgcc tggacccaca gactgcgtga      600
gagaaaacag ctggtgattt atgaagagat cagcgaccct gaggaagatg acgagtaact      660
cccctcaggg atacgacaca tgcccatgat gagaagcaga acgtggtgac ctttcacgaa      720
catgggcatg gctgcggacc cctcgtcatc aggtgcatag caagtg                    766

<210> SEQ ID NO 14
<211> LENGTH: 4204
<212> TYPE: DNA
<213> ORGANISM: Homo sapien

<400> SEQUENCE: 14
acgcaggcag tgatgtcacc cagaccacac cccttcccc aatgccactt caggggtac        60 tcagagtcag agacttggtc tgaggggagc agaagcaatc tgcagaggat ggcggtccag      120
gctcagccag gcatcaactt caggaccctg agggatgacc gaaggccccg cccacccacc      180
cccaactccc ccgaccccac caggatctac agcctcagga ccccgtccc aatccttacc      240 ccttgcccca tcaccatctt catgcttacc tccacccca tccgatcccc atccaggcag      300
aatccagttc caccctgcc cggaaaccag ggtagtaccg ttgccaggat gtgacgccac      360
tgacttgcgc attggaggtc agaagaccgc gagattctcg ccctgagcaa cgagcgacgg      420
cctgacgtcg gcggagggaa gccggcccag gctcggtgag gaggcaaggt aagacgctga      480
```

```
gggaggactg aggcgggcct cacctcagac agagggcctc aaataatcca gtgctgcctc        540
tgctgccggg cctgggccac cccgcagggg aagacttcca ggctgggtcg ccactacctc        600
accccgccga cccccgccgc tttagccacg gggaactctg gggacagagc ttaatgtggc        660
cagggcaggg ctggttagaa gaggtcaggg cccacgctgt ggcaggaatc aaggtcagga        720
ccccgagagg gaactgaggg cagcctaacc accaccctca ccaccattcc cgtcccccaa        780
cacccaaccc caccccatc ccccattccc atccccaccc ccaccccctat cctggcagaa        840 tccgggcttt gccctggta tcaagtcacg gaagctccgg gaatggcggc caggcacgtg         900
agtcctgagg ttcacatcta cggctaaggg agggaagggg ttcggtatcg cgagtatggc        960
cgttgggagg cagcgaaagg gcccaggcct cctggaagac agtggagtcc tgagggacc        1020 cagcatgcca ggacagggggg cccactgtac ccctgtctca aaccgaggca ccttttcatt     1080
cggctacggg aatcctaggg atgcagaccc acttcagcag ggggttgggg cccagccctg      1140
cgaggagtca tggggaggaa gaagagggag gactgagggg accttggagt ccagatcagt      1200
ggcaaccttg ggctggggga tgctgggcac agtggccaaa tgtgctctgt gctcattgcg      1260
ccttcagggt gaccagagag ttgagggctg tggtctgaag agtgggactt caggtcagca      1320
gagggaggaa tcccaggatc tgcagggccc aaggtgtacc cccaaggggc ccctatgtgg     1380
tggacagatg cagtggtcct aggatctgcc aagcatccag gtgaagagac tgagggagga      1440
ttgagggtac ccctgggaca gaatgcggac tgggggcccc ataaaaatct gccctgctcc      1500
tgctgttacc tcagagagcc tgggcagggc tgtcagctga ggtccctcca ttatcctagg      1560
atcactgatg tcagggaagg ggaagccttg gtctgagggg gctgcactca gggcagtaga      1620
gggaggctct cagaccctac taggagtgga ggtgaggacc aagcagtctc ctcacccagg      1680
gtacatggac ttcaataaat ttggacatct ctcgttgtcc tttcgggag gacctgggaa       1740 tgtatggcca gatgtgggtc ccctcatgtt tttctgtacc atatcaggta tgtgagttct      1800
tgacatgaga gattctcagg ccagcagaag ggagggatta ggccctataa ggagaaaggt     1860
gagggccctg agtgagcaca gagggatcc tccaccccag tagagtgggg acctcacaga      1920
gtctggccaa ccctcctgac agttctggga atccgtggct gcgtttgctg tctgcacatt     1980 ggggggcccgt ggattcctct cccaggaatc aggagctcca ggaacaaggc agtgaggact    2040
tggtctgagg cagtgtcctc aggtcacaga gtagagggg ctcagatagt gccaacggtg       2100
aaggtttgcc ttggattcaa accaagggcc ccctgccc cagaacacat ggactccaga        2160
gcgcctggcc tcaccctcaa tactttcagt cctgcagcct cagcatgcgc tggccggatg     2220
taccctgagg tgccctctca cttcctcctt caggttctga ggggacaggc tgacctggag     2280
gaccagaggc ccccggagga gcactgaagg agaagatctg taagtaagcc tttgttagag      2340
cctccaaggt tccattcagt actcagctga ggtctctcac atgctccctc tctcccagg       2400 ccagtgggtc tccattgccc agctcctgcc cacactcccg cctgttgccc tgaccagagt     2460
catcatgcct cttgagcaga ggagtcagca ctgcaagcct gaagaaggcc ttgaggcccg     2520
aggagaggcc ctgggcctgg tgggtgcgca ggctcctgct actgaggagc aggaggctgc     2580
ctcctcctct tctactctag ttgaagtcac cctggggggag gtgcctgctg ccgagtcacc    2640
agatcctccc cagagtcctc agggagcctc cagcctcccc actaccatga actaccctct      2700
ctggagccaa tccatgtgagg actccagcaa ccaagaagag gaggggccaa gcaccttccc    2760
tgacctggag tccgagttcc aagcagcact cagtaggaag gtggccgagt tggttcattt      2820
```

-continued

```
tctgctcctc aagtatcgag ccagggagcc ggtcacaaag gcagaaatgc tggggagtgt      2880
cgtcggaaat tggcagtatt tctttcctgt gatcttcagc aaagcttcca gttccttgca      2940
gctggtcttt ggcatcgagc tgatggaagt ggaccccatc ggccacttgt acatctttgc      3000
cacctgcctg ggcctctcct acgatggcct gctgggtgac aatcagatca tgcccaaggc      3060
aggcctcctg ataatcgtcc tggccataat cgcaagagag ggcgactgtg cccctgagga      3120
gaaaatctgg gaggagctga gtgtgttaga ggtgtttgag gggagggaag acagtatctt      3180
gggggatccc aagaagctgc tcacccaaca tttcgtgcag gaaaactacc tggagtaccg      3240
gcaggtcccc ggcagtgatc ctgcatgtta tgaattcctg tggggtccaa gggccctcgt      3300
tgaaaccagc tatgtgaaag tcctgcacca tatggtaaag atcagtggag acctcacat      3360 ttcctaccca cccctgcatg agtgggtttt gagagagggg gaagagtgag tctgagcacg      3420
agttgcagcc agggccagtg ggaggggtc tgggccagtg caccttccgg ggccgcatcc       3480
cttagtttcc actgcctcct gtgacgtgag gcccattctt cactctttga agcgagcagt      3540
cagcattctt agtagtgggt ttctgttctg ttggatgact ttgagattat tctttgtttc      3600
ctgttggagt tgttcaaatg ttccttttaa cggatggttg aatgagcgtc agcatccagg      3660
tttatgaatg acagtagtca cacatagtgc tgtttatata gtttaggagt aagagtcttg      3720
ttttttactc aaattgggaa atccattcca ttttgtgaat tgtgacataa taatagcagt      3780
ggtaaaagta tttgcttaaa attgtgagcg aattagcaat aacatacatg agataactca      3840
agaaatcaaa agatagttga ttcttgcctt gtacctcaat ctattctgta aaattaaaca      3900
aatatgcaaa ccaggatttc cttgacttct ttgagaatgc aagcgaaatt aaatctgaat      3960
aaataattct tcctcttcac tggctcgttt cttttccgtt cactcagcat ctgctctgtg      4020
ggaggccctg ggttagtagt ggggatgcta aggtaagcca gactcacgcc tacccatagg      4080
gctgtagagc ctaggacctg cagtcatata attaaggtgg tgagaagtcc tgtaagatgt      4140
agaggaaatg taagagaggg gtgagggtgt ggcgctccgg gtgagagtag tggagtgtca      4200
gtgc                                                                   4204
```

<210> SEQ ID NO 15
<211> LENGTH: 752
<212> TYPE: DNA
<213> ORGANISM: Homo sapien

<400> SEQUENCE: 15

```
atcctcgtgg gccctgacct tctctctgag agccgggcag aggctccgga gccatgcagg       60
ccgaaggccg gggcacaggg ggttcgacgg gcgatgctga tggcccagga ggccctggca      120
ttcctgatgg cccagggggc aatgctggcg gcccaggaga ggcgggtgcc acgggcggca      180
gaggtccccg gggcgcaggg gcagcaaggg cctcggggcc gggaggaggc gccccgcggg      240
gtccgcatgg cggcgcggct tcagggctga atggatgctg cagatgcggg gccaggggc       300 cggagagccg cctgcttgag ttctacctcg ccatgccttt cgcgacaccc atggaagcag      360
agctggcccg caggagcctg gcccaggatg ccccaccgct tcccgtgcca gggtgcttc       420 tgaaggagtt cactgtgtcc ggcaacatac tgactatccg actgactgct gcagaccacc      480
gccaactgca gctctccatc agctcctgtc tccagcagct ttccctgttg atgtggatca      540
cgcagtgctt tctgcccgtg ttttggctc agcctccctc agggcagagg cgctaagccc       600
agcctggcgc cccttcctag gtcatgcctc ctccccctagg gaatggtccc agcacgagtg      660
gccagttcat tgtgggggcc tgattgtttg tcgctggagg aggacggctt acatgtttgt      720
```
ttctgtagaa ataaaactg agctacgaaa aa                                    752

<210> SEQ ID NO 16
<211> LENGTH: 1967
<212> TYPE: PRT
<213> ORGANISM: Homo sapiens

<400> SEQUENCE: 16

Leu Glu Phe Lys Ile Ser Asp Glu Glu Ala Asp Ala Asp Ala Ala
1               5                   10                  15

Gly Arg Asp Ser Pro Ser Asn Thr Ser Gln Ser Glu Gln Gln Glu Ser
                20                  25                  30

Val Asp Ala Glu Gly Pro Val Val Lys Ile Met Ser Ser Arg Ser
        35                  40                  45

Val Lys Lys Gln Lys Glu Ser Gly Glu Glu Val Glu Ile Glu Glu Phe
    50                  55                  60

Tyr Val Lys Tyr Lys Asn Phe Ser Tyr Leu His Cys Gln Trp Ala Ser
65                  70                  75                  80

Ile Glu Asp Leu Glu Lys Asp Lys Arg Ile Gln Gln Lys Ile Lys Arg
                85                  90                  95

Phe Lys Ala Lys Gln Gly Gln Asn Lys Phe Leu Ser Glu Ile Glu Asp
                100                 105                 110

Glu Leu Phe Asn Pro Asp Tyr Val Glu Val Asp Arg Ile Met Asp Phe
            115                 120                 125

Ala Arg Ser Thr Asp Asp Arg Gly Glu Pro Val Thr His Tyr Leu Val
        130                 135                 140

Lys Trp Cys Ser Leu Pro Tyr Glu Asp Ser Thr Trp Glu Arg Arg Gln
145                 150                 155                 160

Asp Ile Asp Gln Ala Lys Ile Glu Glu Phe Glu Lys Leu Met Ser Arg
                165                 170                 175

Glu Pro Glu Thr Glu Arg Val Glu Arg Pro Pro Ala Asp Asp Trp Lys
            180                 185                 190

Lys Ser Glu Ser Ser Arg Glu Tyr Lys Asn Asn Asn Lys Leu Arg Glu
        195                 200                 205

Tyr Gln Leu Glu Gly Val Asn Trp Leu Leu Phe Asn Trp Tyr Asn Met
    210                 215                 220

Arg Asn Cys Ile Leu Ala Asp Glu Met Gly Leu Gly Lys Thr Ile Gln
225                 230                 235                 240

Ser Ile Thr Phe Leu Tyr Glu Ile Tyr Leu Lys Gly Ile His Gly Pro
                245                 250                 255

Phe Leu Val Ile Ala Pro Leu Ser Thr Ile Pro Asn Trp Glu Arg Glu
            260                 265                 270

Phe Arg Thr Trp Thr Glu Leu Asn Val Val Val Tyr His Gly Ser Gln
        275                 280                 285

Ala Ser Arg Arg Thr Ile Gln Leu Tyr Glu Met Tyr Phe Lys Asp Pro
    290                 295                 300

Gln Gly Arg Val Ile Lys Gly Ser Tyr Lys Phe His Ala Ile Ile Thr
305                 310                 315                 320

Thr Phe Glu Met Ile Leu Thr Asp Cys Pro Glu Leu Arg Asn Ile Pro
                325                 330                 335

Trp Arg Cys Val Val Ile Asp Glu Ala His Arg Leu Lys Asn Arg Asn
            340                 345                 350

Cys Lys Leu Leu Glu Gly Leu Lys Met Met Asp Leu Glu His Lys Val
        355                 360                 365

-continued

```
Leu Leu Thr Gly Thr Pro Leu Gln Asn Thr Val Glu Glu Leu Phe Ser
        370                 375                 380

Leu Leu His Phe Leu Glu Pro Ser Arg Phe Pro Ser Glu Thr Thr Phe
385                 390                 395                 400

Met Gln Glu Phe Gly Asp Leu Lys Thr Glu Glu Val Gln Lys Leu
                    405                 410                 415

Gln Ala Ile Leu Lys Pro Met Met Leu Arg Arg Leu Lys Glu Asp Val
                420                 425                 430

Glu Lys Asn Leu Ala Pro Lys Glu Thr Ile Ile Glu Val Glu Leu
            435                 440                 445

Thr Asn Ile Gln Lys Lys Tyr Tyr Arg Ala Ile Leu Glu Lys Asn Phe
        450                 455                 460

Thr Phe Leu Ser Lys Gly Gly Gln Ala Asn Val Pro Asn Leu Leu
465                 470                 475                 480

Asn Thr Met Met Glu Leu Arg Lys Cys Cys Asn His Pro Tyr Leu Ile
                    485                 490                 495

Asn Gly Ala Glu Glu Lys Ile Leu Glu Glu Phe Lys Glu Thr His Asn
                500                 505                 510

Ala Glu Ser Pro Asp Phe Gln Leu Gln Ala Met Ile Gln Ala Ala Gly
            515                 520                 525

Lys Leu Val Leu Ile Asp Lys Leu Leu Pro Lys Leu Lys Ala Gly Gly
        530                 535                 540

His Arg Val Leu Ile Phe Ser Gln Met Val Arg Cys Leu Asp Ile Leu
545                 550                 555                 560

Glu Asp Tyr Leu Ile Gln Arg Arg Tyr Pro Tyr Glu Arg Ile Asp Gly
                    565                 570                 575

Arg Val Arg Gly Asn Leu Arg Gln Ala Ala Ile Asp Arg Phe Ser Lys
                580                 585                 590

Pro Asp Ser Asp Arg Phe Val Phe Leu Leu Cys Thr Arg Ala Gly Gly
            595                 600                 605

Leu Gly Ile Asn Leu Thr Ala Ala Asp Thr Cys Ile Ile Phe Asp Ser
        610                 615                 620

Asp Trp Asn Pro Gln Asn Asp Leu Gln Ala Gln Ala Arg Cys His Arg
625                 630                 635                 640

Ile Gly Gln Ser Lys Ser Val Lys Ile Tyr Arg Leu Ile Thr Arg Asn
                    645                 650                 655

Ser Tyr Glu Arg Glu Met Phe Asp Lys Ala Ser Leu Lys Leu Gly Leu
                660                 665                 670

Asp Lys Ala Val Leu Gln Ser Met Ser Gly Arg Glu Asn Ala Thr Asn
            675                 680                 685

Gly Val Gln Gln Leu Ser Lys Lys Glu Ile Glu Asp Leu Leu Arg Lys
        690                 695                 700

Gly Ala Tyr Gly Ala Leu Met Asp Glu Asp Glu Gly Ser Lys Phe
705                 710                 715                 720

Cys Glu Glu Asp Ile Asp Gln Ile Leu Leu Arg Arg Thr His Thr Ile
                    725                 730                 735

Thr Ile Glu Ser Glu Gly Lys Gly Ser Thr Phe Ala Lys Ala Ser Phe
                740                 745                 750

Val Ala Ser Gly Asn Arg Thr Asp Ile Ser Leu Asp Asp Pro Asn Phe
            755                 760                 765

Trp Gln Lys Trp Ala Lys Lys Ala Glu Leu Asp Ile Asp Ala Leu Asn
770                 775                 780
```

-continued

Gly Arg Asn Asn Leu Val Ile Asp Thr Pro Arg Val Arg Lys Gln Thr
785             790             795             800

Arg Leu Tyr Ser Ala Val Lys Glu Asp Glu Leu Met Glu Phe Ser Asp
        805             810             815

Leu Glu Ser Asp Ser Glu Glu Lys Pro Cys Ala Lys Pro Arg Arg Pro
        820             825             830

Gln Asp Lys Ser Gln Gly Tyr Ala Arg Ser Glu Cys Phe Arg Val Glu
        835             840             845

Lys Asn Leu Leu Val Tyr Gly Trp Gly Arg Trp Thr Asp Ile Leu Ser
850             855             860

His Gly Arg Tyr Lys Arg Gln Leu Thr Glu Gln Asp Val Glu Thr Ile
865             870             875             880

Cys Arg Thr Ile Leu Val Tyr Cys Leu Asn His Tyr Lys Gly Asp Glu
            885             890             895

Asn Ile Lys Ser Phe Ile Trp Asp Leu Ile Thr Pro Thr Ala Asp Gly
        900             905             910

Gln Thr Arg Ala Leu Val Asn His Ser Gly Leu Ser Ala Pro Val Pro
        915             920             925

Arg Gly Arg Lys Gly Lys Val Lys Ala Gln Ser Thr Gln Pro Val
930             935             940

Val Gln Asp Ala Asp Trp Leu Ala Ser Cys Asn Pro Asp Ala Leu Phe
945             950             955             960

Gln Glu Asp Ser Tyr Lys Lys His Leu Lys His His Cys Asn Lys Val
            965             970             975

Leu Leu Arg Val Arg Met Leu Tyr Tyr Leu Arg Gln Glu Val Ile Gly
            980             985             990

Asp Gln Ala Asp Lys Ile Leu Glu Gly Ala Asp Ser Ser Glu Ala Asp
        995             1000            1005

Val Trp Ile Pro Glu Pro Phe His Ala Glu Val Pro Ala Asp Trp
1010            1015            1020

Trp Asp Lys Glu Ala Asp Lys Ser Leu Leu Ile Gly Val Phe Lys
1025            1030            1035

His Gly Tyr Glu Lys Tyr Asn Ser Met Arg Ala Asp Pro Ala Leu
1040            1045            1050

Cys Phe Leu Glu Arg Val Gly Met Pro Asp Ala Lys Ala Ile Ala
1055            1060            1065

Ala Glu Gln Arg Gly Thr Asp Met Leu Ala Asp Gly Gly Asp Gly
1070            1075            1080

Gly Glu Phe Asp Arg Glu Asp Glu Pro Glu Tyr Lys Pro Thr
1085            1090            1095

Arg Thr Pro Phe Lys Asp Glu Ile Asp Glu Phe Ala Asn Ser Pro
1100            1105            1110

Ser Glu Asp Lys Glu Glu Ser Met Glu Ile His Ala Thr Gly Lys
1115            1120            1125

His Ser Glu Ser Asn Ala Glu Leu Gly Gln Leu Tyr Trp Pro Asn
1130            1135            1140

Thr Ser Thr Leu Thr Thr Arg Leu Arg Arg Leu Ile Thr Ala Tyr
1145            1150            1155

Gln Arg Ser Tyr Lys Arg Gln Gln Met Arg Gln Glu Ala Leu Met
1160            1165            1170

Lys Thr Asp Arg Arg Arg Arg Pro Arg Glu Glu Val Arg Ala
1175            1180            1185

Leu Glu Ala Glu Arg Glu Ala Ile Ile Ser Glu Lys Arg Gln Lys

```
                    1190                1195                1200

Trp Thr Arg Arg Glu Glu Ala Asp Phe Tyr Arg Val Val Ser Thr
    1205                1210                1215

Phe Gly Val Ile Phe Asp Pro Val Lys Gln Gln Phe Asp Trp Asn
    1220                1225                1230

Gln Phe Arg Ala Phe Ala Arg Leu Asp Lys Lys Ser Asp Glu Ser
    1235                1240                1245

Leu Glu Lys Tyr Phe Ser Cys Phe Val Ala Met Cys Arg Arg Val
    1250                1255                1260

Cys Arg Met Pro Val Lys Pro Asp Asp Glu Pro Pro Asp Leu Ser
    1265                1270                1275

Ser Ile Ile Glu Pro Ile Thr Glu Glu Arg Ala Ser Arg Thr Leu
    1280                1285                1290

Tyr Arg Ile Glu Leu Leu Arg Lys Ile Arg Glu Gln Val Leu His
    1295                1300                1305

His Pro Gln Leu Gly Glu Arg Leu Lys Leu Cys Gln Pro Ser Leu
    1310                1315                1320

Asp Leu Pro Glu Trp Trp Glu Cys Gly Arg His Asp Arg Asp Leu
    1325                1330                1335

Leu Val Gly Ala Ala Lys His Gly Val Ser Arg Thr Asp Tyr His
    1340                1345                1350

Ile Leu Asn Asp Pro Glu Leu Ser Phe Leu Asp Ala His Lys Asn
    1355                1360                1365

Phe Ala Gln Asn Arg Gly Ala Gly Asn Thr Ser Ser Leu Asn Pro
    1370                1375                1380

Leu Ala Val Gly Phe Val Gln Thr Pro Pro Val Ile Ser Ser Ala
    1385                1390                1395

His Ile Gln Asp Glu Arg Val Leu Glu Gln Ala Glu Gly Lys Val
    1400                1405                1410

Glu Glu Pro Glu Asn Pro Ala Ala Lys Glu Lys Cys Glu Gly Lys
    1415                1420                1425

Glu Glu Glu Glu Glu Thr Asp Gly Ser Gly Lys Glu Ser Lys Gln
    1430                1435                1440

Glu Cys Glu Ala Glu Ala Ser Ser Val Lys Asn Glu Leu Lys Gly
    1445                1450                1455

Val Glu Val Gly Ala Asp Thr Gly Ser Lys Ser Ile Ser Glu Lys
    1460                1465                1470

Gly Ser Glu Glu Asp Glu Glu Glu Lys Leu Glu Asp Asp Asp Lys
    1475                1480                1485

Ser Glu Glu Ser Ser Gln Pro Glu Ala Gly Ala Val Ser Arg Gly
    1490                1495                1500

Lys Asn Phe Asp Glu Glu Ser Asn Ala Ser Met Ser Thr Ala Arg
    1505                1510                1515

Asp Glu Thr Arg Asp Gly Phe Tyr Met Glu Asp Gly Asp Pro Ser
    1520                1525                1530

Val Ala Gln Leu Leu His Glu Arg Thr Phe Ala Phe Ser Phe Trp
    1535                1540                1545

Pro Lys Asp Arg Val Met Ile Asn Arg Leu Asp Asn Ile Cys Glu
    1550                1555                1560

Ala Val Leu Lys Gly Lys Trp Pro Val Asn Arg Arg Gln Met Phe
    1565                1570                1575

Asp Phe Gln Gly Leu Ile Pro Gly Tyr Thr Pro Thr Thr Val Asp
    1580                1585                1590
```

-continued

```
Ser Pro Leu Gln Lys Arg Ser Phe Ala Glu Leu Ser Met Val Gly
    1595                1600                1605

Gln Ala Ser Ile Ser Gly Ser Glu Asp Ile Thr Thr Ser Pro Gln
    1610                1615                1620

Leu Ser Lys Glu Asp Ala Leu Asn Leu Ser Val Pro Arg Gln Arg
    1625                1630                1635

Arg Arg Arg Arg Arg Lys Ile Glu Ile Glu Ala Glu Arg Ala Ala
    1640                1645                1650

Lys Arg Arg Asn Leu Met Glu Met Val Ala Gln Leu Arg Glu Ser
    1655                1660                1665

Gln Val Val Ser Glu Asn Gly Gln Glu Lys Val Val Asp Leu Ser
    1670                1675                1680

Lys Ala Ser Arg Glu Ala Thr Ser Ser Thr Ser Asn Phe Ser Ser
    1685                1690                1695

Leu Ser Ser Lys Phe Ile Leu Pro Asn Val Ser Thr Pro Val Ser
    1700                1705                1710

Asp Ala Phe Lys Thr Gln Met Glu Leu Leu Gln Ala Gly Leu Ser
    1715                1720                1725

Arg Thr Pro Thr Arg His Leu Leu Asn Gly Ser Leu Val Asp Gly
    1730                1735                1740

Glu Pro Pro Met Lys Arg Arg Gly Arg Arg Lys Asn Val Glu
    1745                1750                1755

Gly Leu Asp Leu Leu Phe Met Ser His Lys Arg Thr Ser Leu Ser
    1760                1765                1770

Ala Glu Asp Ala Glu Val Thr Lys Ala Phe Glu Glu Asp Ile Glu
    1775                1780                1785

Thr Pro Pro Thr Arg Asn Ile Pro Ser Pro Gly Gln Leu Asp Pro
    1790                1795                1800

Asp Thr Arg Ile Pro Val Ile Asn Leu Glu Asp Gly Thr Arg Leu
    1805                1810                1815

Val Gly Glu Asp Ala Pro Lys Asn Lys Asp Leu Val Glu Trp Leu
    1820                1825                1830

Lys Leu His Pro Thr Tyr Thr Val Asp Met Pro Ser Tyr Val Pro
    1835                1840                1845

Lys Asn Ala Asp Val Leu Phe Ser Ser Phe Gln Lys Pro Lys Gln
    1850                1855                1860

Lys Arg His Arg Cys Arg Asn Pro Asn Lys Leu Asp Ile Asn Thr
    1865                1870                1875

Leu Thr Gly Glu Glu Arg Val Pro Val Val Asn Lys Arg Asn Gly
    1880                1885                1890

Lys Lys Met Gly Gly Ala Met Ala Pro Pro Met Lys Asp Leu Pro
    1895                1900                1905

Arg Trp Leu Glu Glu Asn Pro Glu Phe Ala Val Ala Pro Asp Trp
    1910                1915                1920

Thr Asp Ile Val Lys Gln Ser Gly Phe Val Pro Glu Ser Met Phe
    1925                1930                1935

Asp Arg Leu Leu Thr Gly Pro Val Val Arg Gly Glu Gly Ala Ser
    1940                1945                1950

Arg Arg Gly Arg Arg Pro Lys Ser Glu Ile Ala Arg Ala Ala
    1955                1960                1965
```

<210> SEQ ID NO 17
<211> LENGTH: 109

```
<212> TYPE: PRT
<213> ORGANISM: Homo sapiens
<220> FEATURE:
<221> NAME/KEY: UNSURE
<222> LOCATION: (84)..(84)
<223> OTHER INFORMATION: x = any amino acid
<220> FEATURE:
<221> NAME/KEY: UNSURE
<222> LOCATION: (100)..(100)
<223> OTHER INFORMATION: x = any amino acid

<400> SEQUENCE: 17
```

Arg Pro Ser Leu Pro Arg Ala Leu Pro Ala Ala Pro His Glu Arg Ser
1               5                   10                  15

Pro Ala Arg Pro Gly Ser Val Gly Gly Ala Pro Pro Met Leu Leu
            20                  25                  30

Gln Pro Ala Pro Cys Ala Pro Ser Ala Gly Phe Pro Arg Pro Leu Ala
        35                  40                  45

Ala Pro Gly Ala Met His Leu Phe Ala Glu Gly His His Val His Gln
    50                  55                  60

Asp Leu Arg Gly Arg Pro Ala Val Pro His Tyr Arg Arg Leu Ala Gln
65                  70                  75                  80

Glu Val Leu Xaa Gly Leu Arg Arg His Leu Arg Arg Pro Trp Ser Ser
                85                  90                  95

Pro Thr Ala Xaa Arg Ala Ser Pro Ala Ala Thr Ala Ser
            100                 105

```
<210> SEQ ID NO 18
<211> LENGTH: 897
<212> TYPE: PRT
<213> ORGANISM: Homo sapiens

<400> SEQUENCE: 18
```

Glu Phe Leu Leu Ser Lys Ser Lys Glu Pro Thr Pro Gly Gly Leu Asn
1               5                   10                  15

His Ser Leu Pro Gln His Pro Lys Cys Trp Gly Ala His His Ala Ser
            20                  25                  30

Leu Asp Gln Ser Ser Pro Pro Gln Ser Gly Pro Pro Gly Thr Pro Pro
        35                  40                  45

Ser Tyr Lys Leu Pro Leu Pro Gly Pro Tyr Asp Ser Arg Asp Asp Phe
    50                  55                  60

Pro Leu Arg Lys Thr Ala Ser Glu Pro Asn Leu Lys Val Arg Ser Arg
65                  70                  75                  80

Leu Lys Gln Lys Val Ala Glu Arg Arg Ser Ser Pro Leu Leu Arg Arg
                85                  90                  95

Lys Asp Gly Thr Val Ile Ser Thr Phe Lys Lys Arg Ala Val Glu Ile
            100                 105                 110

Thr Gly Ala Gly Pro Gly Ala Ser Ser Val Cys Asn Ser Ala Pro Gly
        115                 120                 125

Ser Gly Pro Ser Ser Pro Asn Ser Ser His Ser Thr Ile Ala Glu Asn
    130                 135                 140

Gly Phe Thr Gly Ser Val Pro Asn Ile Pro Thr Glu Met Leu Pro Gln
145                 150                 155                 160

His Arg Ala Leu Pro Leu Asp Ser Ser Pro Asn Gln Phe Ser Leu Tyr
                165                 170                 175

Thr Ser Pro Ser Leu Pro Asn Ile Ser Leu Gly Leu Gln Ala Thr Val
            180                 185                 190

Thr Val Thr Asn Ser His Leu Thr Ala Ser Pro Lys Leu Ser Thr Gln

-continued

```
                195                 200                 205
Gln Glu Ala Glu Arg Gln Ala Leu Gln Ser Leu Arg Gln Gly Gly Thr
            210                 215                 220

Leu Thr Gly Lys Phe Met Ser Thr Ser Ser Ile Pro Gly Cys Leu Leu
225                 230                 235                 240

Gly Val Ala Leu Glu Gly Asp Gly Ser Pro His Gly His Ala Ser Leu
                245                 250                 255

Leu Gln His Val Leu Leu Glu Gln Ala Arg Gln Gln Ser Thr Leu
            260                 265                 270

Ile Ala Val Pro Leu His Gly Gln Ser Pro Leu Val Thr Gly Glu Arg
            275                 280                 285

Val Ala Thr Ser Met Arg Thr Val Gly Lys Leu Pro Arg His Arg Pro
290                 295                 300

Leu Ser Arg Thr Gln Ser Ser Pro Leu Pro Gln Ser Pro Gln Ala Leu
305                 310                 315                 320

Gln Gln Leu Val Met Gln Gln His Gln Gln Phe Leu Glu Lys Gln
                325                 330                 335

Lys Gln Gln Gln Leu Gln Leu Gly Lys Ile Leu Thr Lys Thr Gly Glu
            340                 345                 350

Leu Pro Arg Gln Pro Thr Thr His Pro Glu Glu Thr Glu Glu Glu Leu
            355                 360                 365

Thr Glu Gln Gln Glu Val Leu Leu Gly Glu Gly Ala Leu Thr Met Pro
            370                 375                 380

Arg Glu Gly Ser Thr Glu Ser Glu Ser Thr Gln Glu Asp Leu Glu Glu
385                 390                 395                 400

Glu Asp Glu Glu Glu Asp Gly Glu Glu Glu Asp Cys Ile Gln Val
                405                 410                 415

Lys Asp Glu Glu Gly Glu Ser Gly Ala Glu Glu Gly Pro Asp Leu Glu
            420                 425                 430

Glu Pro Gly Ala Gly Tyr Lys Lys Leu Phe Ser Asp Ala Gln Pro Leu
            435                 440                 445

Gln Pro Leu Gln Val Tyr Gln Ala Pro Leu Ser Leu Ala Thr Val Pro
450                 455                 460

His Gln Ala Leu Gly Arg Thr Gln Ser Ser Pro Ala Ala Pro Gly Gly
465                 470                 475                 480

Met Lys Asn Pro Pro Asp Gln Pro Val Lys His Leu Phe Thr Thr Ser
                485                 490                 495

Val Val Tyr Asp Thr Phe Met Leu Lys His Gln Cys Met Cys Gly Asn
            500                 505                 510

Thr His Val His Pro Glu His Ala Gly Arg Ile Gln Ser Ile Trp Ser
            515                 520                 525

Arg Leu Gln Glu Thr Gly Leu Leu Ser Lys Cys Glu Arg Ile Arg Gly
            530                 535                 540

Arg Lys Ala Thr Leu Asp Glu Ile Gln Thr Val His Ser Glu Tyr His
545                 550                 555                 560

Thr Leu Leu Tyr Gly Thr Ser Pro Leu Asn Arg Gln Lys Leu Asp Ser
                565                 570                 575

Lys Lys Leu Leu Gly Pro Ile Ser Gln Lys Met Tyr Ala Val Leu Pro
            580                 585                 590

Cys Gly Gly Ile Gly Val Asp Ser Asp Thr Val Trp Asn Glu Met His
            595                 600                 605

Ser Ser Ser Ala Val Arg Met Ala Val Gly Cys Leu Leu Glu Leu Ala
            610                 615                 620
```

```
Phe Lys Val Ala Ala Gly Glu Leu Lys Asn Gly Phe Ala Ile Ile Arg
625                 630                 635                 640

Pro Pro Gly His His Ala Glu Glu Ser Thr Ala Met Gly Phe Cys Phe
            645                 650                 655

Phe Asn Ser Val Ala Ile Thr Ala Lys Leu Leu Gln Gln Lys Leu Asn
                660                 665                 670

Val Gly Lys Val Leu Ile Val Asp Trp Asp Ile His His Gly Asn Gly
            675                 680                 685

Thr Gln Gln Ala Phe Tyr Asn Asp Pro Ser Val Leu Tyr Ile Ser Leu
            690                 695                 700

His Arg Tyr Asp Asn Gly Asn Phe Phe Pro Gly Ser Gly Ala Pro Glu
705                 710                 715                 720

Glu Val Gly Gly Gly Pro Gly Val Gly Tyr Asn Val Asn Val Ala Trp
                725                 730                 735

Thr Gly Gly Val Asp Pro Pro Ile Gly Asp Val Glu Tyr Leu Thr Ala
                740                 745                 750

Phe Arg Thr Val Val Met Pro Ile Ala His Glu Phe Ser Pro Asp Val
            755                 760                 765

Val Leu Val Ser Ala Gly Phe Asp Ala Val Glu Gly His Leu Ser Pro
770                 775                 780

Leu Gly Gly Tyr Ser Val Thr Arg Cys Phe Gly His Leu Thr Arg
785                 790                 795                 800

Gln Leu Met Thr Leu Ala Gly Gly Arg Val Val Leu Ala Leu Glu Gly
                805                 810                 815

Gly His Asp Leu Thr Ala Ile Cys Asp Ala Ser Glu Ala Cys Val Ser
            820                 825                 830

Ala Leu Leu Ser Val Lys Leu Gln Pro Leu Asp Glu Ala Val Leu Gln
            835                 840                 845

Gln Lys Pro Asn Ile Asn Ala Val Ala Thr Leu Glu Lys Val Ile Glu
850                 855                 860

Ile Gln Ser Lys His Trp Ser Cys Val Gln Lys Phe Ala Ala Gly Leu
865                 870                 875                 880

Gly Arg Ser Leu Arg Gly Ala Gln Ala Gly Glu Thr Glu Glu Ala Glu
                885                 890                 895

Met

<210> SEQ ID NO 19
<211> LENGTH: 890
<212> TYPE: PRT
<213> ORGANISM: Homo sapiens

<400> SEQUENCE: 19

Met Phe Asp Tyr Met Asp Cys Glu Leu Lys Leu Ser Glu Ser Val Phe
1               5                   10                  15

Arg Gln Leu Asn Thr Ala Ile Ala Val Ser Gln Met Ser Ser Gly Gln
                20                  25                  30

Cys Arg Leu Ala Pro Leu Ile Gln Val Ile Gln Asp Cys Ser His Leu
            35                  40                  45

Tyr His Tyr Thr Val Lys Leu Leu Phe Lys Leu His Ser Cys Leu Pro
        50                  55                  60

Ala Asp Thr Leu Gln Gly His Arg Asp Arg Phe His Glu Gln Phe His
65                  70                  75                  80

Ser Leu Arg Asn Phe Phe Arg Arg Ala Ser Asp Met Leu Tyr Phe Lys
                85                  90                  95
```

```
Arg Leu Ile Gln Ile Pro Arg Leu Pro Glu Gly Pro Pro Asn Phe Leu
            100                 105                 110

Arg Ala Ser Ala Leu Ala Glu His Ile Lys Pro Val Val Ile Pro
        115                 120                 125

Glu Glu Ala Pro Glu Asp Glu Pro Glu Asn Leu Ile Glu Ile Ser
    130                 135                 140

Thr Gly Pro Pro Ala Gly Glu Pro Val Val Ala Asp Leu Phe Asp
145                 150                 155                 160

Gln Thr Phe Gly Pro Pro Asn Gly Ser Val Lys Asp Asp Arg Asp Leu
                165                 170                 175

Gln Ile Glu Ser Leu Lys Arg Glu Val Glu Met Leu Arg Ser Glu Leu
            180                 185                 190

Glu Lys Ile Lys Leu Glu Ala Gln Arg Tyr Ile Ala Gln Leu Lys Ser
        195                 200                 205

Gln Val Asn Ala Leu Glu Gly Glu Leu Glu Glu Gln Arg Lys Gln Lys
    210                 215                 220

Gln Lys Ala Leu Val Asp Asn Glu Gln Leu Arg His Glu Leu Ala Gln
225                 230                 235                 240

Leu Arg Ala Ala Gln Leu Glu Gly Glu Arg Ser Gln Gly Leu Arg Glu
                245                 250                 255

Glu Ala Glu Arg Lys Ala Ser Ala Thr Glu Ala Arg Tyr Asn Lys Leu
            260                 265                 270

Lys Glu Lys His Ser Glu Leu Val His Val His Ala Glu Leu Leu Arg
        275                 280                 285

Lys Asn Ala Asp Thr Ala Lys Gln Leu Thr Val Thr Gln Gln Ser Gln
    290                 295                 300

Glu Glu Val Ala Arg Val Lys Glu Gln Leu Ala Phe Gln Val Glu Gln
305                 310                 315                 320

Val Lys Arg Glu Ser Glu Leu Lys Leu Glu Glu Lys Ser Asp Gln Leu
                325                 330                 335

Glu Lys Leu Lys Arg Glu Leu Glu Ala Lys Ala Gly Glu Leu Ala Arg
            340                 345                 350

Ala Gln Glu Ala Leu Ser His Thr Glu Gln Ser Lys Ser Glu Leu Ser
        355                 360                 365

Ser Arg Leu Asp Thr Leu Ser Ala Glu Lys Asp Ala Leu Ser Gly Ala
    370                 375                 380

Val Arg Gln Arg Glu Ala Asp Leu Leu Ala Ala Gln Ser Leu Val Arg
385                 390                 395                 400

Glu Thr Glu Ala Ala Leu Ser Arg Glu Gln Gln Arg Ser Ser Gln Glu
                405                 410                 415

Gln Gly Glu Leu Gln Gly Arg Leu Ala Glu Arg Glu Ser Gln Glu Gln
            420                 425                 430

Gly Leu Arg Gln Arg Leu Leu Asp Glu Gln Phe Ala Val Leu Arg Gly
        435                 440                 445

Ala Ala Ala Glu Ala Ala Gly Ile Leu Gln Asp Ala Val Ser Lys Leu
    450                 455                 460

Asp Asp Pro Leu His Leu Arg Cys Thr Ser Ser Pro Asp Tyr Leu Val
465                 470                 475                 480

Ser Arg Ala Gln Glu Ala Leu Asp Ala Val Ser Thr Leu Glu Glu Gly
                485                 490                 495

His Ala Gln Tyr Leu Thr Ser Leu Ala Asp Ala Ser Ala Leu Val Ala
            500                 505                 510
```

-continued

```
Ala Leu Thr Arg Phe Ser His Leu Ala Ala Asp Thr Ile Ile Asn Gly
            515                 520                 525

Gly Ala Thr Ser His Leu Ala Pro Thr Asp Pro Ala Asp Arg Leu Ile
        530                 535                 540

Asp Thr Cys Arg Glu Cys Gly Arg Ala Leu Glu Leu Met Gly Gln
545                 550                 555                 560

Leu Gln Asp Gln Gln Ala Leu Arg His Met Gln Ala Ser Leu Val Arg
                565                 570                 575

Thr Pro Leu Gln Gly Ile Leu Gln Leu Gly Gln Glu Leu Lys Pro Lys
            580                 585                 590

Ser Leu Asp Val Arg Gln Glu Leu Gly Ala Val Asp Lys Glu
        595                 600                 605

Met Ala Ala Thr Ser Ala Ala Ile Glu Asp Ala Val Arg Arg Ile Glu
        610                 615                 620

Asp Met Met Asn Gln Ala Arg His Ala Ser Ser Gly Val Lys Leu Glu
625                 630                 635                 640

Val Asn Glu Arg Ile Leu Asn Ser Cys Thr Asp Leu Met Lys Ala Ile
                645                 650                 655

Arg Leu Leu Val Thr Thr Ser Thr Ser Leu Gln Lys Glu Ile Val Glu
            660                 665                 670

Ser Gly Arg Gly Ala Ala Thr Gln Gln Glu Phe Tyr Ala Lys Asn Ser
        675                 680                 685

Arg Trp Thr Glu Gly Leu Ile Ser Ala Ser Lys Ala Val Gly Trp Gly
        690                 695                 700

Ala Thr Gln Leu Val Glu Ala Ala Asp Lys Val Val Leu His Thr Gly
705                 710                 715                 720

Lys Tyr Glu Glu Leu Ile Val Cys Ser His Glu Ile Ala Ala Ser Thr
                725                 730                 735

Ala Gln Leu Val Ala Ala Ser Lys Val Lys Ala Asn Lys His Ser Pro
            740                 745                 750

His Leu Ser Arg Leu Gln Glu Cys Ser Arg Thr Val Asn Glu Arg Ala
        755                 760                 765

Ala Asn Val Val Ala Ser Thr Lys Ser Gly Gln Glu Gln Ile Glu Asp
        770                 775                 780

Arg Asp Thr Met Asp Phe Ser Gly Leu Ser Leu Ile Lys Leu Lys Lys
785                 790                 795                 800

Gln Glu Met Glu Thr Gln Val Arg Val Leu Glu Leu Glu Lys Thr Leu
                805                 810                 815

Glu Ala Glu Arg Met Arg Leu Gly Glu Leu Arg Lys Gln His Tyr Val
            820                 825                 830

Leu Ala Gly Ala Ser Gly Ser Pro Gly Glu Glu Val Ala Ile Arg Pro
        835                 840                 845

Ser Thr Ala Pro Arg Ser Val Thr Thr Lys Pro Pro Leu Ala Gln
        850                 855                 860

Lys Pro Ser Val Ala Pro Arg Gln Asp His Gln Leu Asp Lys Asp
865                 870                 875                 880

Gly Ile Tyr Pro Ala Gln Leu Val Asn Tyr
                885                 890

<210> SEQ ID NO 20
<211> LENGTH: 725
<212> TYPE: PRT
<213> ORGANISM: Homo sapiens

<400> SEQUENCE: 20
```

```
Met Ala Met Asp Ser Ser Leu Gln Ala Arg Leu Phe Pro Gly Leu Ala
1               5                   10                  15

Ile Lys Ile Gln Arg Ser Asn Gly Leu Ile His Ser Ala Asn Val Arg
            20                  25                  30

Thr Val Asn Leu Glu Lys Ser Cys Val Ser Val Glu Trp Ala Glu Gly
            35                  40                  45

Gly Ala Thr Lys Gly Lys Glu Ile Asp Phe Asp Asp Val Ala Ala Ile
        50                  55                  60

Asn Pro Glu Leu Leu Gln Leu Leu Pro Leu His Pro Lys Asp Asn Leu
65                  70                  75                  80

Pro Leu Gln Glu Asn Val Thr Ile Gln Lys Gln Lys Arg Arg Ser Val
                85                  90                  95

Asn Ser Lys Ile Pro Ala Pro Lys Glu Ser Leu Arg Ser Arg Ser Thr
            100                 105                 110

Arg Met Ser Thr Val Ser Glu Leu Arg Ile Thr Ala Gln Glu Asn Asp
        115                 120                 125

Met Glu Val Glu Leu Pro Ala Ala Ala Asn Ser Arg Lys Gln Phe Ser
130                 135                 140

Val Pro Pro Ala Pro Thr Arg Pro Ser Cys Pro Ala Val Ala Glu Ile
145                 150                 155                 160

Pro Leu Arg Met Val Ser Glu Glu Met Glu Glu Gln Val His Ser Ile
            165                 170                 175

Arg Gly Ser Ser Ser Ala Asn Pro Val Asn Ser Val Arg Arg Lys Ser
        180                 185                 190

Cys Leu Val Lys Glu Val Glu Lys Met Lys Asn Lys Arg Glu Glu Lys
        195                 200                 205

Lys Ala Gln Asn Ser Glu Met Arg Met Lys Arg Ala Gln Glu Tyr Asp
    210                 215                 220

Ser Ser Phe Pro Asn Trp Glu Phe Ala Arg Met Ile Lys Glu Phe Arg
225                 230                 235                 240

Ala Thr Leu Glu Cys His Pro Leu Thr Met Thr Asp Pro Ile Glu Glu
            245                 250                 255

His Arg Ile Cys Val Cys Val Arg Lys Arg Pro Leu Asn Lys Gln Glu
        260                 265                 270

Leu Ala Lys Lys Glu Ile Asp Val Ile Ser Ile Pro Ser Lys Cys Leu
            275                 280                 285

Leu Leu Val His Glu Pro Lys Leu Lys Val Asp Leu Thr Lys Tyr Leu
        290                 295                 300

Glu Asn Gln Ala Phe Cys Phe Asp Phe Ala Phe Asp Glu Thr Ala Ser
305                 310                 315                 320

Asn Glu Val Val Tyr Arg Phe Thr Ala Arg Pro Leu Val Gln Thr Ile
            325                 330                 335

Phe Glu Gly Gly Lys Ala Thr Cys Phe Ala Tyr Gly Gln Thr Gly Ser
            340                 345                 350

Gly Lys Thr His Thr Met Gly Gly Asp Leu Ser Gly Lys Ala Gln Asn
        355                 360                 365

Ala Ser Lys Gly Ile Tyr Ala Met Ala Ser Arg Asp Val Phe Leu Leu
    370                 375                 380

Lys Asn Gln Pro Cys Tyr Arg Lys Leu Gly Leu Glu Val Tyr Val Thr
385                 390                 395                 400

Phe Phe Glu Ile Tyr Asn Gly Lys Leu Phe Asp Leu Leu Asn Lys Lys
            405                 410                 415
```

-continued

```
Ala Lys Leu Arg Val Leu Glu Asp Gly Lys Gln Gln Val Gln Val Val
        420                 425                 430

Gly Leu Gln Glu His Leu Val Asn Ser Ala Asp Asp Val Ile Lys Met
            435                 440                 445

Leu Asp Met Gly Ser Ala Cys Arg Thr Ser Gly Gln Thr Phe Ala Asn
    450                 455                 460

Ser Asn Ser Ser Arg Ser His Ala Cys Phe Gln Ile Ile Leu Arg Ala
465                 470                 475                 480

Lys Gly Arg Met His Gly Lys Phe Ser Leu Val Asp Leu Ala Gly Asn
                485                 490                 495

Glu Arg Gly Ala Asp Thr Ser Ser Ala Asp Arg Gln Thr Arg Met Glu
            500                 505                 510

Gly Ala Glu Ile Asn Lys Ser Leu Leu Ala Leu Lys Glu Cys Ile Arg
        515                 520                 525

Ala Leu Gly Gln Asn Lys Ala His Thr Pro Phe Arg Glu Ser Lys Leu
    530                 535                 540

Thr Gln Val Leu Arg Asp Ser Phe Ile Gly Glu Asn Ser Arg Thr Cys
545                 550                 555                 560

Met Ile Ala Thr Ile Ser Pro Gly Ile Ser Ser Cys Glu Tyr Thr Leu
                565                 570                 575

Asn Thr Leu Arg Tyr Ala Asp Arg Val Lys Glu Leu Ser Pro His Ser
            580                 585                 590

Gly Pro Ser Gly Glu Gln Leu Ile Gln Met Glu Thr Glu Glu Met Glu
        595                 600                 605

Ala Cys Ser Asn Gly Ala Leu Ile Pro Gly Asn Leu Ser Lys Glu Glu
    610                 615                 620

Glu Glu Leu Ser Ser Gln Met Ser Ser Phe Asn Glu Ala Met Thr Gln
625                 630                 635                 640

Ile Arg Glu Leu Glu Glu Lys Ala Met Glu Glu Leu Lys Glu Ile Ile
                645                 650                 655

Gln Gln Gly Pro Asp Trp Leu Glu Leu Ser Glu Met Thr Glu Gln Pro
            660                 665                 670

Asp Tyr Asp Leu Glu Thr Phe Val Asn Lys Ala Glu Ser Ala Leu Ala
        675                 680                 685

Gln Gln Ala Lys His Phe Ser Ala Leu Arg Asp Val Ile Lys Ala Leu
    690                 695                 700

Arg Leu Ala Met Gln Leu Glu Glu Gln Ala Ser Arg Gln Ile Ser Ser
705                 710                 715                 720

Lys Lys Arg Pro Gln
                725
```

<210> SEQ ID NO 21
<211> LENGTH: 752
<212> TYPE: PRT
<213> ORGANISM: Homo sapiens

<400> SEQUENCE: 21

```
Arg Val Lys Ala Thr Leu Ser Glu Arg Lys Ile Gly Asp Ser Cys Asp
1               5                   10                  15

Lys Asp Leu Pro Leu Lys Phe Cys Glu Phe Pro Gln Lys Thr Ile Met
            20                  25                  30

Pro Gly Phe Lys Thr Thr Val Tyr Val Ser His Ile Asn Asp Leu Ser
        35                  40                  45

Asp Phe Tyr Val Gln Leu Ile Glu Asp Glu Ala Glu Ile Ser His Leu
    50                  55                  60
```

-continued

```
Ser Glu Arg Leu Asn Ser Val Lys Thr Arg Pro Glu Tyr Tyr Val Gly
 65                  70                  75                  80

Pro Pro Leu Gln Arg Gly Asp Met Ile Cys Ala Val Phe Pro Glu Asp
                 85                  90                  95

Asn Leu Trp Tyr Arg Ala Val Ile Lys Glu Gln Gln Pro Asn Asp Leu
            100                 105                 110

Leu Ser Val Gln Phe Ile Asp Tyr Gly Asn Val Ser Val His Thr
        115                 120                 125

Asn Lys Ile Gly Arg Leu Asp Leu Val Asn Ala Ile Leu Pro Gly Leu
    130                 135                 140

Cys Ile His Cys Ser Leu Gln Gly Phe Glu Val Pro Asp Asn Lys Asn
145                 150                 155                 160

Ser Lys Lys Met Met His Tyr Phe Ser Gln Arg Thr Ser Glu Ala Ala
                165                 170                 175

Ile Arg Cys Glu Phe Val Lys Phe Gln Asp Arg Trp Glu Val Ile Leu
            180                 185                 190

Ala Asp Glu His Gly Ile Ile Ala Asp Asp Met Ile Ser Arg Tyr Ala
        195                 200                 205

Leu Ser Glu Lys Ser Gln Val Glu Leu Ser Thr Gln Val Ile Lys Ser
    210                 215                 220

Ala Ser Ser Lys Ser Val Asn Lys Ser Asp Ile Asp Thr Ser Val Phe
225                 230                 235                 240

Leu Asn Trp Tyr Asn Pro Glu Lys Lys Met Ile Arg Ala Tyr Ala Thr
                245                 250                 255

Val Ile Asp Gly Pro Glu Tyr Phe Trp Cys Gln Phe Ala Asp Thr Glu
            260                 265                 270

Lys Leu Gln Cys Leu Glu Val Glu Val Gln Thr Ala Gly Glu Gln Val
        275                 280                 285

Ala Asp Arg Arg Asn Cys Ile Pro Cys Pro Tyr Ile Gly Asp Pro Cys
    290                 295                 300

Ile Val Arg Tyr Arg Glu Asp Gly His Tyr Tyr Arg Ala Leu Ile Thr
305                 310                 315                 320

Asn Ile Cys Glu Asp Tyr Leu Val Ser Val Arg Leu Val Asp Phe Gly
                325                 330                 335

Asn Ile Glu Asp Cys Val Asp Pro Lys Ala Leu Trp Ala Ile Pro Ser
            340                 345                 350

Glu Leu Leu Ser Val Pro Met Gln Ala Phe Pro Cys Cys Leu Ser Gly
        355                 360                 365

Phe Asn Ile Ser Glu Gly Leu Cys Ser Gln Glu Gly Asn Asp Tyr Phe
    370                 375                 380

Tyr Glu Ile Ile Thr Glu Asp Val Leu Glu Ile Thr Ile Leu Glu Ile
385                 390                 395                 400

Arg Arg Asp Val Cys Asp Ile Pro Leu Ala Ile Val Asp Leu Lys Ser
                405                 410                 415

Lys Gly Lys Ser Ile Asn Glu Lys Met Glu Lys Tyr Ser Lys Thr Gly
            420                 425                 430

Ile Lys Ser Ala Leu Pro Tyr Glu Asn Ile Asp Ser Glu Ile Lys Gln
        435                 440                 445

Thr Leu Gly Ser Tyr Asn Leu Asp Val Gly Leu Lys Lys Leu Ser Asn
    450                 455                 460

Lys Ala Val Gln Asn Lys Ile Tyr Met Glu Gln Gln Thr Asp Glu Leu
465                 470                 475                 480
```

```
Ala Glu Ile Thr Glu Lys Asp Val Asn Ile Gly Thr Lys Pro Ser
            485             490             495

Asn Phe Arg Asp Pro Lys Thr Asp Asn Ile Cys Glu Gly Phe Glu Asn
            500             505             510

Pro Cys Lys Asp Lys Ile Asp Thr Glu Glu Leu Glu Gly Glu Leu Glu
            515             520             525

Cys His Leu Val Asp Lys Ala Glu Phe Asp Asp Lys Tyr Leu Ile Thr
            530             535             540

Gly Phe Asn Thr Leu Leu Pro His Ala Asn Glu Thr Lys Glu Ile Leu
545             550             555             560

Glu Leu Asn Ser Leu Glu Val Pro Leu Ser Pro Asp Asp Glu Ser Lys
            565             570             575

Glu Phe Leu Glu Leu Glu Ser Ile Glu Leu Gln Asn Ser Leu Val Val
            580             585             590

Asp Glu Glu Lys Gly Glu Leu Ser Pro Val Pro Pro Asn Val Pro Leu
            595             600             605

Ser Gln Glu Cys Val Thr Lys Gly Ala Met Glu Leu Phe Thr Leu Gln
            610             615             620

Leu Pro Leu Ser Cys Glu Ala Lys Gln Pro Glu Leu Glu Leu Pro
625             630             635             640

Thr Ala Gln Leu Pro Leu Asp Asp Lys Met Asp Pro Leu Ser Leu Gly
            645             650             655

Val Ser Gln Lys Ala Gln Glu Ser Met Cys Thr Glu Asp Met Arg Lys
            660             665             670

Ser Ser Cys Val Glu Ser Phe Asp Asp Gln Arg Arg Met Ser Leu His
            675             680             685

Leu His Gly Ala Asp Cys Asp Pro Lys Thr Gln Asn Glu Met Asn Ile
            690             695             700

Cys Glu Glu Glu Phe Val Glu Tyr Lys Asn Arg Asp Ala Ile Ser Ala
705             710             715             720

Leu Met Pro Phe Ser Leu Arg Lys Lys Ala Val Met Glu Ala Ser Thr
            725             730             735

Ile Met Val Tyr Gln Ile Ile Phe Gln Asn Tyr Arg Thr Pro Thr Leu
            740             745             750

<210> SEQ ID NO 22
<211> LENGTH: 286
<212> TYPE: PRT
<213> ORGANISM: Homo sapiens

<400> SEQUENCE: 22

Ala Glu Val Lys Thr Pro Phe Asp Leu Ala Lys Ala Gln Glu Asn Ser
1               5               10              15

Asn Ser Val Lys Lys Thr Lys Phe Val Asn Leu Tyr Thr Arg Glu
            20              25              30

Arg Gln Asp Arg Leu Ala Val Leu Leu Pro Gly Arg His Pro Cys Asp
            35              40              45

Cys Leu Gly Gln Lys His Lys Leu Ile Asn Asn Cys Leu Ile Cys Gly
            50              55              60

Arg Ile Val Cys Glu Gln Glu Gly Ser Gly Pro Cys Leu Phe Cys Gly
65              70              75              80

Thr Leu Val Cys Thr His Glu Glu Gln Asp Ile Leu Gln Arg Asp Ser
            85              90              95

Asn Lys Ser Gln Lys Leu Leu Lys Lys Leu Met Ser Gly Val Glu Asn
            100             105             110
```

```
Ser Gly Lys Val Asp Ile Ser Thr Lys Asp Leu Leu Pro His Gln Glu
        115                 120                 125

Leu Arg Ile Lys Ser Gly Leu Glu Lys Ala Ile Lys His Lys Asp Lys
130                 135                 140

Leu Leu Glu Phe Asp Arg Thr Ser Ile Arg Arg Thr Gln Val Ile Asp
145                 150                 155                 160

Asp Glu Ser Asp Tyr Phe Ala Ser Asp Ser Asn Gln Trp Leu Ser Lys
                165                 170                 175

Leu Glu Arg Glu Thr Leu Gln Lys Arg Glu Glu Leu Arg Glu Leu
            180                 185                 190

Arg His Ala Ser Arg Leu Ser Lys Lys Val Thr Ile Asp Phe Ala Gly
            195                 200                 205

Arg Lys Ile Leu Glu Glu Asn Ser Leu Ala Glu Tyr His Ser Arg
        210                 215                 220

Leu Asp Glu Thr Ile Gln Ala Ile Ala Asn Gly Thr Leu Asn Gln Pro
225                 230                 235                 240

Leu Thr Lys Leu Asp Arg Ser Ser Glu Glu Pro Leu Gly Val Leu Val
                245                 250                 255

Asn Pro Asn Met Tyr Gln Ser Pro Pro Gln Trp Leu Thr Thr Gln Val
                260                 265                 270

Gln Pro His Arg Arg Arg Leu Ser Val Leu Gln Asp Leu Asp
            275                 280                 285

<210> SEQ ID NO 23
<211> LENGTH: 197
<212> TYPE: PRT
<213> ORGANISM: Homo sapiens

<400> SEQUENCE: 23

Pro Ser Lys Leu Gln Lys Asn Lys Gln Arg Leu Arg Asn Asp Pro Leu
1               5                   10                  15

Asn Gln Asn Lys Gly Lys Pro Asp Leu Asn Thr Thr Leu Pro Ile Arg
                20                  25                  30

Gln Thr Ala Ser Ile Phe Lys Gln Pro Val Thr Lys Val Thr Asn His
            35                  40                  45

Pro Ser Asn Lys Val Lys Ser Asp Pro Gln Arg Met Asn Glu Gln Pro
50                  55                  60

Arg Gln Leu Phe Trp Glu Lys Arg Leu Gln Gly Leu Ser Ala Ser Asp
65                  70                  75                  80

Val Thr Glu Gln Ile Ile Lys Thr Met Glu Leu Pro Lys Gly Leu Gln
                85                  90                  95

Gly Val Gly Pro Gly Ser Asn Asp Glu Thr Leu Leu Ser Ala Val Ala
                100                 105                 110

Ser Ala Leu His Thr Ser Ser Ala Pro Ile Thr Gly Gln Val Ser Ala
            115                 120                 125

Ala Val Glu Lys Asn Pro Ala Val Trp Leu Asn Thr Ser Gln Pro Leu
        130                 135                 140

Cys Lys Ala Phe Ile Val Thr Asp Glu Asp Ile Arg Lys Gln Glu Glu
145                 150                 155                 160

Arg Val Gln Gln Val Arg Lys Lys Leu Glu Glu Ala Leu Met Ala Asp
                165                 170                 175

Ile Leu Ser Arg Ala Ala Asp Thr Glu Glu Met Asp Ile Glu Met Asp
            180                 185                 190

Ser Gly Asp Glu Ala
```

195

<210> SEQ ID NO 24
<211> LENGTH: 353
<212> TYPE: PRT
<213> ORGANISM: Homo sapiens
<220> FEATURE:
<221> NAME/KEY: UNSURE
<222> LOCATION: (76)..(76)
<223> OTHER INFORMATION: X = any amino acid

<400> SEQUENCE: 24

```
Met Glu Glu Pro Gln Ser Asp Pro Ser Val Glu Pro Pro Leu Ser Gln
  1               5                  10                  15

Glu Thr Phe Ser Asp Leu Trp Lys Leu Leu Pro Glu Asn Asn Val Leu
             20                  25                  30

Ser Pro Leu Pro Ser Gln Ala Met Asp Asp Leu Met Leu Ser Pro Asp
         35                  40                  45

Asp Ile Glu Gln Trp Phe Thr Glu Asp Pro Gly Pro Asp Glu Ala Pro
 50                  55                  60

Arg Met Pro Glu Ala Ala Pro Pro Val Ala Pro Xaa Thr Ser Ser Ser
 65                  70                  75                  80

Tyr Thr Gly Gly Pro Cys Thr Ser Pro Leu Leu Ala Pro Val Ile Phe
             85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
            115                 120                 125

Ala Leu Asn Lys Met Phe Cys Gln Leu Ala Lys Thr Cys Pro Val Gln
        130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
            165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
            195                 200                 205

Arg Asn Thr Phe Arg His Ser Val Val Val Pro Cys Glu Pro Pro Glu
        210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
            245                 250                 255

Leu Glu Asp Ser Ser Gly Asn Leu Leu Gly Arg Asn Ser Phe Glu Val
            260                 265                 270

His Val Cys Ala Cys Pro Gly Arg Asp Arg Arg Thr Glu Glu Asn
            275                 280                 285

Leu Arg Lys Lys Gly Glu Pro His His Glu Leu Pro Pro Gly Ser Thr
        290                 295                 300

Lys Arg Ala Leu Pro Asn Asn Thr Ser Ser Pro Gln Pro Lys Lys
305                 310                 315                 320

Lys Pro Leu Asp Gly Glu Tyr Phe Thr Leu Gln Ile Arg Gly Arg Glu
            325                 330                 335

Arg Phe Glu Met Phe Arg Glu Leu Asn Glu Ala Leu Glu Leu Lys Asp
            340                 345                 350
```

-continued

Ala

<210> SEQ ID NO 25
<211> LENGTH: 545
<212> TYPE: PRT
<213> ORGANISM: Homo sapiens

<400> SEQUENCE: 25

```
Met Glu Thr Pro Ser Gln Arg Arg Ala Thr Arg Ser Gly Ala Gln Ala
1               5                   10                  15

Ser Ser Thr Pro Leu Ser Pro Thr Arg Ile Thr Arg Leu Gln Glu Lys
            20                  25                  30

Glu Asp Leu Gln Glu Leu Asn Asp Arg Leu Ala Val Tyr Ile Asp Arg
        35                  40                  45

Val Arg Ser Leu Glu Thr Glu Asn Ala Gly Leu Arg Leu Arg Ile Thr
    50                  55                  60

Glu Ser Glu Glu Val Val Ser Arg Glu Val Ser Gly Ile Lys Ala Ala
65                  70                  75                  80

Tyr Glu Ala Glu Leu Gly Asp Ala Arg Lys Thr Leu Asp Ser Val Ala
                85                  90                  95

Lys Glu Arg Ala Arg Leu Gln Leu Glu Leu Ser Lys Val Arg Glu Glu
            100                 105                 110

Phe Lys Glu Leu Lys Ala Arg Asn Thr Lys Lys Glu Gly Asp Leu Ile
        115                 120                 125

Ala Ala Gln Ala Arg Leu Lys Asp Leu Glu Ala Leu Leu Asn Ser Lys
    130                 135                 140

Glu Ala Leu Ser Thr Ala Leu Ser Glu Lys Arg Thr Leu Glu Gly
145                 150                 155                 160

Glu Leu His Asp Leu Arg Gly Gln Val Ala Lys Leu Glu Ala Ala Leu
                165                 170                 175

Gly Glu Ala Lys Lys Gln Leu Gln Asp Glu Met Leu Arg Arg Val Asp
            180                 185                 190

Ala Glu Asn Arg Leu Gln Thr Met Lys Glu Glu Leu Asp Phe Gln Lys
        195                 200                 205

Asn Ile Tyr Ser Glu Glu Leu Arg Glu Thr Lys Arg Arg His Glu Thr
    210                 215                 220

Arg Leu Val Glu Ile Asp Asn Gly Lys Gln Arg Glu Phe Glu Ser Arg
225                 230                 235                 240

Leu Ala Asp Ala Leu Gln Glu Leu Arg Ala Gln His Glu Asp Gln Val
                245                 250                 255

Glu Gln Tyr Lys Lys Glu Leu Glu Lys Thr Tyr Ser Ala Lys Leu Asp
            260                 265                 270

Asn Ala Arg Gln Ser Ala Glu Arg Asn Ser Asn Leu Val Gly Ala Ala
        275                 280                 285

His Glu Glu Leu Gln Gln Ser Arg Ile Arg Ile Asp Ser Leu Ser Ala
    290                 295                 300

Gln Leu Ser Gln Leu Gln Lys Gln Leu Ala Ala Lys Glu Ala Lys Leu
305                 310                 315                 320

Arg Asp Leu Glu Asp Ser Leu Ala Arg Glu Arg Asp Thr Ser Arg Arg
                325                 330                 335

Leu Leu Ala Glu Lys Glu Arg Glu Met Ala Glu Met Arg Ala Arg Met
            340                 345                 350

Gln Gln Gln Leu Asp Glu Tyr Gln Glu Leu Leu Asp Ile Lys Leu Ala
        355                 360                 365
```

-continued

```
Leu Asp Met Glu Ile His Ala Tyr Arg Lys Leu Leu Glu Gly Glu Glu
    370                 375                 380

Glu Arg Leu Arg Leu Ser Pro Ser Pro Thr Ser Gln Arg Ser Arg Gly
385                 390                 395                 400

Arg Ala Ser Ser His Ser Ser Gln Thr Gln Gly Gly Ser Val Thr
                405                 410                 415

Lys Lys Arg Lys Leu Glu Ser Thr Glu Ser Arg Ser Ser Phe Ser Gln
            420                 425                 430

His Ala Arg Thr Ser Gly Arg Val Ala Val Glu Glu Val Asp Glu Glu
            435                 440                 445

Gly Lys Phe Val Arg Leu Arg Asn Lys Ser Asn Glu Asp Gln Ser Met
    450                 455                 460

Gly Asn Trp Gln Ile Lys Arg Gln Asn Gly Asp Asp Pro Leu Leu Thr
465                 470                 475                 480

Tyr Arg Phe Pro Pro Lys Phe Thr Leu Lys Ala Gly Gln Val Val Thr
                485                 490                 495

Ile Trp Ala Ala Gly Ala Gly Ala Thr His Ser Pro Pro Thr Asp Leu
            500                 505                 510

Val Trp Lys Ala Gln Asn Thr Trp Gly Cys Gly Asn Ser Leu Arg Thr
            515                 520                 525

Ala Leu Ile Asn Ser Thr Gly Glu Glu Val Ala Met Arg Lys Leu Val
    530                 535                 540

Arg
545

<210> SEQ ID NO 26
<211> LENGTH: 1227
<212> TYPE: PRT
<213> ORGANISM: Homo sapiens

<400> SEQUENCE: 26

Gln Gly Ala Gln Arg Gly Ala Arg Val Gly Ala Ala Met Gly Leu Arg
1               5                   10                  15

Arg Ser Gly Asp Ser Arg Glu Pro Ser Gly Pro Gly Pro Glu Arg Val
                20                  25                  30

Phe Ser Gly Gly Pro Arg Pro Pro Ala Arg Gly Ala Gly Ala Pro Ala
            35                  40                  45

Pro Val Ala Gly Ala Val Ala Gly Cys Gly Gly Gln Asp His Val
    50                  55                  60

Gly Ser Pro Leu Arg Arg Arg Gly Ser Gly Leu Arg Asp Ala Ala Ala
65                  70                  75                  80

Glu Ala Val Glu Pro Ala Ala Arg Glu Leu Phe Glu Ala Cys Arg Asn
                85                  90                  95

Gly Asp Val Glu Arg Val Lys Arg Leu Val Thr Pro Glu Lys Val Asn
                100                 105                 110

Ser Arg Asp Thr Ala Gly Arg Lys Ser Thr Pro Leu His Phe Ala Ala
            115                 120                 125

Gly Phe Gly Arg Lys Asp Val Val Glu Tyr Leu Leu Gln Asn Gly Ala
    130                 135                 140

Asn Val Gln Ala Arg Asp Asp Gly Gly Leu Ile Pro Leu His Asn Ala
145                 150                 155                 160

Cys Ser Phe Gly His Ala Glu Val Val Asn Leu Leu Arg His Gly
                165                 170                 175

Ala Asp Pro Asn Ala Arg Asp Asn Trp Asn Tyr Thr Pro Leu His Glu
```

-continued

```
                180                 185                 190
Ala Ala Ile Lys Gly Lys Ile Asp Val Cys Ile Val Leu Leu Gln His
            195                 200                 205
Gly Ala Glu Pro Thr Ile Arg Asn Thr Asp Gly Arg Thr Ala Leu Asp
        210                 215                 220
Leu Ala Asp Pro Ser Ala Lys Ala Val Leu Thr Gly Glu Tyr Lys Lys
225                 230                 235                 240
Asp Glu Leu Leu Glu Ser Ala Arg Ser Gly Asn Glu Lys Met Met
                245                 250                 255
Ala Leu Leu Thr Pro Leu Asn Val Asn Cys His Ala Ser Asp Gly Arg
            260                 265                 270
Lys Ser Thr Pro Leu His Leu Ala Ala Gly Tyr Asn Arg Val Lys Ile
        275                 280                 285
Val Gln Leu Leu Leu Gln His Gly Ala Asp Val His Ala Lys Asp Lys
        290                 295                 300
Gly Asp Leu Val Pro Leu His Asn Ala Cys Ser Tyr Gly His Tyr Glu
305                 310                 315                 320
Val Thr Glu Leu Leu Val Lys His Gly Ala Cys Val Asn Ala Met Asp
                325                 330                 335
Leu Trp Gln Phe Thr Pro Leu His Glu Ala Ala Ser Lys Asn Arg Val
                340                 345                 350
Glu Val Cys Ser Leu Leu Ser Tyr Gly Ala Asp Pro Thr Leu Leu
            355                 360                 365
Asn Cys His Asn Lys Ser Ala Ile Asp Leu Ala Pro Thr Pro Gln Leu
        370                 375                 380
Lys Glu Arg Leu Ala Tyr Glu Phe Lys Gly His Ser Leu Leu Gln Ala
385                 390                 395                 400
Ala Arg Glu Ala Asp Val Thr Arg Ile Lys Lys His Leu Ser Leu Glu
                405                 410                 415
Met Val Asn Phe Lys His Pro Gln Thr His Glu Thr Ala Leu His Cys
                420                 425                 430
Ala Ala Ala Ser Pro Tyr Pro Lys Arg Lys Gln Ile Cys Glu Leu Leu
            435                 440                 445
Leu Arg Lys Gly Ala Asn Ile Asn Glu Lys Thr Lys Glu Phe Leu Thr
        450                 455                 460
Pro Leu His Val Ala Ser Glu Lys Ala His Asn Asp Val Val Glu Val
465                 470                 475                 480
Val Val Lys His Glu Ala Lys Val Asn Ala Leu Asp Asn Leu Gly Gln
                485                 490                 495
Thr Ser Leu His Arg Ala Ala Tyr Cys Gly His Leu Gln Thr Cys Arg
                500                 505                 510
Leu Leu Leu Ser Tyr Gly Cys Asp Pro Asn Ile Ile Ser Leu Gln Gly
            515                 520                 525
Phe Thr Ala Leu Gln Met Gly Asn Glu Asn Val Gln Gln Leu Leu Gln
        530                 535                 540
Glu Gly Ile Ser Leu Gly Asn Ser Glu Ala Asp Arg Gln Leu Leu Glu
545                 550                 555                 560
Ala Ala Lys Ala Gly Asp Val Glu Thr Val Lys Lys Leu Cys Thr Val
                565                 570                 575
Gln Ser Val Asn Cys Arg Asp Ile Glu Gly Arg Gln Ser Thr Pro Leu
            580                 585                 590
His Phe Ala Ala Gly Tyr Asn Arg Val Ser Val Val Glu Tyr Leu Leu
        595                 600                 605
```

```
-continued

Gln His Gly Ala Asp Val His Ala Lys Asp Lys Gly Leu Val Pro
    610                 615                 620

Leu His Asn Ala Cys Ser Tyr Gly His Tyr Glu Val Ala Glu Leu Leu
625                 630                 635                 640

Val Lys His Gly Ala Val Asn Val Ala Asp Leu Trp Lys Phe Thr
                645                 650                 655

Pro Leu His Glu Ala Ala Ala Lys Gly Lys Tyr Glu Ile Cys Lys Leu
            660                 665                 670

Leu Leu Gln His Gly Ala Asp Pro Thr Lys Lys Asn Arg Asp Gly Asn
            675                 680                 685

Thr Pro Leu Asp Leu Val Lys Asp Gly Asp Thr Asp Ile Gln Asp Leu
        690                 695                 700

Leu Arg Gly Asp Ala Ala Leu Leu Asp Ala Ala Lys Lys Gly Cys Leu
705                 710                 715                 720

Ala Arg Val Lys Lys Leu Ser Ser Pro Asp Asn Val Asn Cys Arg Asp
                725                 730                 735

Thr Gln Gly Arg His Ser Thr Pro Leu His Leu Ala Ala Gly Tyr Asn
            740                 745                 750

Asn Leu Glu Val Ala Glu Tyr Leu Leu Gln His Gly Ala Asp Val Asn
        755                 760                 765

Ala Gln Asp Lys Gly Gly Leu Ile Pro Leu His Asn Ala Ala Ser Tyr
    770                 775                 780

Gly His Val Asp Val Ala Ala Leu Leu Ile Lys Tyr Asn Ala Cys Val
785                 790                 795                 800

Asn Ala Thr Asp Lys Trp Ala Phe Thr Pro Leu His Glu Ala Ala Gln
                805                 810                 815

Lys Gly Arg Thr Gln Leu Cys Ala Leu Leu Leu Ala His Gly Ala Asp
            820                 825                 830

Pro Thr Leu Lys Asn Gln Glu Gly Gln Thr Pro Leu Asp Leu Val Ser
        835                 840                 845

Ala Asp Asp Val Ser Ala Leu Leu Thr Ala Ala Met Pro Pro Ser Ala
    850                 855                 860

Leu Pro Ser Cys Tyr Lys Pro Gln Val Leu Asn Gly Val Arg Ser Pro
865                 870                 875                 880

Gly Ala Thr Ala Asp Ala Leu Ser Ser Gly Pro Ser Pro Ser Ser
                885                 890                 895

Leu Ser Ala Ala Ser Ser Leu Asp Asn Leu Ser Gly Ser Phe Ser Glu
            900                 905                 910

Leu Ser Ser Val Val Ser Ser Ser Gly Thr Glu Gly Ala Ser Ser Leu
        915                 920                 925

Glu Lys Lys Glu Val Pro Gly Val Asp Phe Ser Ile Thr Gln Phe Val
    930                 935                 940

Arg Asn Leu Gly Leu Glu His Leu Met Asp Ile Phe Glu Arg Glu Gln
945                 950                 955                 960

Ile Thr Leu Asp Val Leu Val Glu Met Gly His Lys Glu Leu Lys Glu
                965                 970                 975

Ile Gly Ile Asn Ala Tyr Gly His Arg His Lys Leu Ile Lys Gly Val
            980                 985                 990

Glu Arg Leu Ile Ser Gly Gln Gln  Gly Leu Asn Pro Tyr  Leu Thr Leu
        995                 1000                1005

Asn Thr  Ser Gly Ser Gly Thr  Ile Leu Ile Asp Leu  Ser Pro Asp
    1010                1015                1020
```

-continued

```
Asp Lys Glu Phe Gln Ser Val Glu Glu Met Gln Ser Thr Val
    1025                1030                1035

Arg Glu His Arg Asp Gly Gly His Ala Gly Gly Ile Phe Asn Arg
    1040                1045                1050

Tyr Asn Ile Leu Lys Ile Gln Lys Val Cys Asn Lys Lys Leu Trp
    1055                1060                1065

Glu Arg Tyr Thr His Arg Arg Lys Glu Val Ser Glu Glu Asn His
    1070                1075                1080

Asn His Ala Asn Glu Arg Met Leu Phe His Gly Ser Pro Phe Val
    1085                1090                1095

Asn Ala Ile Ile His Lys Gly Phe Asp Glu Arg His Ala Tyr Ile
    1100                1105                1110

Gly Gly Met Phe Gly Ala Gly Ile Tyr Phe Ala Glu Asn Ser Ser
    1115                1120                1125

Lys Ser Asn Gln Tyr Val Tyr Gly Ile Gly Gly Gly Thr Gly Val
    1130                1135                1140

Gln Phe Thr Lys Thr Asp Leu Val Thr Phe Ala Thr Ala Ala Ala
    1145                1150                1155

Leu Leu Pro Gly Asn Leu Gly Lys Val Phe Pro Ala Val Gln Cys
    1160                1165                1170

Asn Glu Asn Gly Thr Ser Pro Pro Gly His His Ser Val Thr Gly
    1175                1180                1185

Arg Pro Ser Val Asn Gly Leu Ala Leu Ala Glu Tyr Val Ile Tyr
    1190                1195                1200

Arg Gly Glu Gln Ala Tyr Pro Glu Tyr Leu Ile Thr Tyr Gln Ile
    1205                1210                1215

Met Arg Pro Glu Gly Met Val Asp Gly
    1220                1225

<210> SEQ ID NO 27
<211> LENGTH: 290
<212> TYPE: PRT
<213> ORGANISM: Homo sapiens

<400> SEQUENCE: 27

His Ile Gln Lys Gln Lys His Phe Asn Glu Arg Glu Ala Ser Arg Val
1               5                   10                  15

Val Arg Asp Val Ala Ala Ala Leu Asp Phe Leu His Thr Lys Gly Ile
                20                  25                  30

Ala His Arg Asp Leu Lys Pro Glu Asn Ile Leu Cys Glu Ser Pro Glu
            35                  40                  45

Lys Val Ser Pro Val Lys Ile Cys Asp Phe Asp Leu Gly Ser Gly Met
        50                  55                  60

Lys Leu Asn Asn Ser Cys Thr Pro Ile Thr Thr Pro Glu Leu Thr Thr
65                  70                  75                  80

Pro Cys Gly Ser Ala Glu Tyr Met Ala Pro Glu Val Val Glu Val Phe
                85                  90                  95

Thr Asp Gln Ala Thr Phe Tyr Asp Lys Arg Cys Asp Leu Trp Ser Leu
            100                 105                 110

Gly Val Val Leu Tyr Ile Met Leu Ser Gly Tyr Pro Pro Phe Val Gly
        115                 120                 125

His Cys Gly Ala Asp Cys Gly Trp Asp Arg Gly Glu Val Cys Arg Val
    130                 135                 140

Cys Gln Asn Lys Leu Phe Glu Ser Ile Gln Glu Gly Lys Tyr Glu Phe
145                 150                 155                 160
```

-continued

Pro Asp Lys Asp Trp Ala His Ile Ser Ser Glu Ala Lys Asp Leu Ile
                165                 170                 175

Ser Lys Leu Leu Val Arg Asp Ala Lys Gln Lys Leu Ser Ala Ala Gln
            180                 185                 190

Val Leu Gln His Pro Trp Val Gln Gly Gln Ala Pro Glu Lys Gly Leu
        195                 200                 205

Pro Thr Pro Gln Val Leu Gln Arg Asn Ser Ser Thr Met Asp Leu Thr
    210                 215                 220

Leu Phe Ala Ala Glu Ala Ile Ala Leu Asn Arg Gln Leu Ser Gln His
225                 230                 235                 240

Glu Glu Asn Glu Leu Ala Glu Pro Glu Ala Leu Ala Asp Gly Leu
                245                 250                 255

Cys Ser Met Lys Leu Ser Pro Pro Cys Lys Ser Arg Leu Ala Arg Arg
            260                 265                 270

Arg Ala Leu Ala Gln Ala Gly Arg Gly Glu Asn Arg Ser Pro Pro Thr
        275                 280                 285

Ala Leu
    290

<210> SEQ ID NO 28
<211> LENGTH: 188
<212> TYPE: PRT
<213> ORGANISM: Homo sapiens

<400> SEQUENCE: 28

Met Asn Gly Asp Asp Ala Phe Ala Arg Arg Pro Thr Val Gly Ala Gln
1               5                   10                  15

Ile Pro Glu Lys Ile Gln Lys Ala Phe Asp Asp Ile Ala Lys Tyr Phe
            20                  25                  30

Ser Lys Glu Glu Trp Glu Lys Met Lys Ala Ser Glu Lys Ile Phe Tyr
        35                  40                  45

Val Tyr Met Lys Arg Lys Tyr Glu Ala Met Thr Lys Leu Gly Phe Lys
    50                  55                  60

Ala Thr Leu Pro Pro Phe Met Cys Asn Lys Arg Ala Glu Asp Phe Gln
65                  70                  75                  80

Gly Asn Asp Leu Asp Asn Asp Pro Asn Arg Gly Asn Gln Val Glu Arg
                85                  90                  95

Pro Gln Met Thr Phe Gly Arg Leu Gln Gly Ile Ser Pro Lys Ile Met
            100                 105                 110

Pro Lys Lys Pro Ala Glu Glu Gly Asn Asp Ser Glu Glu Val Pro Glu
        115                 120                 125

Ala Ser Gly Pro Gln Asn Asp Gly Lys Glu Leu Cys Pro Pro Gly Lys
    130                 135                 140

Pro Thr Thr Ser Glu Lys Ile His Glu Arg Ser Gly Pro Lys Arg Gly
145                 150                 155                 160

Glu His Ala Trp Thr His Arg Leu Arg Glu Arg Lys Gln Leu Val Ile
                165                 170                 175

Tyr Glu Glu Ile Ser Asp Pro Glu Glu Asp Glu
            180                 185

<210> SEQ ID NO 29
<211> LENGTH: 314
<212> TYPE: PRT
<213> ORGANISM: Homo sapiens

<400> SEQUENCE: 29

```
Met Pro Leu Glu Gln Arg Ser Gln His Cys Lys Pro Glu Gly Leu
1               5                   10                  15

Glu Ala Arg Gly Glu Ala Leu Gly Leu Val Gly Ala Gln Ala Pro Ala
            20                  25                  30

Thr Glu Glu Gln Glu Ala Ala Ser Ser Ser Thr Leu Val Glu Val
        35                  40                  45

Thr Leu Gly Glu Val Pro Ala Ala Glu Ser Pro Asp Pro Gln Ser
    50                  55                  60

Pro Gln Gly Ala Ser Ser Leu Pro Thr Thr Met Asn Tyr Pro Leu Trp
65                  70                  75                  80

Ser Gln Ser Tyr Glu Asp Ser Ser Asn Gln Glu Glu Glu Gly Pro Ser
                85                  90                  95

Thr Phe Pro Asp Leu Glu Ser Glu Phe Gln Ala Ala Leu Ser Arg Lys
            100                 105                 110

Val Ala Glu Leu Val His Phe Leu Leu Leu Lys Tyr Arg Ala Arg Glu
            115                 120                 125

Pro Val Thr Lys Ala Glu Met Leu Gly Ser Val Val Gly Asn Trp Gln
            130                 135                 140

Tyr Phe Phe Pro Val Ile Phe Ser Lys Ala Ser Ser Ser Leu Gln Leu
145                 150                 155                 160

Val Phe Gly Ile Glu Leu Met Glu Val Asp Pro Ile Gly His Leu Tyr
                165                 170                 175

Ile Phe Ala Thr Cys Leu Gly Leu Ser Tyr Asp Gly Leu Leu Gly Asp
            180                 185                 190

Asn Gln Ile Met Pro Lys Ala Gly Leu Leu Ile Ile Val Leu Ala Ile
            195                 200                 205

Ile Ala Arg Glu Gly Asp Cys Ala Pro Glu Glu Lys Ile Trp Glu Glu
            210                 215                 220

Leu Ser Val Leu Glu Val Phe Glu Gly Arg Glu Asp Ser Ile Leu Gly
225                 230                 235                 240

Asp Pro Lys Lys Leu Leu Thr Gln His Phe Val Gln Glu Asn Tyr Leu
                245                 250                 255

Glu Tyr Arg Gln Val Pro Gly Ser Asp Pro Ala Cys Tyr Glu Phe Leu
            260                 265                 270

Trp Gly Pro Arg Ala Leu Val Glu Thr Ser Tyr Val Lys Val Leu His
            275                 280                 285

His Met Val Lys Ile Ser Gly Gly Pro His Ile Ser Tyr Pro Pro Leu
            290                 295                 300

His Glu Trp Val Leu Arg Glu Gly Glu Glu
305                 310

<210> SEQ ID NO 30
<211> LENGTH: 180
<212> TYPE: PRT
<213> ORGANISM: Homo sapiens

<400> SEQUENCE: 30

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
            35                  40                  45

Gly Ala Ala Arg Ala Ser Gly Pro Gly Gly Gly Ala Pro Arg Gly Pro
```

-continued

```
             50                  55                  60
His Gly Gly Ala Ala Ser Gly Leu Asn Gly Cys Cys Arg Cys Gly Ala
 65              70                  75                  80

Arg Gly Pro Glu Ser Arg Leu Leu Glu Phe Tyr Leu Ala Met Pro Phe
                 85                  90                  95

Ala Thr Pro Met Glu Ala Glu Leu Ala Arg Arg Ser Leu Ala Gln Asp
                100                 105                 110

Ala Pro Pro Leu Pro Val Pro Gly Val Leu Leu Lys Glu Phe Thr Val
            115                 120                 125

Ser Gly Asn Ile Leu Thr Ile Arg Leu Thr Ala Ala Asp His Arg Gln
        130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
            180
```

COLON CANCER ANTIGEN PANEL

FIELD OF THE INVENTION

The invention relates to use of novel colon cancer-associated nucleic acid molecules and the polypeptides they encode as markers for cancer, including colon cancer. The invention also relates to the use of a panel of colon cancer-associated nucleic acid molecules and the polypeptides they encode and their use as markers for colon cancer. In addition, the invention relates to the use of such nucleic acid molecules and the polypeptides they encode for diagnosing colon cancer, and monitoring the colon cancer's response to treatment.

BACKGROUND OF THE INVENTION

Colon cancer, which is also known as cancer of the large bowel and colorectal cancer, is second only to lung cancer as a cause of cancer death in the United States. Colorectal cancer is a common malignant condition that generally occurs in individuals 50 years of age or older; and the overall incidence rate of colon cancer has not changed substantially during the past 40 years. (Harrison's Principles of Internal Medicine, 14/e, McGraw-Hill Companies, New York, 1998). The treatment of colon cancer once diagnosis is made depends on the extent of the cancer's invasion of the colon tissue, lymph nodes, and metastasis to other organs such as the liver. The survival rate for patients diagnosed with early-stage cancer is about 90% survival after 5 years. The five-year survival rate drops if the cancer is not detected until the cancer has spread beyond the mucosal layer of the colon, and drops significantly further if, when detected, the cancer has spread beyond the colon to the lymph nodes and beyond. Thus, it is critical to diagnose colon cancer at the earliest possible stage to increase the likelihood of a positive prognosis and outcome.

The traditional method of colon cancer diagnosis is through the use of non-invasive or mildly invasive diagnostic tests, more invasive visual examination, and histologic examination of biopsy. Although these tests may detect colon cancers, each has drawbacks that limit its effectiveness as a diagnostic tool. One primary source of difficulty with most of the currently available methods for diagnosing colorectal cancer, is patient reluctance to submit to, or follow through with the procedures, due to the uncomfortable or perceived embarrassing nature of the tests.

Some of the less invasive diagnostic methods include fecal occult blood testing and digital rectal exam. A digital exam may detect tumors at the distal end of the colon/rectum, but is not effective at more proximal levels. The usefulness of tests for occult blood is hampered by the intermittent bleeding patterns of colon cancers, which can result in a high percentage of false negative results. For example, approximately 50 percent of patients with documented colorectal cancers have a negative fecal blood test. In addition, false-positive fecal occult blood tests may also present problems for accurate diagnosis of colon cancer, because a number of non-colon cancer conditions (e.g.: gingivitis, ulcer, or aspirin use) may yield positive test results, resulting in unnecessary invasive follow-up procedures. These limitations of the less-invasive tests for colon cancer may delay a patient's procurement of rapid diagnosis and appropriate colon cancer treatment.

Visual examination of the colon for abnormalities can be performed through endoscopic or radiographic techniques such as rigid proctosigmoidoscopy, flexible sigmoidoscopy, colonoscopy, and barium-contrast enema. These methods are expensive, and uncomfortable, and also carry with them a risk of complications.

Another method of colon cancer diagnosis is the detection of carcinoembryonic antigen (CEA) in a blood sample from a subject, which when present at high levels, may indicate the presence of advanced colon cancer. But CEA levels may also be abnormally high when no cancer is present. Thus, this test is not selective for colon cancer, which limits the test's value as an accurate and reliable diagnostic tool. In addition, elevated CEA levels are not detectable until late-stage colon cancer, when the cure rate is low, treatment options limited, and patient prognosis poor.

More effective techniques for colon cancer diagnosis, and evaluation of colon cancer treatments are needed. Although available diagnostic procedures for colon cancer may be partially successful, the methods for detecting colon cancer remain unsatisfactory. There is a critical need for diagnostic tests that can detect colon cancer at its early stages, when appropriate treatment may substantially increase the likelihood of positive outcome for the patient.

SUMMARY OF THE INVENTION

The invention provides methods for diagnosing colon cancer based on the identification of certain colon cancer-associated polypeptides and the encoding nucleic acid molecules thereof, as antigens that elicit immune responses in colon cancer. The identified antigens can be utilized as markers for diagnosing colon cancer, for following the course of treatment of colon cancer, and for assessing colon cancer treatments.

According to one aspect of the invention, methods for diagnosing colon cancer in a subject are provided. The methods include obtaining a biological sample from a subject, contacting the sample with at least two different colon cancer-associated polypeptides encoded by nucleic acid molecules comprising a nucleotide sequence selected from the group consisting of SEQ ID NOs:1–15, and determining specific binding between the colon cancer-associated polypeptides and agents in the sample, wherein the presence of specific binding is diagnostic for colon cancer in the subject.

According to another aspect of the invention, methods of determining onset, progression, or regression, of colon cancer in a subject are provided. The methods include obtaining from a subject a first biological sample, contacting the first sample with at least two different colon cancer-associated polypeptides encoded by nucleic acid molecules comprising a nucleotide sequence selected form the group consisting of SEQ ID NOs:1–15, determining specific binding between agents in the first sample and the at least two different colon cancer-associated polypeptides, obtaining from a subject a second biological sample, contacting the second biological sample with at least two different colon cancer-associated polypeptides encoded by nucleic acid molecules comprising a nucleotide sequence selected form the group consisting of SEQ ID NOs:1–15, determining specific binding between agents in the second sample and the at least two different colon cancer-associated polypeptides, and comparing the determination of binding in the first sample to the determination of specific binding in the second sample as a determination of the onset, progression, or regression of the colon cancer.

According to yet another aspect of the invention, methods for selecting a course of treatment of a subject having or suspected of having colon cancer is provided. The methods include obtaining from the subject a biological sample, contacting the sample with at least two different colon cancer-associated polypeptides encoded by nucleic acid molecules comprising a nucleotide sequence selected from the group consisting of SEQ ID NOs:1–15, determining specific binding between agents in the sample that are differentially expressed in different types of cancer, and the colon cancer-associated polypeptides, and selecting a course of treatment appropriate to the cancer of the subject. In some embodiments, the treatment is administering antibodies that specifically bind to the colon cancer-associated polypeptides. In some embodiments, the antibodies are labeled with one or more cytotoxic agents.

In some embodiments of the foregoing methods, the biological sample is a blood sample. In some embodiments, the agents are antibodies or antigen-binding fragments thereof. In some embodiments of the foregoing methods, the biological sample is contacted with at least 3, 4, 5, 6, 7, 8, 9, 10, 11, 12, 13, 14, or 15 different colon cancer-associated polypeptides encoded by nucleic acid molecules comprising a nucleotide sequence selected from the group consisting of SEQ ID NOs:15. In some embodiments of the foregoing methods, the biological sample is contacted with a colon cancer-associated polypeptide other than those encoded by nucleic acid molecules comprising a nucleotide sequence selected from the group consisting of SEQ ID NOs:1–15.

According to another aspect of the invention, methods for diagnosing colon cancer in a subject are provided. The methods include obtaining a biological sample from a subject, contacting the sample with antibodies or antigen-binding fragments thereof, that bind specifically to at least two different colon cancer-associated polypeptides encoded by nucleic acid molecules comprising a nucleotide sequence selected from the group consisting of SEQ ID NOs:1–15, and determining specific binding between the antibodies or antigen-binding fragments thereof and colon cancer-associated polypeptides in the sample, wherein the presence of specific binding is diagnostic for colon cancer in the subject.

According to another aspect of the invention, methods for determining onset, progression, or regression, of colon cancer in a subject are provided. The methods include, obtaining from a subject a first biological sample, contacting the first sample with antibodies or antigen-binding fragments thereof, that bind specifically to at least two different colon cancer-associated polypeptides encoded by nucleic acid molecules comprising a nucleotide sequence selected from the group consisting of SEQ ID NOs:1–15, determining specific binding between colon cancer-associated polypeptides in the first sample and the antibodies or antigen-binding fragments thereof, obtaining from a subject a second biological sample, contacting the second sample with antibodies or antigen-binding fragments thereof, that bind specifically to at least two different colon cancer-associated polypeptides encoded by nucleic acid molecules comprising a nucleotide sequence selected from the group consisting of SEQ ID NOs:1–15, determining specific binding between colon cancer-associated polypeptides in the second sample and the antibodies or antigen-binding fragments thereof, and comparing the determination of specific binding in the first sample to the determination of specific binding in the second sample as a determination of the onset, progression, or regression of colon cancer.

According to another aspect of the invention methods for selecting a course of treatment of a subject having or suspected of having colon cancer are provided. The methods include obtaining from the subject a biological sample, contacting the sample with antibodies or antigen-binding fragments thereof that bind specifically to at least two different colon cancer-associated polypeptides encoded by nucleic acid molecules comprising a nucleotide sequence selected from the group consisting of SEQ ID NOs:1–15, determining specific binding between colon cancer-associated polypeptides in the sample that are differentially expressed in different types of cancer, and the antibodies or antigen-binding fragments thereof, and selecting a course of treatment appropriate to the cancer of the subject. In some embodiments, the treatment is administering antibodies that specifically bind to the colon cancer-associated polypeptides. In some embodiments, the antibodies are labeled with one or more cytotoxic agents.

In some embodiments of the foregoing methods, the sample is selected from the group consisting of: tissue, stool, cells, blood, and mucus. In preferred embodiments of the foregoing methods, the tissue is colorectal tissue. In some embodiments of the foregoing methods, the antibodies are monoclonal or polyclonal antibodies, and in some embodiments, of the foregoing methods the antibodies are chimeric, human, or humanized antibodies. In some embodiments the antibodies are single chain antibodies, and in some embodiments of the foregoing methods, the antigen-binding fragments are $F(ab')_2$, Fab, Fd, or Fv fragments. In some embodiments of the foregoing methods, the biological sample is contacted with antibodies or antigen-binding fragments thereof, that bind specifically to at least 3, 4, 5, 6, 7, 8, 9, 10, 11, 12, 13, 14, or 15 different colon cancer-associated polypeptides encoded by nucleic acid molecules comprising a nucleotide sequence selected from the group consisting of SEQ ID NOs:1–15. In some embodiments of the foregoing methods, the biological sample is contacted with an antibody or antigen-binding fragment thereof, that binds specifically to a colon cancer-associated polypeptide other than those encoded by nucleic acid molecules comprising a nucleotide sequence selected from the group consisting of SEQ ID NOs:1–15.

According to yet another aspect of the invention, kits for the diagnosis of colon cancer in a subject are provided. The kits include at least two different colon cancer-associated polypeptides encoded by nucleic acid molecules comprising a nucleotide sequence selected from the group consisting of: SEQ ID NOs:1–15, one or more control antigens, and instructions for the use of the polypeptides in the diagnosis of colon cancer. In some embodiments, the colon cancer-associated polypeptides are bound to a substrate. In some embodiments, the one or more agents are antibodies or antigen-binding fragments thereof. In some embodiments, the kit includes at least 3, 4, 5, 6, 7, 8, 9, 10, 11, 12, 13, 14, or 15 different colon cancer-associated polypeptides encoded by nucleic acid molecules comprising a nucleotide sequence selected from the group consisting of SEQ ID NOs:1–15. In some embodiments, the kit further includes a colon cancer-associated polypeptide other than those encoded by a nucleic acid molecule comprising a nucleotide sequence selected from the group consisting of SEQ ID NOs:1–15.

According to yet another aspect of the invention, kits for the diagnosis of colon cancer in a subject are provided. The kits include antibodies or antigen-binding fragments thereof that bind specifically to at least two different colon cancer-associated polypeptides encoded by nucleic acid molecules comprising a nucleotide sequence selected from the group consisting of SEQ ID NOs:1–15, one or more control agents, and instructions for the use of the agents in the diagnosis of colon cancer. In some embodiments, the one or more agents are antibodies or antigen-binding fragments thereof. In some embodiments, the one or more agents are bound to a substrate. In some embodiments, the kit includes antibodies or antigen-binding fragments thereof, that bind specifically to least 3, 4, 5, 6, 7, 8, 9, 10, 11, 12, 13, 14, or 15 different colon cancer-associated polypeptides encoded by nucleic acid molecules comprising a nucleotide sequence selected from the group consisting of SEQ ID NOs:1–15. In some embodiments, the kit further includes an antibody or antigen-binding fragment thereof, that binds specifically to a colon cancer-associated polypeptide other than those encoded by a nucleic acid molecule comprising a nucleotide sequence selected from the group consisting of SEQ ID NOs:1–15.

According to another aspect of the invention, protein microarrays are provided, which include at least two different colon cancer-associated polypeptides, wherein the colon cancer-associated polypeptides are encoded by nucleic acid molecules comprising a nucleotide sequence selected from the group consisting of: SEQ ID NOs: 1–15, fixed to a solid substrate. In some embodiments, the microarray comprises at least 3, 4, 5, 6, 7, 8, 9, 10, 11, 12, 13, 14, or 15 different colon cancer-associated polypeptides encoded by nucleic acid molecules comprising a nucleotide sequence selected from the group consisting of SEQ ID NOs:1–15. In some embodiments, the microarrays further consist essentially of a colon cancer-associated polypeptide other than those encoded by a nucleic acid molecule comprising a nucleotide sequence selected from the group consisting of SEQ ID NOs:1–15. In some embodiments, microarray further consists essential of at least one control polypeptide molecule.

According to yet another aspect of the invention, protein microarrays are provided, which include antibodies or antigen-binding fragments thereof, that specifically bind at least two different colon cancer-associated polypeptides encoded by nucleic acid molecules comprising a nucleotide sequence selected from the group consisting of: SEQ ID NOs:1–15, fixed to a solid substrate. In some embodiments, the protein microarray consists essentially of antibodies or antigen-binding fragments thereof, that bind specifically to least 3, 4, 5, 6, 7, 8, 9, 10, 11, 12, 13, 14, or 15 different colon cancer-associated polypeptides encoded by nucleic acid molecules comprising a nucleotide sequence selected from the group consisting of SEQ ID NOs:1–15. In some embodiments, the protein microarrays further consist essentially of an antibody or antigen-binding fragment thereof, that binds specifically to a colon cancer-associated polypeptide other than those encoded by a nucleic acid molecule comprising a nucleotide sequence selected from the group consisting of SEQ ID NOs:1–15. In some embodiments, the protein microarrays further consist essentially of at least one control polypeptide molecule. In some embodiments, the antibodies are monoclonal or polyclonal antibodies. In some embodiments, the antibodies are chimeric, human, or humanized antibodies. In some embodiments, the antibodies are single chain antibodies, and in some embodiments, the antigen-binding fragments are F(ab')$_2$, Fab, Fd, or Fv fragments.

According to another aspect of the invention nucleic acid microarrays are provided. The nucleic acid microarrays include at least two nucleic acids selected from the group consisting of SEQ ID NOs: 1–15, fixed to a solid substrate. In some embodiments, the microarray consists essentially of at least 3, 4, 5, 6, 7, 8, 9, 10, 11, 12, 13, 14, or 15 different nucleic acid molecules comprising a nucleotide sequence selected from the group consisting of SEQ ID NOs:1–15. In some embodiments, the microarray further consists essentially of a nucleic acid molecule other than those selected from the group consisting of SEQ ID NOs:1–15. In yet another embodiment, the microarrays further consist essentially of at least one control nucleic acid molecule.

According to another aspect of the invention, methods for diagnosing colon cancer in a subject are provided. The methods include obtaining from the subject a biological sample, and determining the expression of at least two colon cancer-associated nucleic acid molecules or expression products thereof in the sample, wherein the nucleic acid molecules comprise a nucleotide sequence selected from the group consisting of: SEQ ID NO: 1–15, wherein the expression is diagnosis of the colon cancer in the subject. In some embodiments, expression is determined for at least 3, 4, 5, 6, 7, 8, 9, 10, 11, 12, 13, 14, or 15 nucleic acid molecules comprising a nucleotide sequence selected from the group consisting of SEQ ID NOs:1–15. In some embodiments, the method includes determining expression of a colon cancer-associated nucleic acid molecule other than those comprising a nucleotide sequence selected from the group consisting of SEQ ID NOs:1–15. In some embodiments, the sample is selected from the group consisting of: tissue, stool, cells, blood, and mucus. In preferred embodiments, the tissue is colorectal tissue. In some embodiments, the expression of colon cancer-associated nucleic acid molecules is determined by a method selected from the group consisting of nucleic acid hybridization and nucleic acid amplification. In preferred embodiments, the hybridization is performed using a nucleic acid microarray.

According to yet another aspect of the invention, methods for determining onset, progression, or regression, of colon cancer in a subject are provided. The methods include obtaining from a subject a first biological sample, determining a level of expression of at least two colon cancer-associated nucleic acid molecules or expression products thereof in the first sample, wherein the nucleic acid molecules are selected from the group consisting of: SEQ ID NOs: 1–15, obtaining from the subject a second biological sample, determining a level of expression of at least two colon cancer-associated nucleic acid molecules or expression products thereof in the second sample, wherein the nucleic acid molecules are selected from the group consisting of: SEQ ID NOs: 1–15, and comparing the level of expression in the first sample to the level of expression in the second sample as a determination of the onset, progression, or regression of the colon cancer. In some embodiments, expression is determined for at least 3, 4, 5, 6, 7, 8, 9, 10, 11, 12, 13, 14, or 15 nucleic acid molecules selected from the group consisting of SEQ ID NOs:1–15. In some embodiments, the method further includes determining expression for a colon cancer-associated nucleic acid molecule other than those comprising a nucleotide sequence selected from the group consisting of SEQ ID NOs:1–15. In some embodiments, the sample is selected from the group consisting of: tissue, stool, cells, blood, and mucus. In preferred embodiments, the tissue is colorectal tissue. In some embodiments, the expression of colon cancer-associated nucleic acid molecules is determined by a method selected from the group consisting of nucleic acid hybridization and nucleic acid amplification. In preferred embodiments, the hybridization is performed using a nucleic acid microarray.

According to another aspect of the invention, methods for diagnosing cancer in a subject are provided. The methods include obtaining a biological sample from a subject, contacting the sample with a colon cancer-associated polypeptide encoded by a nucleic acid molecule comprising a nucleotide sequence selected from the group consisting of SEQ ID NOs:1, 2, 5, and 6, and determining specific binding between the colon cancer-associated polypeptide and agents in the sample, wherein the presence of specific binding is diagnostic for cancer in the subject.

According to another aspect of the invention, methods for determining onset, progression, or regression, of cancer in a subject are provided. The methods include obtaining from a subject a first biological sample, contacting the first sample with a colon cancer associated polypeptide encoded by a nucleic acid molecule comprising a nucleotide sequence selected from the group consisting of SEQ ID NOs:1, 2, 5, and 6, determining specific binding between agents in the first sample and the colon cancer-associated, obtaining from a subject a second biological sample, contacting the second sample with a colon cancer associated polypeptide encoded by a nucleic acid molecule comprising a nucleotide sequence selected from the group consisting of SEQ ID NOs:1, 2, 5, and 6, determining specific binding between agents in the second sample and the colon cancer-associated polypeptide, and comparing the determination of binding in the first sample to the determination of specific binding in the second sample as a determination of the onset, progression, or regression of cancer.

According to another aspect of the invention, methods for selecting a course of treatment of a subject having or suspected of having cancer are provided. The methods include obtaining from the subject a biological sample, contacting the sample with a colon cancer-associated polypeptide encoded by a nucleic acid molecule comprising a nucleotide sequence selected from the group consisting of SEQ ID NOs:1, 2, 5, and 6, determining specific binding between agents in the sample that are differentially expressed in different types of cancer, and the colon cancer-associated polypeptide, and selecting a course of treatment appropriate to the cancer of the subject. In some embodiments, the treatment is administering antibodies that specifically bind to the colon cancer-associated polypeptide. In some embodiments, the antibodies are labeled with one or more cylotoxic agents.

In some embodiments of the foregoing methods, the sample is blood. In some embodiments of the foregoing methods, the agents are antibodies or antigen-binding fragments thereof. In preferred embodiments of the foregoing methods, the cancer is colon cancer.

According to another aspect of the invention, methods for diagnosing cancer in a subject are provided. The methods include obtaining a biological sample from a subject, contacting the sample with an antibody or antigen-binding fragment thereof, that binds specifically to a colon cancer-associated polypeptide encoded by a nucleic acid molecule comprising a nucleotide sequence selected from the group consisting of SEQ ID NOs:1, 2, 5, and 6, and determining specific binding between the antibody or antigen-binding fragment thereof and the colon cancer-associated polypeptide in the sample, wherein the presence of specific binding is diagnostic for cancer in the subject.

According to another aspect of the invention, methods for determining onset, progression, or regression, of cancer in a subject are provided. The methods include obtaining from a subject a first biological sample, contacting the first sample with antibodies or antigen-binding fragments thereof, that bind specifically to a colon cancer-associated polypeptides encoded by a nucleic acid molecule comprising a nucleotide sequence selected from the group consisting of SEQ ID NOs:1, 2, 5, and 6, determining specific binding between colon cancer-associated polypeptides in the first sample and the antibodies or antigen-fragments thereof, obtaining from a subject a second biological sample, contacting the second sample with antibodies or antigen-binding fragments thereof, that bind specifically to a colon cancer-associated polypeptides encoded by a nucleic acid molecule comprising a nucleotide sequence selected from the group consisting of SEQ ID NOs:1, 2, 5, and 6, determining specific binding between colon cancer-associated polypeptides in the second sample and the antibodies or antigen-binding fragments thereof, and comparing the determination of specific binding in the first sample to the determination of specific binding in the second sample as a determination of the onset, progression, or regression of cancer.

According to another aspect of the invention, methods for selecting a course of treatment of a subject having or suspected of having cancer are provided. The methods include obtaining from the subject a biological sample, contacting the sample with antibodies or antigen-binding fragments thereof that bind specifically to a colon cancer-associated polypeptide encoded by a nucleic acid molecule comprising a nucleotide sequence selected from the group consisting of SEQ ID NOs:1, 2, 5, and 6, determining specific binding between colon cancer-associated polypeptides in the sample that are differentially expressed in different types of cancer, and the antibodies or antigen-binding fragments thereof, and selecting a course of treatment appropriate to the cancer of the subject. In some embodiments, the treatment is administering antibodies that specifically bind to the colon cancer-associated polypeptide. In some embodiments, the antibodies are labeled with one or more cytotoxic agents.

In some embodiments of the foregoing methods, the sample is selected from the group consisting of: tissue, stool, cells, blood, and mucus. In some embodiments of the foregoing methods, the tissue is colorectal tissue. In preferred embodiments of the foregoing methods, the antibodies are monoclonal or polyclonal antibodies, chimeric, human, or humanized antibodies. In some embodiments of the foregoing methods, the antibodies are single chain antibodies or antigen-binding fragments are $F(ab')_2$, Fab, Fd, or Fv fragments. In preferred embodiments of the foregoing methods, the cancer is colon cancer.

According to another aspect of the invention, kits for the diagnosis of cancer in a subject are provided. The kits include a colon cancer-associated polypeptide encoded by a nucleic acid molecule comprising a nucleotide sequence selected from the group consisting of: SEQ ID NOs: 1, 2, 5, and 6; one or more control antigens; and instructions for the use of the polypeptide and control antigens in the diagnosis of cancer. In some embodiments, the colon cancer-associated polypeptide is bound to a substrate. In some embodiments, the one or more agents are antibodies or antigen-binding fragments thereof. In preferred embodiments, the cancer is colon cancer.

According to another aspect of the invention, kits for the diagnosis of cancer in a subject, are provided. The kits include antibodies or antigen-binding fragments thereof that bind specifically to a colon cancer-associated polypeptide encoded by a nucleic acid molecule comprising a nucleotide sequence selected from the group consisting of SEQ ID NOs:1, 2, 5, and 6; one or more control agents; and instructions for the use of the antibodies, antigen-binding fragments, and agents in the diagnosis of cancer. In some embodiments, the one or more agents are antibodies or antigen-binding fragments thereof. In some embodiments, the one or more agents are bound to a substrate. In preferred embodiments, the cancer is colon cancer.

According to another aspect of the invention, protein microarrays are provided. The protein microarrays include a colon cancer-associated polypeptide, wherein the colon cancer-associated polypeptide is encoded by a nucleic acid molecule comprising a nucleotide sequence selected from the group consisting of: SEQ ID NOs: 1, 2, 5, and 6, fixed to a solid substrate. In some embodiments, the protein microarray further includes at least one control polypeptide molecule.

According to yet another aspect of the invention, protein microarrays are provided. The protein microarrays include antibodies or antigen-binding fragments thereof, that specifically bind a colon cancer-associated polypeptide encoded by a nucleic acid molecule comprising a nucleotide sequence selected from the group consisting of: SEQ ID NOs:1, 2, 5, and 6, fixed to a solid substrate. In some embodiments, the protein microarrays further include at least one control polypeptide molecule. In some embodiments, the antibodies are monoclonal or polyclonal antibodies. In some embodiments, the antibodies are chimeric, human, or humanized antibodies and in some embodiments, the antibodies are single chain antibodies. In some embodiments, the antigen-binding fragments are F(ab')$_2$, Fab, Fd, or Fv fragments.

According to another aspect of the invention, nucleic acid microarrays are provided. The nucleic acid microarrays include a nucleic acid selected from the group consisting of SEQ ID NOs: 1, 2, 5, and 6, fixed to a solid substrate. In some embodiments, the nucleic acid microarrays further include at least one control nucleic acid molecule.

According to yet another aspect of the invention, methods for diagnosing cancer in a subject are provided. The methods include obtaining from the subject a biological sample, and determining the expression of a colon cancer-associated nucleic acid molecule or expression product thereof in the sample, wherein the nucleic acid molecule comprises a nucleotide sequence selected from the group consisting of: SEQ ID NO: 1, 2, 5, and 6, wherein the expression is diagnostic of cancer in the subject. In some embodiments, the sample is selected from the group consisting of: tissue, stool, cells, blood, and mucus. In preferred embodiments, the tissue is colorectal tissue. In some embodiments, the expression of colon cancer-associated nucleic acid molecules is determined by a method selected from the group consisting of nucleic acid hybridization and nucleic acid amplification. In preferred embodiments, the hybridization is performed using a nucleic acid microarray. In preferred embodiments, the cancer is colon cancer.

According to another aspect of the invention, methods for determining onset, progression, or regression, of cancer in a subject are provided. The methods include obtaining from a subject a first biological sample, determining a level of expression of a colon cancer-associated nucleic acid molecule or expression products thereof in the first sample, wherein the nucleic acid molecule is selected from the group consisting of: SEQ ID NOs: 1, 2, 5, and 6, obtaining from the subject a second biological sample, determining a level of expression of a colon cancer-associated nucleic acid molecule or expression product thereof in the second sample, wherein the nucleic acid molecule is selected from the group consisting of: SEQ ID NOs: 1, 2, 5, and 6, and comparing the level of expression in the first sample to the level of expression in the second sample as a determination of the onset, progression, or regression of the cancer. In some embodiments, the sample is selected from the group consisting of: tissue, stool, cells, blood, and mucus. In preferred embodiments, the tissue is colorectal tissue. In some embodiments, the expression of colon cancer-associated nucleic acid molecules is determined by a method selected from the group consisting of nucleic acid hybridization and nucleic acid amplification. In some embodiments, the hybridization is performed using a nucleic acid microarray. In preferred embodiments, the cancer is colon cancer.

DESCRIPTION OF THE INVENTION

The invention described herein relates to the identification of polypeptides that elicit specific immune responses in subjects with cancer, particularly colon cancer, which is also known as large-bowel cancer and colorectal cancer. Colon cancer-associated polypeptides have been identified through SEREX screening of patients with cancer. The SEREX method (serological analysis of antigens by recombinant expression cloning), has been described by Sahin et al. (*Proc. Natl. Acad. Sci. USA* 92:11810–11813, 1995). The newly identified colon cancer-associated polypeptides and the encoding nucleic acid molecules thereof may be used as markers for cancer, including colon cancer, and may be used in the diagnosis and treatment assessment of colon cancer in humans. In addition, sets of at least two colon cancer-associated polypeptides and the encoding nucleic acid molecules thereof, may be used as markers in the diagnosis and treatment assessment of colon cancer in humans.

Polypeptides that elicit specific immune responses in colon cancer have now been identified and this identification allows use of these newly identified colon cancer-associated polypeptides or the encoding nucleic acids molecules thereof in cancer diagnostic assays and kits. In addition, sets of at least two of these new or previously identified polypeptides or the encoding nucleic acid molecules thereof, may be used in colon cancer diagnostic assays and kits. Such assays and kits are useful to detect colon cancer in human subjects, and for staging the progression, regression, or onset of colon cancer in subjects. The methods and kits described herein may also be used to evaluate treatments for colon cancer.

As used herein, "colon cancer-associated polypeptides" means polypeptides that elicit specific immune responses in animals having colon cancer and thus, include colon cancer-associated antigens and fragments of colon cancer-associated antigens, that are recognized by the immune system (e.g., by antibodies and/or T lymphocytes). The invention also relates to the use of the nucleic acid molecules that encode the colon cancer-associated polypeptides. In all embodiments, human colon cancer-associated polypeptides and the encoding nucleic acid molecules thereof, are preferred. As used herein, the "encoding nucleic acid molecules thereof" means the nucleic acid molecules that code for the polypeptides.

As used herein, a subject is preferably a human, non-human primate, cow, horse, pig, sheep, goat, dog, cat, or rodent. In all embodiments, human subjects are preferred. In some embodiments, the subject is suspected of having cancer and in preferred embodiments the subject is suspected of having colon cancer. In some embodiments the subject has been diagnosed with cancer, and in preferred embodiments the subject has been diagnosed with colon cancer.

As used herein, "different types" of cancer may include different histological types, cell types, different stages of cancer, (e.g., primary tumor or metastatic growth).

Methods for identifying subjects suspected of having colon cancer may include fecal occult blood examination, digital examination, CEA testing, endoscopic or radiographic techniques, biopsy, subject's family medical history, subject's medical history, or imaging technologies, such as magnetic resonance imaging (MRI). Such methods for identifying subjects suspected of having colon cancer are well-known to those of skill in the medical arts. As used herein, a biological sample includes, but is not limited to: tissue, body fluid (e.g. blood), bodily exudate, mucus, and stool specimen. The tissue may be obtained from a subject or may be grown in culture (e.g. from a cell line).

As used herein, a colorectal tissue sample is tissue obtained (e.g., from a colorectal tissue biopsy) using methods well-known to those of ordinary skill in the related medical arts. The phrase "suspected of being cancerous" as used herein means a colon cancer tissue sample believed by one of ordinary skill in the medical arts to contain cancerous cells. Methods for obtaining the sample from the biopsy include gross apportioning of a mass, microdissection, laser-based microdissection, or other art-known cell-separation methods.

Because of the variability of the cell types in diseased-tissue biopsy material, and the variability in sensitivity of the diagnostic methods used, the sample size required for analysis may range from 1, 10, 50, 100, 200, 300, 500, 1000, 5000, 10,000, to 50,000 or more cells. The appropriate sample size may be determined based on the cellular composition and condition of the biopsy and the standard preparative steps for this determination and subsequent isolation of the nucleic acid for use in the invention are well known to one of ordinary skill in the art. An example of this, although not intended to be limiting, is that in some instances a sample from the biopsy may be sufficient for assessment of RNA expression without amplification, but in other instances the lack of suitable cells in a small biopsy region may require use of RNA conversion and/or amplification methods or other methods to enhance resolution of the nucleic acid molecules. Such methods, which allow use of limited biopsy materials, are well known to those of ordinary skill in the art and include, but are not limited to: direct RNA amplification, reverse transcription of RNA to cDNA, amplification of cDNA, or the generation of radio-labeled nucleic acids.

In some embodiments, the colon cancer-associated nucleic acid molecules from the group of nucleic acid sequences numbered 1 through 15 in Table 3 (SEQ ID Nos: 1–15) and the colon cancer-associated polypeptides encoded by SEQ ID NOs: 1–15, are the group of polypeptide sequences SEQ ID NOs: 16 through 30 in Table 3. In some embodiments, colon cancer-associated polypeptides may include polypeptides other than those encoded by nucleic acid molecules comprising a nucleotide sequence selected from the group consisting of SEQ ID NOs:1–15.

The invention involves in some embodiments, diagnosing or monitoring colon cancer in subjects by determining the presence of an immune response to at least two colon cancer-associated polypeptides. In some embodiments, cancer, such as colon cancer, in subjects may be diagnosed or monitored by determining the presence of an immune response to one of the novel colon cancer-associated polypeptides described herein. In preferred embodiments, this determination is performed by assaying a bodily fluid obtained from the subject, preferably blood, for the presence of antibodies against at least two colon cancer-associated polypeptides or the nucleic acid molecules that encode the cancer-associated polypeptides, or for the presence of antibodies against one of the novel colon cancer-associated polypeptides or the encoding nucleic acid molecules thereof as described herein. This determination may also be performed by assaying a tissue of the subject for the presence of at least two colon cancer-associated polypeptides and/or the encoding nucleic acid molecules thereof, or assaying a tissue of the subject for the presence of one of the novel colon cancer-associated polypeptides or the encoding nucleic acid molecules thereof as described herein.

Measurement of the immune response against one of the novel colon cancer-associated polypeptides described herein, or at least two colon cancer-associated polypeptides in a subject over time by sequential determinations permits monitoring of the disease and/or the effects of a course of treatment. For example, a sample may be obtained from a subject, tested for an immune response to one of the novel colon cancer-associated polypeptides or may be tested for an immune response to at least two colon cancer-associated polypeptides and at a second, subsequent time, another sample may be obtained from the subject and similarly tested. The results of the first and second (subsequent) tests can be compared as a measure of the onset, regression or progression of colon cancer, or, if colon-cancer treatment was undertaken during the interval between obtaining the samples, the effectiveness of the treatment may be evaluated by comparing the results of the two tests.

The invention also involves in some embodiments diagnosing or monitoring colon cancer by determining the presence of at least two colon cancer-associated polypeptides and the encoding nucleic acid molecules thereof, or by determining the presence of one of the novel colon cancer-associated polypeptides and the encoding nucleic acid molecules thereof as described herein. In some important embodiments, this determination is performed by assaying a tissue sample from subject, preferably one believed to be cancerous, for the presence of at least two colon cancer-associated polypeptides or the encoding nucleic acid molecules thereof, or for the presence of one of the novel colon cancer-associated polypeptides and the encoding nucleic acid molecules thereof as described herein.

In other important embodiments, the presence of at least two colon cancer-associated polypeptides and the encoding nucleic acid molecules thereof, or the presence of one of the novel colon cancer-associated polypeptides and the encoding nucleic acid molecules thereof as described herein, are measured in mucus or fecal/stool samples. Such samples may contain colon cancer-associated polypeptides, or the encoding nucleic acids thereof, for example in shed cells. Measurement of the presence of at least two colon cancer-associated polypeptides and the encoding nucleic acid molecules thereof, or the presence of one of the novel colon cancer-associated polypeptides and the encoding nucleic acid molecules thereof as described herein, in subject's samples over time by sequential determinations at temporal intervals permits monitoring of the disease and/or the effects of a course of treatment.

In all embodiments, treatment for colon cancer may include, but is not limited to: surgical intervention, chemotherapy, radiotherapy, and adjuvant systemic therapies. In a preferred embodiment, treatment may include administering antibodies that specifically bind to the colon cancer-associated antigen. Optionally, an antibody can be linked to one or more detectable markers, antitumor agents or immunomodulators. Antitumor agents can include cytotoxic agents and agents that act on tumor neovasculature. Detectable markers include, for example, radioactive or fluorescent markers. Cytotoxic agents include cytotoxic radionuclides, chemical toxins and protein toxins.

The cytotoxic radionuclide or radiotherapeutic isotope may be an alpha-emitting isotope such as $^{225}$Ac, $^{211}$At, $^{212}$Bi, or $^{213}$Bi. Alternatively, the cytotoxic radionuclide may be a beta-emitting isotope such as $^{186}$Rh, $^{188}$Rh, 90Y, 131I or $^{67}$Cu. Further, the cytotoxic radionuclide may emit Auger and low energy electrons such as the isotopes $^{125}$I, $^{123}$I or $^{77}$Br.

Suitable chemical toxins or chemotherapeutic agents include members of the enediyne family of molecules, such as chalicheamicin and esperamicin. Chemical toxins can also be taken from the group consisting of methotrexate, doxorubicin, melphalan, chlorambucil, ARA-C, vindesine, mitomycin C, cis-platinum, etoposide, bleomycin and 5-fluorouaracil. Other chemotherapeutic agents are known to those skilled in the art.

Agents that act on the tumor neovasculature can include tubulin-binding agents such as combrestatin A4 (Griggs et al., Lancet Oncol. 2:82, 2001) and angiostatin and endostatin (reviewed in Rosen, Oncologist 5:20, 2000, incorporated by reference herein). Immunomodulators may also be conjugated to colon cancer-associated antibodies.

The invention thus involves in one aspect, colon cancer-associated polypeptides, genes encoding those polypeptides, functional modifications and variants of the foregoing, useful fragments of the foregoing, as well as diagnostics relating thereto, and diagnostic uses thereof. In some embodiments, the colon cancer-associated polypeptide genes correspond to SEQ ID NOs: 1–15. Encoded polypeptides (e.g., proteins), peptides and antisera thereto are also preferred for diagnosis and correspond to SEQ ID NOs: 16–30. In some embodiments, encoded polypeptides (e.g. proteins), peptides, and antisera thereto are ones other than those corresponding to SEQ ID NOs:16–30.

Some of the amino acid sequences identified by SEREX as colon cancer-associated polypeptides, and the nucleotide sequences encoding them, are newly identified and some are sequences deposited in databases such as GenBank. The use of the newly identified sequences in diagnostic assays for cancer is novel, as is the use of sets of at least two or more of the sequences in colon cancer diagnostic assays and kits.

Homologs and alleles of the colon cancer-associated polypeptide nucleic acids of the invention can be identified by conventional techniques. Thus, an aspect of the invention is those nucleic acid sequences that code for colon cancer-associated antigens and antigenic fragments thereof. As used herein, a homolog to a colon cancer-associated polypeptide is a polypeptide from a human or other animal that has a high degree of structural similarity to the identified colon cancer-associated polypeptides.

Identification of human and other organism homologs of colon cancer-associated polypeptides will be familiar to those of skill in the art. In general, nucleic acid hybridization is a suitable method for identification of homologous sequences of another species (e.g., human, cow, sheep), which correspond to a known sequence. Standard nucleic acid hybridization procedures can be used to identify related nucleic acid sequences of selected percent identity. For example, one can construct a library of cDNAs reverse transcribed from the MRNA of a selected tissue (e.g., colon) and use the nucleic acids that encode colon cancer-associated polypeptide identified herein to screen the library for related nucleotide sequences. The screening preferably is performed using high-stringency conditions to identify those sequences that are closely related by sequence identity. Nucleic acids so identified can be translated into polypeptides and the polypeptides can be tested for activity.

The term "high stringency" as used herein refers to parameters with which the art is familiar. Nucleic acid hybridization parameters may be found in references that compile such methods, e.g. *Molecular Cloning: A laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, high-stringency conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM NaH$_2$PO$_4$(pH7), 0.5% SDS, 2 mM EDTA). SSC is 0.15M sodium chloride/0.015M sodium citrate, pH7; SDS is sodium dodecyl sulphate; and EDTA is ethylenediaminetetracetic acid. After hybridization, the membrane upon which the DNA is transferred is washed, for example, in 2×SSC at room temperature and then at 0.1–0.5×SSC/0.1×SDS at temperatures up to 68° C.

There are other conditions, reagents, and so forth that can be used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of colon cancer-associated polypeptide nucleic acids of the invention (e.g., by using lower stringency conditions). The skilled artisan also is familiar with the methodology for screening cells and libraries for expression of such molecules, which then are routinely isolated, followed by isolation of the pertinent nucleic acid molecule and sequencing.

In general homologs and alleles typically will share at least 75% nucleotide identity and/or at least 90% amino acid identity to the sequences of colon cancer-associated antigen, antigenic fragment thereof, and antigen precursor thereof nucleic acid and polypeptides, respectively, in some instances will share at least 90% nucleotide identity and/or at least 95% amino acid identity, and in other instances will share at least 95% nucleotide identity and/or at least 99% amino acid identity. The homology can be calculated using various, publicly available software tools developed by NCBI (Bethesda, Md.) that can be obtained through the internet. Exemplary tools include the BLAST system available from the website of the National Center for Biotechnology Information (NCBI) at the National Institutes of Health. Pairwise and ClustalW alignments (BLOSUM30 matrix setting) as well as Kyte-Doolittle hydropathic analysis can be obtained using the MacVector sequence analysis software (Oxford Molecular Group). Watson-Crick complements of the foregoing nucleic acids also are embraced by the invention.

In screening for colon cancer-associated polypeptide genes, a Southern blot may be performed using the foregoing conditions, together with a detectably labeled probe (e.g. radioactive or chemiluminescent probes). After washing the membrane to which the DNA is finally transferred, the membrane can be placed against X-ray film or a phosphorimager to detect the radioactive or chemiluminescent signal. In screening for the expression of colon cancer-associated polypeptide nucleic acids, Northern blot hybridizations using the foregoing conditions can be performed on samples taken from colon cancer patients or subjects suspected of having a condition characterized by abnormal cell proliferation or neoplasia of the colorectal tissues. Amplification protocols such as polymerase chain reaction using primers that hybridize to the sequences presented also can be used for detection of the colon cancer-associated polypeptide genes or expression thereof.

Identification of related sequences can also be achieved using polymerase chain reaction (PCR) and other amplification techniques suitable for cloning related nucleic acid sequences. Preferably, PCR primers are selected to amplify portions of a nucleic acid sequence believed to be conserved (e.g., a catalytic domain, a DNA-binding domain, etc.). Again, nucleic acids are preferably amplified from a tissue-specific library (e.g., colon). One also can use expression cloning utilizing the antisera described herein to identify nucleic acids that encode related antigenic proteins in humans or other species using the SEREX procedure to screen the appropriate expression libraries. (See: Sahin et al. Proc. Natl. Acad. Sci. USA 92:11810–11813, 1995).

The invention also includes degenerate nucleic acids that include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating colon cancer-associated polypeptide. Similarly, nucleotide sequence triplets which encode other amino acid residues include, but are not limited to: CCA, CCC, CCG, and CCT (proline codons); CGA, CGC, CGG, CGT, AGA, and AGG (arginine codons); ACA, ACC, ACG, and ACT (threonine codons); AAC and AAT (asparagine codons); and ATA, ATC, and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides modified nucleic acid molecules, which include additions, substitutions and deletions of one or more nucleotides. In preferred embodiments, these modified nucleic acid molecules and/or the polypeptides they encode retain at least one activity or function of the unmodified nucleic acid molecule and/or the polypeptides, such as antigenicity, receptor binding, etc. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

For example, modified nucleic acid molecules that encode polypeptides having single amino acid changes can be prepared. Each of these nucleic acid molecules can have one, two or three nucleotide substitutions exclusive of nucleotide changes corresponding to the degeneracy of the genetic code as described herein. Likewise, modified nucleic acid molecules that encode polypeptides having two amino acid changes can be prepared which have, e.g., 2–6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s)) also can be prepared and are embraced by the invention as readily envisioned by one of ordinary skill in the art. Any of the foregoing nucleic acids or polypeptides can be tested by routine experimentation for retention of structural relation or activity to the nucleic acids and/or polypeptides disclosed herein.

The invention also provides nucleic acid molecules that encode antigenic fragments of colon cancer-associated proteins.

Fragments, can be used as probes in Southern and Northern blot assays to identify such nucleic acids, or can be used in amplification assays such as those employing PCR. As known to those skilled in the art, large probes such as 200, 250, 300 or more nucleotides are preferred for certain uses such as Southern and Northern blots, while smaller fragments will be preferred for uses such as PCR. Fragments also can be used to produce fusion proteins for generating antibodies or determining binding of the polypeptide fragments, or for generating immunoassay components. Likewise, fragments can be employed to produce nonfused fragments of the colon cancer-associated polypeptides, useful, for example, in the preparation of antibodies, and in immunoassays. Preferred fragments are antigenic fragments, which are recognized by agents that specifically bind to colon cancer-associated polypeptides. As used herein, colon cancer-associated antibodies, are antibodies that specifically bind to colon cancer-associated polypeptides.

The invention also permits the construction of colon cancer-associated polypeptide gene "knock-outs" or "knock-ins" in cells and in animals, providing materials for studying certain aspects of colon cancer and immune system responses to colon cancer by regulating the expression of colon cancer-associated polypeptides. For example, a knock-in mouse may be constructed and examined for clinical parallels between the model and a colon cancer-infected mouse with upregulated expression of a colon cancer-associated polypeptide, which may be useful to trigger an immune reaction to the polypeptide. Such a cellular or animal model may also be useful for assessing treatment strategies for colon cancer.

Alternative types of animal models for colon cancer may be developed based on the invention. Stimulating an immune response to a colon cancer-associated polypeptide in an animal may provide a model in which to test treatments, and assess the etiology of colon cancers.

The invention also provides isolated polypeptides (including whole proteins and partial proteins) encoded by the foregoing colon cancer-associated nucleic acids. Such polypeptides are useful, for example, alone or as fusion proteins to generate antibodies, and as components of an immunoassay or diagnostic assay. Colon cancer-associated polypeptides can be isolated from biological samples including tissue or cell homogenates, and can also be expressed recombinantly in a variety of prokaryotic and eukaryotic expression systems by constructing an expression vector appropriate to the expression system, introducing the expression vector into the expression system, and isolating the recombinantly expressed protein. Short polypeptides, such as colon cancer-associated antigen fragments including antigenic peptides also can be synthesized chemically using well-established methods of peptide synthesis.

Fragments of a polypeptide preferably are those fragments that retain a distinct functional capability of the polypeptide. Functional capabilities that can be retained in a fragment of a polypeptide include interaction with antibodies (e.g. antigenic fragments), interaction with other polypeptides or fragments thereof, selective binding of nucleic acids or proteins, and enzymatic activity. One important activity is the ability to provoke in a subject an immune response. As will be recognized by those skilled in the art, the size of the fragment will depend upon factors such as whether the epitope recognized by an antibody is a linear epitope or a conformational epitope. Thus, some antigenic fragments of colon cancer-associated polypeptides will consist of longer segments while others will consist of shorter segments, (e.g. 5, 6, 7, 8, 9, 10, 11 or 12 or more amino acids long, including each integer up to the full length of the colon cancer-associated polypeptide). Those skilled in the art are well versed in methods for selecting antigenic fragments of proteins.

The skilled artisan will also realize that conservative amino acid substitutions may be made in colon cancer-associated polypeptides to provide functionally equivalent variants, or homologs of the foregoing polypeptides, i.e, the variants retain the functional capabilities of the colon cancer-associated antigen polypeptides. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants or homologs of the colon cancer-associated polypeptides include conservative amino acid substitutions of in the amino acid sequences of proteins disclosed herein. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

For example, upon determining that a peptide is a colon cancer-associated polypeptide, one can make conservative amino acid substitutions to the amino acid sequence of the peptide, and still have the polypeptide retain its specific antibody-binding characteristics.

Conservative amino-acid substitutions in the amino acid sequence of colon cancer-associated polypeptides to produce functionally equivalent variants of colon cancer-associated polypeptides typically are made by alteration of a nucleic acid encoding a colon cancer-associated polypeptide. Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad Sci. U.S.A.* 82: 488–492, 1985), or by chemical synthesis of a gene encoding a colon cancer-associated polypeptide. Where amino acid substitutions are made to a small unique fragment of a colon cancer-associated polypeptide, such as an antigenic epitope recognized by autologous or allogeneic sera or cytolytic T lymphocytes, the substitutions can be made by directly synthesizing the peptide. The activity of functionally equivalent fragments of colon cancer-associated polypeptides can be tested by cloning the gene encoding the altered colon cancer-associated polypeptide into a bacterial or mammalian expression vector, introducing the vector into an appropriate host cell, expressing the altered polypeptide, and testing for a functional capability of the colon cancer-associated polypeptides as disclosed herein. Peptides that are chemically synthesized can be tested directly for function, e.g., for binding to antisera recognizing associated antigens.

The invention as described herein has a number of uses, some of which are described elsewhere herein. First, the invention permits isolation of the colon cancer-associated protein molecules. A variety of methodologies well-known to the skilled practitioner can be utilized to obtain isolated colon cancer-associated polypeptide molecules. The polypeptide may be purified from cells that naturally produce the polypeptide, by chromatographic means or immunological recognition. Alternatively, an expression vector may be introduced into cells to cause production of the polypeptide. In another method, mRNA transcripts may be microinjected or otherwise introduced into cells to cause production of the encoded polypeptide. Translation of mRNA in cell-free extracts such as the reticulocyte lysate system also may be used to produce polypeptide. Those skilled in the art also can readily follow known methods for isolating colon cancer-associated polypeptides. These include, but are not limited to, immunochromatography, HPLC, size-exclusion chromatography, ion-exchange chromatography, and immune-affinity chromatography.

The isolation and identification of colon cancer-associated polypeptides also permits the artisan to diagnose a disorder characterized by expression of colon cancer-associated polypeptides, and characterized preferably by an immune response against the colon cancer-associated polypeptides.

The methods related to colon cancer-associated polypeptide immune responses involve determining the immune response (antibody or cellular) against one or more colon cancer-associated polypeptides. The immune response can be assayed by any of the various immunoassay methodologies known to one of ordinary skill in the art. For example, the antigenic colon cancer-associated polypeptides can be used as a target to capture antibodies from a blood sample drawn from a patient in an ELISA assay.

The methods related to colon cancer-associated polypeptide expression involve determining expression of one or more colon cancer-associated nucleic acids, and/or encoded colon cancer-associated polypeptides and/or peptides derived therefrom and comparing the expression with that in a colon cancer-free subject. Such determinations can be carried out via any standard nucleic acid determination assay, including the polymerase chain reaction, or assaying with labeled hybridization probes. Such hybridization methods include, but are not limited to microarray techniques.

The invention also makes it possible to isolate proteins that specifically bind to colon cancer-associated antigens as disclosed herein, including antibodies and cellular binding partners of the colon cancer-associated polypeptides. Additional uses are described further herein.

The invention also involves agents such as polypeptides that bind to colon cancer-associated polypeptides. Such binding agents can be used, for example, in screening assays to detect the presence or absence of colon cancer-associated polypeptides and complexes of colon cancer-associated polypeptides and their binding partners and in purification protocols to isolate colon cancer-associated polypeptides and complexes of colon cancer-associated polypeptides and their binding partners. Such agents also may be used to inhibit the native activity of the colon cancer-associated polypeptides, for example, by binding to such polypeptides.

The invention, therefore, embraces peptide binding agents which, for example, can be antibodies or fragments of antibodies having the ability to selectively bind to colon cancer-associated polypeptides. Antibodies include polyclonal and monoclonal antibodies, prepared according to conventional methodology.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816,567, 5,225,539, 5,585,089, 5,693,762 and 5,859,205.

Fully human monoclonal antibodies also can be prepared by immunizing mice transgenic for large portions of human immunoglobulin heavy and light chain loci. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab)$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves polypeptides of numerous size and type that bind specifically to colon cancer-associated polypeptides, and complexes of both colon cancer-associated polypeptides and their binding partners. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the colon cancer-associated polypeptide. This process can be repeated through several cycles of reselection of phage that bind to the colon cancer-associated polypeptide. Repeated rounds lead to enrichment of phage bearing particular sequences. DNA sequence analysis can be conducted to identify the sequences of the expressed polypeptides. The minimal linear portion of the sequence that binds to the colon cancer-associated polypeptide can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the colon cancer-associated polypeptides.

Thus, the colon cancer-associated polypeptides of the invention, including fragments thereof, can be used to screen peptide libraries, including phage display libraries, to identify and select peptide binding partners of the colon cancer-associated polypeptides of the invention. Such molecules can be used, as described, for screening assays, for purification protocols, for interfering directly with the functioning of colon cancer-associated polypeptides and for other purposes that will be apparent to those of ordinary skill in the art. For example, isolated colon cancer-associated polypeptides can be attached to a substrate (e.g., chromatographic media, such as polystyrene beads, or a filter), and then a solution suspected of containing the binding partner may be applied to the substrate. If a binding partner that can interact with colon cancer-associated polypeptides is present in the solution, then it will bind to the substrate-bound colon cancer-associated polypeptide. The binding partner then may be isolated.

As detailed herein, the foregoing antibodies and other binding molecules may be used for example, to identify tissues expressing protein or to purify protein. Antibodies also may be coupled to specific diagnostic labeling agents for imaging of cells and tissues that express colon cancer-associated polypeptides or to therapeutically useful agents according to standard coupling procedures. Diagnostic agents include, but are not limited to, barium sulfate, iocetamic acid, iopanoic acid, ipodate calcium, diatrizoate sodium, diatrizoate meglumine, metrizamide, tyropanoate sodium and radiodiagnostics including positron emitters such as fluorine-18 and carbon-11, gamma emitters such as iodine-123, technitium-99m, iodine-131 and indium-111, nuclides for nuclear magnetic resonance such as fluorine and gadolinium.

The invention also includes methods to monitor the onset, progression, or regression of colon cancer in a subject by, for example, obtaining samples at sequential times from a subject and assaying such samples for the presence and/or absence of an antigenic response that is a marker of the condition. A subject may be suspected of having colon cancer or may be believed not to have colon cancer and in the latter case, the sample may serve as a normal baseline level for comparison with subsequent samples.

Onset of a condition is the initiation of the changes associated with the condition in a subject. Such changes may be evidenced by physiological symptoms, or may be clinically asymptomatic. For example, the onset of colon cancer may be followed by a period during which there may be colon cancer-associated physiological changes in the subject, even though clinical symptoms may not be evident at that time. The progression of a condition follows onset and is the advancement of the physiological elements of the condition, which may or may not be marked by an increase in clinical symptoms. In contrast, the regression of a condition is a decrease in physiological characteristics of the condition, perhaps with a parallel reduction in symptoms, and may result from a treatment or may be a natural reversal in the condition.

A marker for colon cancer may be the specific binding of a colon cancer-associated polypeptide with an antibody. Onset of a colon cancer condition may be indicated by the appearance of such a marker(s) in a subject's samples where there was no such marker(s) determined previously. For example, if marker(s) for colon cancer are determined not to be present in a first sample from a subject, and colon cancer marker(s) are determined to be present in a second or subsequent sample from the subject, it may indicate the onset of cancer.

Progression and regression of a colon cancer condition may be generally indicated by the increase or decrease, respectively, of marker(s) in a subject's samples over time. For example, if marker(s) for colon cancer are determined to be present in a first sample from a subject and additional marker(s) or more of the initial marker(s) for colon cancer are determined to be present in a second or subsequent sample from the subject, it may indicate the progression of cancer. Regression of cancer may be indicated by finding that marker(s) determined to be present in a sample from a subject are not determined to be found, or found at lower amounts in a second or subsequent sample from the subject.

The progression and regression of a colon cancer condition may also be indicated based on characteristics of the colon cancer-associated polypeptides determined in the subject. For example, some colon cancer-associated polypeptides may be abnormally expressed at specific stages of colon cancer (e.g. early-stage colon cancer-associated polypeptides; mid-stage colon cancer-associated polypeptides; and late-stage colon cancer-associated polypeptides). Another example, although not intended to be limiting, is that colon cancer-associated polypeptides may be differentially expressed in primary tumors versus metastases, thereby allowing the stage and/or diagnostic level of the disease to be established, based on the identification of selected colon cancer-associated polypeptides in a subject sample.

Another method of staging colon cancer may be based on variation in a subject's immune response to colon cancer-associated polypeptides, which may or may not be abnormally expressed in the subject. Variability in the immune response to the polypeptides may be used to indicate the stage of colon cancer in a subject, for example, some colon cancer-associated polypeptides may trigger an immune response at different stages of the colon cancer than that triggered by other colon cancer-associated polypeptides.

Different types of colon cancer, such as familial adenomatous polyposis (FAP) or to hereditary nonpolyposis colon cancer (HNPCC), also known as Lynch syndrome, may express different colon cancer-associated polypeptides and the encoding nucleic acid molecules thereof, or may have different spatial or temporal expression patterns. Such variations may allow cancer-specific diagnosis and subsequent treatment tailored to the patient's specific condition. These colon cancer-specific diagnoses may also be based on the variations in immune responses to the different colon cancer-associated polypeptides.

The invention includes kits for assaying the presence of colon cancer-associated polypeptides and/or antibodies that specifically bind to colon cancer-associated polypeptides. An example of such a kit may include the above-mentioned polypeptides bound to a substrate, for example a dipstick, which is dipped into a blood or body fluid sample of a subject. The surface of the substrate may then be processed using procedures well known to those of skill in the art, to assess whether specific binding occurred between the polypeptides and agents (e.g. antibodies) in the subject's sample. For example, procedures may include, but are not limited to, contact with a secondary antibody, or other method that indicates the presence of specific binding.

Another example of a kit may include an antibody or antigen-binding fragment thereof, that binds specifically to a colon cancer-associated polypeptide. The antibody or antigen-binding fragment thereof, may be applied to a tissue sample from a patient with colon cancer and the sample then processed to assess whether specific binding occurs between the antibody and a polypeptide or other component of the sample. In addition, the antibody or antigen-binding fragment thereof, may be applied to a stool sample from a subject, either suspected of having colon cancer, diagnosed with colon cancer, or believed to be free of colon cancer. As will be understood by one of skill in the art, such binding assays may also be performed with a sample or object contacted with an antibody and/or colon cancer-associated polypeptide that is in solution, for example in a 96-well plate or applied directly to an object surface.

The foregoing kits can include instructions or other printed material on how to use the various components of the kits for diagnostic purposes.

The invention further includes nucleic acid or protein microarrays with colon cancer-associated peptides or nucleic acids encoding such polypeptides. In this aspect of the invention, standard techniques of microarray technology are utilized to assess expression of the colon cancer-associated polypeptides and/or identify biological constituents that bind such polypeptides. The constituents of biological samples include antibodies, lymphocytes (particularly T lymphocytes), and the like. Protein microarray technology, which is also known by other names including: protein chip technology and solid-phase protein array technology, is well known to those of ordinary skill in the art and is based on, but not limited to, obtaining an array of identified peptides or proteins on a fixed substrate, binding target molecules or biological constituents to the peptides, and evaluating such binding. See, e.g., G. MacBeath and S. L. Schreiber, "Printing Proteins as Microarrays for High-Throughput Function Determination," Science 289(5485) :1760–1763, 2000. Nucleic acid arrays, particularly arrays that bind colon cancer-associated peptides, also can be used for diagnostic applications, such as for identifying subjects that have a condition characterized by colon cancer-associated polypeptide expression.

Microarray substrates include but are not limited to glass, silica, aluminosilicates, borosilicates, metal oxides such as alumina and nickel oxide, various clays, nitrocellulose, or nylon. The microarray substrates may be coated with a compound to enhance synthesis of a probe (peptide or nucleic acid) on the substrate. Coupling agents or groups on the substrate can be used to covalently link the first nucleotide or amino acid to the substrate. A variety of coupling agents or groups are known to those of skill in the art. Peptide or nucleic acid probes thus can be synthesized directly on the substrate in a predetermined grid. Alternatively, peptide or nucleic acid probes can be spotted on the substrate, and in such cases the substrate may be coated with a compound to enhance binding of the probe to the substrate. In these embodiments, presynthesized probes are applied to the substrate in a precise, predetermined volume and grid pattern, preferably utilizing a computer-controlled robot to apply probe to the substrate in a contact-printing manner or in a non-contact manner such as ink jet or piezoelectric delivery. Probes may be covalently linked to the substrate.

Targets are peptides or proteins and may be natural or synthetic. The tissue may be obtained from a subject or may be grown in culture (e.g. from a cell line).

In some embodiments of the invention, one or more control peptide or protein molecules are attached to the substrate. Preferably, control peptide or protein molecules allow determination of factors such as peptide or protein quality and binding characteristics, reagent quality and effectiveness, hybridization success, and analysis thresholds and success.

Nucleic acid microarray technology, which is also known by other names including: DNA chip technology, gene chip technology, and solid-phase nucleic acid array technology, is well known to those of ordinary skill in the art and is based on, but not limited to, obtaining an array of identified nucleic acid probes on a fixed substrate, labeling target molecules with reporter molecules (e.g., radioactive, chemiluminescent, or fluorescent tags such as fluorescein, Cye3-dUTP, or Cye5-dUTP), hybridizing target nucleic acids to the probes, and evaluating target-probe hybridization. A probe with a nucleic acid sequence that perfectly matches the target sequence will, in general, result in detection of a stronger reporter-molecule signal than will probes with less perfect matches. Many components and techniques utilized in nucleic acid microarray technology are presented in *The Chipping Forecast*, Nature Genetics, Vol.21, January 1999, the entire contents of which is incorporated by reference herein.

According to the present invention, nucleic acid microarray substrates may include but are not limited to glass, silica, aluminosilicates, borosilicates, metal oxides such as alumina and nickel oxide, various clays, nitrocellulose, or nylon. In all embodiments, a glass substrate is preferred. According to the invention, probes are selected from the group of nucleic acids including, but not limited to: DNA, genomic DNA, cDNA, and oligonucleotides; and may be natural or synthetic. Oligonucleotide probes preferably are 20 to 25-mer oligonucleotides and DNA/cDNA probes preferably are 500 to 5000 bases in length, although other lengths may be used. Appropriate probe length may be determined by one of ordinary skill in the art by following art-known procedures. In one embodiment, preferred probes are sets of more than two of the colon cancer-associated polypeptide nucleic acid molecules set forth herein, or one of the novel colon cancer-associated polypeptide nucleic acid molecules as described herein. Probes may be purified to remove contaminants using standard methods known to those of ordinary skill in the art such as gel filtration or precipitation.

In one embodiment, the microarray substrate may be coated with a compound to enhance synthesis of the probe on the substrate. Such compounds include, but are not limited to, oligoethylene glycols. In another embodiment, coupling agents or groups on the substrate can be used to covalently link the first nucleotide or olignucleotide to the substrate. These agents or groups may include, for example, amino, hydroxy, bromo, and carboxy groups. These reactive groups are preferably attached to the substrate through a hydrocarbyl radical such as an alkylene or phenylene divalent radical, one valence position occupied by the chain bonding and the remaining attached to the reactive groups. These hydrocarbyl groups may contain up to about ten carbon atoms, preferably up to about six carbon atoms. Alkylene radicals are usually preferred containing two to four carbon atoms in the principal chain. These and additional details of the process are disclosed, for example, in U.S. Pat. No. 4,458,066, which is incorporated by reference in its entirety.

In one embodiment, probes are synthesized directly on the substrate in a predetermined grid pattern using methods such as light-directed chemical synthesis, photochemical deprotection, or delivery of nucleotide precursors to the substrate and subsequent probe production.

In another embodiment, the substrate may be coated with a compound to enhance binding of the probe to the substrate. Such compounds include, but are not limited to: polylysine, amino silanes, amino-reactive silanes (Chipping Forecast, 1999) or chromium. In this embodiment, presynthesized probes are applied to the substrate in a precise, predetermined volume and grid pattern, utilizing a computer-controlled robot to apply probe to the substrate in a contact-printing manner or in a non-contact manner such as ink jet or piezoelectric delivery. Probes may be covalently linked to the substrate with methods that include, but are not limited to, UV-irradiation. In another embodiment probes are linked to the substrate with heat.

Targets for microarrays are nucleic acids selected from the group, including but not limited to: DNA, genomic DNA, cDNA, RNA, mRNA and may be natural or synthetic. In all embodiments, nucleic acid target molecules from human tissue are preferred. The tissue may be obtained from a subject or may be grown in culture (e.g. from a cell line).

In embodiments of the invention one or more control nucleic acid molecules are attached to the substrate. Preferably, control nucleic acid molecules allow determination of factors such as nucleic acid quality and binding characteristics, reagent quality and effectiveness, hybridization success, and analysis thresholds and success. Control nucleic acids may include but are not limited to expression products of genes such as housekeeping genes or fragments thereof.

In some embodiments, one or more control nucleic acid molecules are attached to the substrate. Preferably, control nucleic acid molecules allow determination of factors such as binding characteristics, reagent quality and effectiveness, hybridization success, and analysis thresholds and success.

EXAMPLES

Example 1

Method

Serum samples from patients with colon cancer were screened using a modification of the plaque assay, termed a spot assay. In this method, 80×120 mm nitrocellulose membranes were precoated with a film of NZY/0.7% Agarose/2.5 mM IPTG and placed on a reservoir layer of NZY/0.7% Agarose in a 86×128 mm Omni Tray (Nalge Nunc International Corp., Naperville, Ill.). Approximately $1.0 \times 10^5$ pfu of monoclonal phage encoding individual serologically defined colon cancer antigens, in a volume of 20 µl, were mixed with 20 µl of exponentially growing E. coli XL-1 Blue MRF and spotted (0.7-µl aliquots) on the precoated nitrocellulose membranes. Membranes were incubated for 15 hours at 37° C. A total of 75 different serologically defined colon cancer antigens were spotted in duplicate per nitrocellulose membrane. The agarose film was then removed from the membrane and the filters were processed for reactivity with individual serum samples (1:200 dilution), as described in Scanlan, et al., Int. J. Cancer 76:652–658 (1998) and Scanlan, et al., Int. J. Cancer 83:456–64, (1999).

Results

The results (see Table 1) indicate that 37/75 sera (49%) reacted with at least 1 antigen, 17/75 sera (23%) reacted with 2 or more antigens, 6/75 sera (8%) reacted with 3 or more antigens, and 2/75 sera (3%) reacted with 4 or more antigens. The reactivity of individual antigens is shown in Table 2.

TABLE 1

Colon Cancer Serology
Reactivity of 75 sera from colon cancer patients versus 15 antigens comprising, none of which react with normal sera (0/75, assayed by spot blot as described).

| Sera Number | Reactive NY-antigens |
|---|---|
| COF1 | Negative |
| COF2 | Negative |
| COF3 | Negative |
| COF4 | Negative |
| COF5 | Negative |
| COF6 | CO61 +++ |
| COF7 | CO26 ++++, ESO-1 ++++, CO61 ++++ |
| COF8 | Negative |
| COF9 | REN32 +++ |
| COF10 | p53 +++, CO58 ++ |
| COF11 | TNKL +, ESO-1 ++++ |
| COF12 | CO94 ++ |
| COF13 | Negative |
| COF14 | Negative |
| COF15 | SSX-2 ++ |
| COF16 | CO45 ++, CO42 ++ |
| COF17 | Negative |
| COF18 | Negative |
| COF19 | Negative |
| COF20 | Negative |
| COF21 | CO58 + |
| COF22 | TNKL ++, CO45 ++, CO42 ++ |
| COF23 | CO41 ++ |
| CO24 | Negative |
| CO25 | Negative |
| CO26 | TNKL +++ |
| CO27 | CO45 ++++ |

TABLE 1-continued

Colon Cancer Serology
Reactivity of 75 sera from colon cancer patients versus 15 antigens comprising, none of which react with normal sera (0/75, assayed by spot blot as described).

| Sera Number | Reactive NY-antigens |
|---|---|
| CO28 | CO9 ++++, ESO-1 ++++, CO58 ++++, CO61 ++ |
| CO29 | MAGE-3 +, ESO-1 + |
| CO30 | p53 +++ |
| CO31 | Negative |
| CO32 | Negative |
| CO33 | MAGE 3 +++ |
| CO34 | Negative |
| CO35 | Negative |
| CO36 | CO41 +++ |
| CO37 | Negative |
| CO38 | Negative |
| CO39 | Negative |
| CO40 | CO42 +, CO95 + |
| CO41 | Negative |
| CO42 | p53 ++++ |
| CO43 | p53 ++++, CO94 ++++ |
| CO44 | Negative |
| CO45 | p53 +++ |
| CO46 | Negative |
| CO47 | CO61 + |
| CO48 | p53 ++++, MAGE 3 ++ |
| CO49 | Negative |
| CO50 | Negative |
| CO51 | CO9 + |
| COF52 | Negative |
| CO53 | TNKL +, p53 ++++ |
| CO54 | Negative |
| CO55 | ESO-1 ++++ |
| CO56 | Negative |
| CO57 | Negative |
| CO58 | Negative |
| CO59 | Negative |
| CO60 | SSX-1 +, MAGE-3 +, CO42 +, CO61 ++++ |
| CO61 | TNKL ++ |
| **CO62 | **same sera as CO28 |
| **CO63 | **same sera as CO29 |
| CO64 | TNKL + |
| CO65 | Negative |
| **CO66 | **same sera as CO30 |
| CO67 | p53 ++ |
| CO68 | MAGE-3 +, CO42 + |
| CO69 | Negative |
| CO70 | Negative |
| CO71 | REN32 +, MAGE-3 + |
| CO72 | Negative |
| CO73 | REN32 ++, p53 + |
| CO74 | Negative |
| CO75 | p53 +++ |
| CO76 | Negative |
| CO77 | CO94 ++++, CO95 +++, p53 ++ |
| CO78 | CO42 ++, CO94 ++++, CO95 ++ |

TABLE 2

Reactivity of individual antigens (includes autologous where applicable)

| | |
|---|---|
| CO13 (p53) | 13/76 |
| CO-26 (MNK 1): | 2/76 |
| ESO-1: | 5/75 |
| REN-32 (Lamin C): | 3/75 |
| TNKL (BC-203): | 6/75 |
| SSX-2: | 2/75 |
| CO-45 (Tudor like): | 4/76 |
| CO-41 (MBD2): | 3/76 |
| MAGE-3 | 6/75 |
| CO-9 (HDAC 5) | 3/76 |
| CO-42 (TRIP4): | 7/76 |
| CO-61 (HIP1R): | 5/75 |
| CO-58 (KNSL6): | 3/75 |

TABLE 2-continued

Reactivity of individual antigens (includes autologous where applicable)

| CO-94 (seb4D): | 4/75 |
|---|---|
| CO-95 (KIAA1416) | 4/75 |

TABLE 3

Sequence Identification Numbers

| Sequence Name | Nucleotide SEQ ID NO | Protein SEQ ID NO. |
|---|---|---|
| CO-95 (KIAA1416) | 1 | 16 |
| CO-94 (seb4D) | 2 | 17 |
| CO-9 (HDAC 5) | 3 | 18 |
| CO-61 (HIP1R) | 4 | 19 |
| CO-58 (KNSL6) | 5 | 20 |
| CO-45 | 6 | 21 |
| CO-42 (TRIP4) | 7 | 22 |
| CO-41 (MBD2) | 8 | 23 |
| CO-13 (P53) | 9 | 24 |
| Ren-32 (Lamin C) | 10 | 25 |
| TNKL (BC-203) | 11 | 26 |
| CO-26 (MNK 1) | 12 | 27 |

TABLE 3-continued

Sequence Identification Numbers

| Sequence Name | Nucleotide SEQ ID NO | Protein SEQ ID NO. |
|---|---|---|
| SSX-2 | 13 | 28 |
| MAGE-3 | 14 | 29 |
| ESO-1 | 15 | 30 |

Other aspects of the invention will be clear to the skilled artisan and need not be repeated here. Each reference cited herein is incorporated by reference in its entirety.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A method for diagnosing colon cancer in a subject comprising:
   obtaining a biological sample from a subject,
   contacting the sample with at least two different colon cancer-associated polypeptides encoded by nucleic acid molecules comprising a nucleotide sequence selected from the group consisting of SEQ ID NOs:1 and 5, and
   determining specific binding between the colon cancer-associated polypeptides and agents in the sample, wherein the presence of specific binding is diagnostic for colon cancer in the subject.

2. The method of claim 1, wherein the sample is blood.

3. The method of claim 1, wherein the agents are antibodies or antigen-binding fragments of an antibody.

4. A method for determining onset, progression, or regression, of colon cancer in a subject, comprising:
   obtaining from a subject a first biological sample,
   contacting the first sample with at least two different colon cancer associated polypeptides encoded by nucleic acid molecules comprising a nucleotide sequence selected from the group consisting of SEQ ID NOs:1 and 5,
   determining specific binding between agents in the first sample and the at least two different colon cancer-associated polypeptides,
   obtaining subsequently from the subject a second biological sample, contacting the second biological sample with at least two different colon cancer-associated polypeptides encoded by nucleic acid molecules comprising a nucleotide sequence selected from the group consisting of SEQ ID NOs:1 and 5,
   determining specific binding between agents in the second sample and the at least two different colon cancer-associated polypeptides, and
   comparing the determination of binding in the first sample to the determination of specific binding in the second sample as a determination of the onset, progression, or regression of the colon cancer.

5. The method of claim 4, wherein the sample is a blood sample.

6. A kit for the diagnosis of colon cancer in a subject, comprising:
   at least two different colon cancer-associated polypeptides encoded by nucleic acid molecules comprising a nucleotide sequence selected from the group consisting of: SEQ ID NOs: 1 and 5, one or more control antigens, and instructions for the use of the polypeptides in the diagnosis of colon cancer.

7. The kit of claim 6, wherein the colon cancer-associated polypeptides are bound to a substrate.

8. A method for diagnosing colon cancer in a subject comprising:
   obtaining a biological sample from a subject,
   contacting the sample with a colon cancer-associated polypeptide encoded by a nucleic acid molecule comprising a nucleotide sequence selected from the group consisting of SEQ ID NOs: 1 and 5, and
   determining specific binding between the colon cancer-associated polypeptide and agents in the sample, wherein the presence of specific binding is diagnostic for colon cancer in the subject.

9. The method of claim 8, wherein the sample is blood.

10. The method of claim 8, wherein the agents are antibodies or antigen-binding fragments of an antibody.

11. A method for determining onset, progression, or regression, of colon cancer in a subject, comprising:
    obtaining from a subject a first biological sample,
    contacting the first sample with a colon cancer associated polypeptide encoded by a nucleic acid molecule comprising a nucleotide sequence selected from the group consisting of SEQ ID NOs:1 and 5,
    determining specific binding between agents in the first sample and the colon cancer-associated, polypeptide
    obtaining subsequently from the subject a second biological sample,
    contacting the second sample with a colon cancer associated polypeptide encoded by a nucleic acid molecule comprising a nucleotide sequence selected from the group consisting of SEQ ID NOs:1 and 5,
    determining specific binding between agents in the second sample and the colon cancer-associated polypeptide, and comparing the determination of binding in the first sample to the determination of specific binding in the second sample as a determination of the onset, progression, or regression of colon cancer.

12. The method of claim 4, wherein the agents are antibodies or antigen-binding fragments therefor of an antibody.

13. The method of claim 11, wherein the sample is a blood sample.

14. The method of claim 11, wherein the agents are antibodies or antigen-binding fragments therefor of an antibody.

* * * * *